US010780171B2

(12) United States Patent
Mooney et al.

(10) Patent No.: US 10,780,171 B2
(45) Date of Patent: Sep. 22, 2020

(54) REDUCED AND OXIDIZED POLYSACCHARIDES AND METHODS OF USE THEREOF

(71) Applicant: President and Fellows of Harvard College, Cambridge, MA (US)

(72) Inventors: David J. Mooney, Sudbury, MA (US); Alexander Stafford, Revere, MA (US); Rajiv Desai, San Diego, CA (US); Kathleen Martinick, Medford, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/770,937

(22) PCT Filed: Oct. 26, 2016

(86) PCT No.: PCT/US2016/058866
§ 371 (c)(1),
(2) Date: Apr. 25, 2018

(87) PCT Pub. No.: WO2017/075055
PCT Pub. Date: May 4, 2017

(65) Prior Publication Data
US 2018/0326073 A1 Nov. 15, 2018

Related U.S. Application Data

(60) Provisional application No. 62/351,162, filed on Jun. 16, 2016, provisional application No. 62/246,462, filed on Oct. 26, 2015.

(51) Int. Cl.
| | | |
|---|---|---|
| *A61K 47/36* | (2006.01) | |
| *A61K 9/127* | (2006.01) | |
| *A61K 9/10* | (2006.01) | |
| *A61K 9/06* | (2006.01) | |
| *C08L 5/04* | (2006.01) | |
| *A61K 9/00* | (2006.01) | |
| *C08B 37/00* | (2006.01) | |
| *A61K 47/69* | (2017.01) | |
| *A61K 9/51* | (2006.01) | |

(52) U.S. Cl.
CPC ............ *A61K 47/36* (2013.01); *A61K 9/0046* (2013.01); *A61K 9/0048* (2013.01); *A61K 9/06* (2013.01); *A61K 9/10* (2013.01); *A61K 9/127* (2013.01); *A61K 9/1271* (2013.01); *A61K 9/5161* (2013.01); *A61K 47/6903* (2017.08); *C08B 37/0084* (2013.01); *C08L 5/04* (2013.01)

(58) Field of Classification Search
CPC .... A61K 47/36; A61K 9/0048; A61K 9/0046; A61K 9/06; A61K 9/10; A61K 9/127; A61K 9/5161; A61K 9/1271; A61K 47/6903; C08B 37/0084; C08L 5/04; A61P 9/10; A61P 43/00; A61P 27/16; A61P 27/02
See application file for complete search history.

(56) References Cited

U.S. PATENT DOCUMENTS

| | | | |
|---|---|---|---|
| 3,516,838 A * | 6/1970 | Du Puis | A23L 3/358 426/532 |
| 3,784,475 A | 1/1974 | Diehl | |
| 5,652,346 A | 7/1997 | Detty et al. | |
| 6,586,589 B1 | 7/2003 | Marritt | |
| 6,642,363 B1 | 11/2003 | Mooney et al. | |
| 2003/0125238 A1 | 7/2003 | Adamson | |
| 2004/0028745 A1 | 2/2004 | Bouhadir et al. | |
| 2013/0230493 A1 | 9/2013 | Alsberg et al. | |
| 2014/0105960 A1 | 4/2014 | Zoldan et al. | |

FOREIGN PATENT DOCUMENTS

| | | |
|---|---|---|
| WO | 1999/29328 A1 | 6/1999 |
| WO | 2003/072155 A1 | 9/2003 |
| WO | 2009/013358 A2 | 1/2009 |
| WO | 2011/109834 A2 | 9/2011 |
| WO | 2012/048165 A2 | 4/2012 |
| WO | 2015/154078 A1 | 10/2015 |

OTHER PUBLICATIONS

Supplementary European Search Report for Application No. 16860689.5, dated Apr. 23, 2019, 16 pages.
Balakrishnan et al., Self-cross-linking biopolymers as injectable in situ forming biodegradable scaffolds. Biomaterials. Jun. 2005;26(18):3941-51.
Boontheekul et al., Controlling alginate gel degradation utilizing partial oxidation and bimodal molecular weight distribution. Biomaterials. May 2005;26(15):2455-65.
Borselli et al., Functional muscle regeneration with combined delivery of angiogenesis and myogenesis factors. Proc Natl Acad Sci U S A. Feb. 23, 2010;107(8):3287-92.
Desai et al., Versatile click alginate hydrogels crosslinked via tetrazine-norbornene chemistry. Biomaterials. May 2015;50:30-7.
Khan et al., Polysaccharides and their derivatives for versatile tissue engineering application. Macromol Biosci. Apr. 2013;13(4):395-421.

(Continued)

*Primary Examiner* — Robert S Cabral
(74) *Attorney, Agent, or Firm* — McCarter & English, LLP; Maria Laccotripe Zacharakis

(57) ABSTRACT

The present invention is directed to reduced and highly oxidized polysaccharides, such as alginates, that are useful for encapsulating therapeutic or diagnostic agents, or lipid based nanoparticles, e.g., liposomes or virosomes, encapsulating therapeutic or diagnostic agents, prior to their delivery into a subject, as well as methods for making and using them.

23 Claims, 49 Drawing Sheets

(56) References Cited

OTHER PUBLICATIONS

Kharkar et al., Designing degradable hydrogels for orthogonal control of cell microenvironments. Chem Soc Rev. Sep. 7, 2013;42(17):7335-72.
Lee et al., Alginate: properties and biomedical applications. Prog Polym Sci. Jan. 2012;37(1):106-126.
Mufamadi et al., A review on composite liposomal technologies for specialized drug delivery. J Drug Deliv. 2011;2011:939851. 19 pages.
Ramachandran et al., Efficient Synthesis of Enantiomerically Pure C2-Symmetric Diols via the Allylboration of Appropriate Dialdehyde. Tetrahedron Letters. Apr. 7, 1997;38(14):2417-2420.
Sun et al., Alginate-Based Biomaterials for Regenerative Medicine Applications. Materials (Basel). Mar. 26, 2013;6(4):1285-1309.
Vold et al., A study of the chain stiffness and extension of alginates, in vitro epimerized alginates, and periodate-oxidized alginates using size-exclusion chromatography combined with light scattering and viscosity detectors. Biomacromolecules. Jul. 2006;7(7):2136-46.
International Search Report and Written Opinion for Application No. PCT/US2016/058866, dated Jan. 25, 2017. 13 pages.

\* cited by examiner

UnOxidized Alginate Conjugation

Oxidized Alginate Conjugation and Imines

Clicks conjugated directly to HighOx Alginates
Left to Right: 20% – 50% Ox, showing significant color changes Clicks conjugated directly to High Ox Alginates Day 0

Clicks conjugated directly to High Ox SC Alginates Day 0

20–50 % Oxidation — Tetrazine Day 28

20–50 % Oxidation Sodium Chlorite — Tetrazine Day 14

20–50 % Oxidation — Norbornene Day 28

20–50 % Oxidation Sodium Chlorite — Norbornene Day 14

Vial 1 - 20%Ox MVG AB Nb at 50% w/v
Vial 1 - 20%Ox MVG AB Tz at 50% w/v
Vial 3 - 20%Ox MVG SC Tz at 50% w/v
Vial 4 - 20%Ox MVG SC Nb at 50% w/v
Vial 5 - Unoxidized VLVG at 50% w/v (soluble at < 15% w/v)

T = 0 min

T = 40 min

T = 21.5 hours

T = 67.5 hours

T = 0 min

T = 40 min

T = 20 hours

T = 69 hours

Day 0

Day 1

Day 7

Day 14

REDUCED AND OXIDIZED POLYSACCHARIDES AND METHODS OF USE THEREOF

RELATED APPLICATIONS

This application is a 35 U.S.C. § 371 national stage filing of International Application No. PCT/US2016/058866, filed on Oct. 26, 2016, which claims priority to U.S. Provisional Application No. 62/246,462, filed on Oct. 26, 2015 and U.S. Provisional Application No. 62/351,162, filed on Jun. 16, 2016. The entire contents of each of the foregoing applications are incorporated herein by reference.

BACKGROUND OF THE INVENTION

A hydrogel is a polymer gel comprising a network of crosslinked polymer chains. The network structure of hydrogels allows them to absorb significant amounts of water. Some hydrogels are highly stretchable and elastic; others are viscoelastic. Hydrogels have been used for therapeutic applications, e.g., as vehicles for in vivo delivery of therapeutic agents, such as small molecules, cells and biologics.

Hydrogels are commonly produced from polysaccharides, such as alginates. The polysaccharides may be chemically manipulated to modulate their properties and properties of the resulting hydrogels. For example, oxidizing a polysaccharide by reacting it with an oxidizing agent that converts alcohols in the polysaccharide into aldehydes, significantly increases the biodegradability of the resulting hydrogel. However, the oxidation of polysaccharides is also associated with undesirable side effects. For example, the aldehydes produced by oxidation can react with amino groups present on proteins or other molecules, causing in vivo toxicity and/or damage to therapeutic agents (cargo) that may be encapsulated by hydrogels produced from the oxidized polysaccharides. The aldehydes present in an oxidized polysaccharide can also react with various chemical moieties that may be present in the vicinity of the polysaccharide, such as click reagents, resulting in their degradation. Accordingly, there is a need in the art for biodegradable polysaccharides that may be used for preparing hydrogels that are non-toxic, non-reactive and biodegradable. There is also a need in the art for polysaccharides that may be used to prepare hydrogels with a sufficiently small pore size for encapsulating therapeutic agents of small molecular weights. There is also a need in the art for polysaccharides that may be used to prepare hydrogels capable of encapsulating and retaining liposomes and delivering the liposomes to a desired location in vivo.

SUMMARY OF THE INVENTION

The present invention provides compositions comprising certain reduced and certain highly oxidized polysaccharides. It has been surprisingly discovered that these reduced and highly oxidized polysaccharides are particularly well suited for producing hydrogels that may be used for encapsulating therapeutic or diagnostic agents or for encapsulating lipid based nanoparticles, e.g., liposomes or virosomes, used for encapsulating therapeutic or diagnostic agents, for delivery to a subject. The hydrogels of the invention produced using the reduced and/or highly oxidized polysaccharides are biodegradable and less toxic and reactive than the hydrogels previously known in the art.

Accordingly, in some embodiments, the present invention provides a composition comprising a reduced polysaccharide, wherein the reduced polysaccharide comprises less than 2% of residual aldehydes.

In some embodiments, the present invention also provides a composition comprising a reduced polysaccharide, wherein the reduced polysaccharide comprises less than 3% of residual aldehydes; wherein the reduced polysaccharide is produced by reacting a polysaccharide with a diol specific oxidizing agent, thereby producing an oxidized polysaccharide comprising 0.1% or more oxidation on a molar basis; followed by reacting said oxidized polysaccharide with a water soluble aldehyde specific reducing agent to produce the reduced polysaccharide.

In some aspects, the reduced polysaccharide is produced by reacting a polysaccharide with a diol specific oxidizing agent, thereby producing a diol containing oxidized polysaccharide comprising 0.1% or more oxidation on a molar basis; followed by reacting said oxidized polysaccharide with a water soluble aldehyde specific reducing agent to produce said reduced polysaccharide.

In some aspects, also provided is a composition comprising a reduced polysaccharide, wherein the reduced polysaccharide is produced by reacting a polysaccharide with a diol specific oxidizing agent, thereby producing a diol containing oxidized polysaccharide; followed by reacting the oxidized polysaccharide with a water soluble aldehyde specific reducing agent to produce said reduced polysaccharide. In some aspects, the polysaccharide comprises less than 15% residual aldehydes, e.g., 14%, 13%, 12%, 11%, 10%, 9%, 8%, 7%, 6%, 5%, 4%, 3%, 2%, 1%, 0.5% or 0.1%.

In some embodiments, the polysaccharide is selected from the group consisting of alginate, agarose, pullulan, scleroglucan, chitosan, elsinan, xanthan gum, dextran, mannose, gellan, levan, cellulose, hyaluronic acid, chondroitin sulfate A, chondroitin sulfate C, chondroitin sulfate E and β-d-glucans. In one embodiment, the polysaccharide is alginate. In one embodiment, the reduced polysaccharide comprises algoxinol having the following structure:

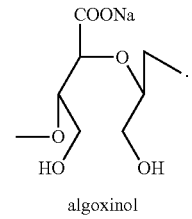

algoxinol

In some aspects, the aldehyde specific water soluble reducing agent is selected from the group consisting of sodium borohydride ($NaBH_4$); sodium cyanoborohydride ($NaCNBH_3$); hydrogen gas ($H_2$) in the presence of a catalyst; ammonia borane ($H_3NBH_3$); and a borane complex. In a specific embodiment, the aldehyde specific water soluble reducing agent is ammonia borane. In another specific embodiment, the diol specific oxidizing agent is sodium periodate.

In some embodiments, the composition further comprises a cross-linking agent attached to the reduced polysaccharide. In some aspects, the cross-linking agent is a click reagent, e.g., a click reagent is selected from the group consisting of azide, dibenzocyclooctyne (DBCO), transcyclooctene, tetrazine and norbornene and variants thereof.

In some embodiments, the present invention also provides a composition comprising a reduced polysaccharide and a cross-linking agent attached to the reduced polysaccharide.

In some aspects, the polysaccharide is an alginate polymer. In some embodiments, the reduced polysaccharide comprises algoxinol having the following structure:

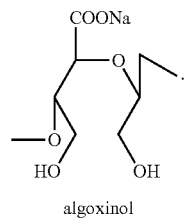

algoxinol

In some embodiments, the reduced polysaccharide is produced by a method comprising the steps of reacting the polysaccharide with a diol specific oxidizing agent to produce an aldehyde containing oxidized polysaccharide; and reacting the oxidized polysaccharide with a water soluble aldehyde specific reducing agent to produce the reduced polysaccharide.

In some embodiments, the diol specific oxidizing agent is sodium periodate. In some embodiments, the water soluble aldehyde specific reducing agent is ammonia borane.

In some aspects, provided is a composition comprising a highly oxidized polysaccharide and a cross-linking agent attached to the highly oxidized polysaccharide. In some embodiments, the polysaccharide is an alginate polymer. In some aspects, the highly oxidized polysaccharide comprises algoxalate having the following structure:

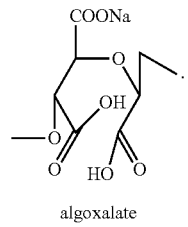

algoxalate

In some embodiments, the highly oxidized polysaccharide is produced by a method comprising the steps of reacting the polysaccharide with a diol specific oxidizing agent to produce an aldehyde containing oxidized polysaccharide; and reacting the oxidized polysaccharide with a second oxidizing agent which converts aldehydes into carboxylic acids to produce said highly oxidized polysaccharide.

In one aspect, the diol specific oxidizing agent is sodium periodate. In another aspect, the second oxidizing agent is sodium chlorite.

In some embodiments, the cross-linking agent is a click reagent, e.g., a click reagent selected from the group consisting of azide, dibenzocyclooctyne (DBCO), transcyclooctene, tetrazine and norbornene and variants thereof.

In some embodiments, the present invention also provides a hydrogel comprising the compositions of the invention.

In some aspects, the hydrogel may further comprise a therapeutic agent, e.g., selected from the group consisting of a cell, a small molecule and a biologic. In some embodiments, the biologic is selected from the group consisting of a peptide, a DNA molecule, an RNA molecule, and a PNA molecule. In one embodiment, the biologic is a peptide, e.g., an angiogenesis factor, e.g., selected from the group consisting of FGF, VEGF, VEGFR, IGF, NRP-1, Ang1, Ang2, PDGF, PDGFR, TGF-β, endoglin, a TGF-β receptor, MCP-1, integrin, VE-cadherin, CD31, ephrin, plasminogen activator, plasminogen activator inhibitor-1, eNOS, COX-2, AC133, ID1, ID3, and HGF. In a specific aspect, the angiogenesis factor is VEGF.

In some embodiments, the hydrogel of the invention further comprises a cell, e.g., a mammalian cell, such as a human mesenchymal stem cell (hMSC).

In some aspects, the present invention provides a hydrogel comprising a plurality of reduced and/or oxidized polysaccharides cross-linked to each other, wherein the hydrogel comprises a mesh size of about 10 nm or less, e.g., about 10 nm, about 9 nm, about 8 nm, about 7 nm, about 6 nm, about 5 nm, about 4 nm, about 3 nm, about 2 nm or about 1 nm or less.

In some embodiments, the oxidized polysaccharides are highly oxidized alginate polymers. In some embodiments, the highly oxidized alginate polymers are produced by a method comprising the steps of reacting an alginate with a diol specific oxidizing agent to produce an aldehyde containing oxidized alginate; and reacting the aldehyde containing oxidized alginate with a second oxidizing agent which converts aldehydes into carboxylic acids, thereby producing said highly oxidized alginate polymers.

In one embodiment, the diol specific oxidizing agent is sodium periodate. In another embodiment, the second oxidizing agent is sodium chlorite.

In some embodiments, the oxidized alginate polymers are about 0.1% 1%, 5%, 10%, 15%, 20%, 25%, 30%, 35%, 40%, 45%, 50%, 55%, 60%, 65%, 70%, 75%, 80%, 85%, 90%, 95% or 99% oxidized.

In some embodiments, the reduced polysaccharides are reduced alginate polymers. In some embodiments, the reduced alginate polymers are produced by a method comprising the steps of reacting an alginate with a diol specific oxidizing agent to produce an aldehyde containing oxidized alginate; and reacting the aldehyde containing oxidized alginate with a water soluble aldehyde specific reducing agent, thereby producing said reduced alginate polymers.

In one embodiment, the diol specific oxidizing agent is sodium periodate. In another embodiment, the water soluble aldehyde specific reducing agent is ammonia borane.

In some aspects, the hydrogel of the invention comprises an average mesh size of about 10 nm to about 1 nm, about 10 nm to about 4 nm, about 7 nm to about 3 nm, about 5 nm to about 1 nm, about 4 nm to about 2 nm, or about 3 nm to about 0.5 nm.

In some aspects, the hydrogel of the invention further comprises a therapeutic or diagnostic agent, e.g., a cell, a small molecule and a biologic. In some aspects, the biologic is selected from the group consisting of a peptide, a DNA molecule, an RNA molecule, and a PNA molecule.

In some embodiments, the biologic is a peptide. In some embodiments, the peptide has a molecular weight of 500 kDa or less, e.g., about 450 kDa or less, about 300 kDa or less, about 150 kDa or less, about 100 kDa or less, about 50 kDa or less, about 25 kDa or less or about 10 kDa or less.

In some aspects, the peptide is an angiogenesis factor, e.g., FGF, VEGF, VEGFR, NRP-1, Ang1, Ang2, PDGF, PDGFR, IGF, TGF-β, endoglin, a TGF-β receptor, MCP-1, integrin, an integrin ligand, VE-cadherin, CD31, ephrin, plasminogen activator, plasminogen activator inhibitor-1, eNOS, COX-2, AC133, ID1, ID3, and HGF. In a specific embodiment, the angiogenesis factor is VEGF.

In some embodiments the cell is a mammalian cell, e.g., a human mesenchymal stem cell (hMSC).

In some embodiments, the polysaccharides comprise a cross-linking agent attached to the polysaccharides. In some aspects, the cross-linking agent is a click reagent, e.g., azide, dibenzocyclooctyne, transcyclooctene, tetrazine and norbornene and variants thereof.

In some embodiments, the present invention also provides an implantable or injectable device comprising the hydrogel of the invention.

In some aspects, the present invention also provides a method of producing a reduced polysaccharide, the method comprising the steps of reacting a polysaccharide with a diol specific oxidizing agent to produce an aldehyde containing oxidized polysaccharide; and reacting the aldehyde containing oxidized polysaccharide with an aldehyde specific water soluble reducing agent, thereby producing the reduced polysaccharide.

In some embodiments, the aldehyde specific water soluble reducing agent is sodium borohydride ($NaBH_4$); sodium cyanoborohydride ($NaCNBH_3$); hydrogen gas ($H_2$) in the presence of a catalyst, e.g., a nickel (Ni), a platinum (Pl) or a palladium (Pd) catalyst; ammonia borane ($H_3NBH_3$); or a borane complex, e.g., a bis-carbonate borane complex ($[BH_3]_2CO_2]^{2-} \cdot 2Na^+$), a borane dimethylamine complex $[(CH_3)_2NH \cdot BH_3]$; a borane tert-butylamine complex $[(CH_3)_3CNH_2 \cdot BH_3]$; or a borane-pyrimidine complex. In a specific embodiment, the aldehyde specific water soluble reducing agent is ammonia borane. In another specific embodiment, the diol specific oxidizing agent is sodium periodate.

In some embodiments, the method further comprises reacting said polysaccharide with a cross-linking agent. In some aspects, the cross-linking reagent is a click reagent, e.g., azide, dibenzocyclooctyne (DBCO), transcyclooctene, tetrazine and norbornene and variants thereof. In a specific embodiment, the polysaccharide is an alginate polymer. In an embodiment, the alginate polymer is of a molecular weight of less than 500 kDa. In an embodiment, the reduced polysaccharide comprises algoxinol having the following structure:

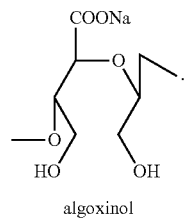

algoxinol

In some aspects, the present invention also provides a method of producing a highly oxidized polysaccharide covalently attached to a cross-linking agent, the method comprising the steps of reacting a polysaccharide with a diol specific oxidizing agent to produce an aldehyde containing oxidized polysaccharide; reacting the aldehyde containing oxidized polysaccharide with a second oxidizing agent which converts aldehydes into carboxylic acids, thereby producing the highly oxidized polysaccharide; and reacting the polysaccharide with a cross-linking agent.

In some aspects, the second oxidizing agent is selected from the group consisting of sodium chlorite, bromine, dilute nitric acid (NHO3), silver oxide, a copper(II) complex, potassium permanganate (KMnO4) and hydrogen peroxide ($H_2O_2$). In a specific embodiment, the second oxidizing agent is sodium chlorite.

In some embodiments, the cross-linking agent is a click reagent, e.g., azide, dibenzocyclooctyne (DBCO), transcyclooctene, tetrazine and norbornene and variants thereof.

In some aspects, the polysaccharide is an alginate polymer. In one aspect, the alginate polymer has a molecular weight of less than 500 kDa.

In one embodiment, the highly oxidized polymer comprises algoxalate having the following structure:

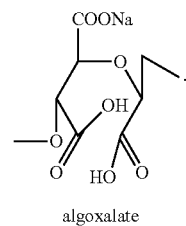

algoxalate

The present invention also provides a drug delivery composition comprising a lipid based nanoparticle encapsulating a therapeutic or diagnostic agent; and the hydrogel of the invention encapsulating the lipid based nanoparticle. In an embodiment, the lipid based nanoparticle is a liposome or a virosome.

In some embodiments, the lipid based nanoparticle remains encapsulated in the hydrogel for at least 1 day, at least 10 days, at least 15 days, at least 20 days, at least 25 days, at least 30 days, at least 35 days, at least 40 days, at least 45 days, at least 50 days, at least 55 days, at least 60 days, at least 65 days, at least 70 days, at least 75 days or at least 80 days.

In some aspects, the therapeutic or diagnostic agent is selected from the group consisting of a cell, a small molecule and a biologic. In some aspects, the biologic is selected from the group consisting of a peptide, an antibody or a fragment thereof, a vaccine, a DNA molecule, an RNA molecule, and a PNA molecule. In some aspects, the therapeutic or diagnostic agent is selected from the group consisting of a STING adjuvant, a CRISPR-Cas 9 reagent and an adjuvant-loaded subcellular vesicle derived from disrupted cancer cells. In some aspects, the therapeutic or diagnostic agent is a vaccine.

In some aspects, the present invention also provides a drug delivery composition, comprising a lipid based nanoparticle encapsulating a therapeutic or diagnostic agent; and a click-conjugated polymer hydrogel encapsulating the lipid based nanoparticle, wherein the click-conjugated polymer hydrogel comprises a biodegradable polymer; and wherein the polymer is not susceptible to degradation by a host endogenous enzyme. In an embodiment, the lipid based nanoparticle is a liposome or a virosome.

In some embodiments, the drug delivery composition allows a sustained delivery of intact lipid based nanoparticle to a desired location in the host.

In some embodiments, the polysaccharide is selected from the group consisting of alginate, agarose, pullulan, scleroglucan, chitosan, elsinan, xanthan gum, dextran, mannose, gellan, levan, cellulose, hyaluronic acid, chondroitin sulfate A, chondroitin sulfate C, chondroitin sulfate E and β-d-glucans. In a specific embodiment, the polysaccharide is alginate.

In some aspects, the click-conjugated polymer hydrogel is generated by use of at least one click reagent selected from the group consisting of azide, dibenzocyclooctyne, transcyclooctene, tetrazine and norbornene and variants thereof.

In some embodiments, the alginate comprises a degree of click substitution of about 0.01% to about 99%, e.g., about 0.01% to about 0.05%, about 0.02% to about 0.1%, about 0.05% to about 0.5%, about 0.1% to about 1%, about 0.5% to about 15%, about 5% to about 10%, about 2% to about 20%, about 15% to about 40%, about 30% to about 50%, about 40% to about 70%, about 50% to about 80% or about 60% to about 99%. In some aspects, the click-conjugated polymer hydrogel comprises alginate that is about 0.1% to about 99% oxidized, e.g., about 0.1% to about 0.5%, about 0.2% to about 1%, about 0.5% to about 10%, about 5% to about 20%, about 15% to about 40%, about 25% to about 50%, about 40% to about 70%, about 50% to about 80% or about 75% to about 99% oxidized.

In some aspects, the click-conjugated alginate hydrogel has been prepared from alginate present at a concentration of about 1% to about 99% w/v, e.g., about 1% to about 5%, about 2% to about 10%, about 5% to about 20%, about 10% to about 30%, about 20% to about 50%, about 40% to about 70%, about 60% to about 80% or about 75% to about 99% w/v. In some embodiments, the lipid based nanoparticle remains encapsulated in the click-conjugated polymer hydrogel for at least 1 days, at least 10 days, at least 15 days, at least 20 days, at least 25 days, at least 30 days, at least 35 days, at least 40 days, at least 45 days, at least 50 days, at least 55 days, at least 60 days, at least 65 days, at least 70 days, at least 75 days or at least 80 days.

In some aspects, the present invention also provides a drug delivery composition, comprising a lipid based nanoparticle encapsulating a therapeutic or diagnostic agent; and an alginate hydrogel encapsulating the lipid based nanoparticle, wherein the hydrogel comprises alginate comprising about 50% or less oxidation on a molar basis, e.g., about 45% or less, about 40% or less, about 35% or less, about 30% or less, about 25% or less, about 20% or less, about 15% or less, about 10% or less, about 5% or less, about 1% or less, about 0.5% or less or about 0.1% or less. In an embodiment, the lipid based nanoparticle is a liposome or a virosome. In one aspect, composition allows a sustained delivery of intact lipid based nanoparticle to a desired location in a host.

In some aspects, the click-conjugated polymer hydrogel is generated by use of at least one click reagent selected from the group consisting of azide, dibenzocyclooctyne, transcyclooctene, tetrazine and norbornene and variants thereof. In some aspects, the alginate is conjugated to a click reagent and wherein the alginate comprises a degree of click substitution of about 0.01% to about 90%.

In some aspects, the click-conjugated polymer hydrogel comprises alginate that is about 0.1% to about 99% oxidized.

In some embodiments, the alginate hydrogel has been prepared from alginate present at the concentration of about 1% to about 80% w/v. In some embodiments, the lipid based nanoparticle remains encapsulated in the hydrogel for at least 1 days, at least 10 days, at least 15 days, at least 20 days, at least 25 days, at least 30 days, at least 35 days, at least 40 days, at least 45 days, at least 50 days, at least 55 days, at least 60 days, at least 65 days, at least 70 days, at least 75 days or at least 80 days.

In some aspects, the therapeutic or diagnostic agent is selected from the group consisting of a cell, a small molecule and a biologic. In some embodiments, the biologic is selected from the group consisting of a peptide, an antibody or a fragment thereof, a vaccine, a DNA molecule, an RNA molecule, and a PNA molecule. In some embodiments, the RNA molecule is selected from the group consisting of an mRNA, an RNAi, an siRNA, an shRNA, a microRNA, an isRNA, a lncRNA and an antisense RNA.

In some aspects, the therapeutic or diagnostic agent is selected from the group consisting of a STING adjuvant, a CRISPR-Cas 9 reagent and an adjuvant-loaded subcellular vesicle derived from disrupted cancer cells.

In some embodiments, the liposome is a cationic liposome. In some aspects, the desired location is the cytosol of a cell.

In some embodiments, the present invention also provides a method for treating a subject in need thereof, the method comprising administering to the subject an effective amount of the hydrogel, the implantable or injectable device or the drug delivery composition of the invention, thereby treating said subject.

In some aspects, the subject is suffering from a disease or a condition selected from the group consisting of ischemia, an eye related disorder or an ear related disorder.

In some embodiments, the present invention also provides a method of treating chronic ischemia or enhancing engraftment of a transplanted tissue in a subject in need thereof, the method comprising administering to said subject an effective amount of the hydrogel, the implantable or injectable device or the drug delivery composition of the invention, thereby treating said chronic ischemia or enhancing engraftment of said transplanted tissue in said subject.

In some aspects, the hydrogel or the implantable or injectable device or the drug delivery composition is administered locally, e.g., to a site of ischemia or to the tissue to be engrafted before and/or after transplantation.

In some aspects, the hydrogel or the implantable or injectable device or the drug delivery composition comprises a peptide at a dose that is at least about 10 times smaller, e.g., about about 15 times smaller, about 20 times smaller, about 50 times smaller, than the recommended dose for said peptide when said peptide is delivered in soluble form.

In a specific aspect, the peptide is VEGF and IGF. In an embodiment, the subject is a human.

The present invention is further illustrated by the following detailed description and drawings.

BRIEF DESCRIPTION OF THE DRAWINGS

FIG. 6a illustrates the change in Tz UV-Vis spectrum caused by the reaction of the click moieties with alginate aldehydes present in the oxidized alginate material.

FIG. 6b illustrates the change in the color of the Tz solution caused by the reaction of click moieties with alginate aldehydes present in the oxidized alginate material.

FIG. 6c illustrates the change in Nb UV-Vis spectrum caused by the reaction of the click moieties with alginate aldehydes present in the oxidized alginate material.

FIG. 6d illustrates the change in the color o the Nb solution caused by the reaction of click moieties with ainate aldehydes present in the oxidized alginate material.

FIG. 10 illustrates that, in contrast to the unoxidized alginate, oxidized VLVG material is soluble to at least 50% w/v.

FIG. 21b is a graph showing the release of $VEGF_{165}$ from click alginate hydrogels prepared using various alginate compositions.

DETAILED DESCRIPTION OF THE INVENTION

Figure 1A:
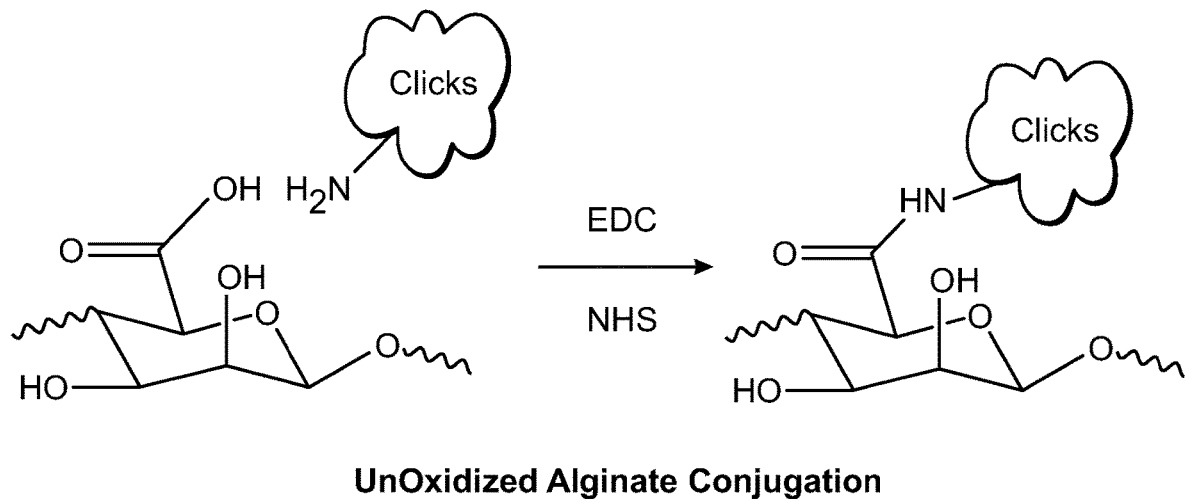
FIG. 1a is a schematic showing conjugation of click reagent to unoxidized alginate.

I. Reduced and Highly Oxidized Polysaccharides of the Invention

The present invention is directed to compositions comprising a reduced polysaccharide, wherein the reduced polysaccharide comprises less than 2% of residual aldehydes. The present invention is also directed to compositions comprising a reduced polysaccharide, wherein the reduced polysaccharide comprises less than 3% of residual aldehydes, and wherein the polysaccharide is produced by reacting a polysaccharide with a diol specific oxidizing agent, thereby producing an oxidized polysaccharide comprising 15% or more oxidation on a molar basis, followed by reacting the oxidized polysaccharide with a water soluble aldehyde specific reducing agent to produce the reduced polysaccharide.

The reduced polysaccharides comprised in the compositions of the invention may be used for preparing hydrogels. These polysaccharides are generated by a two-step process. The first step involves reacting a polysaccharide, e.g., an alginate, with a diol specific oxidizing agent to produce an aldehyde containing oxidized polysaccharide, e.g., an aldehyde containing oxidized alginate. The second step involves further reductive processing of the aldehyde containing oxidized polysaccharide to produce a reduced polysaccharide. The reduction process involves reducing the aldehyde moieties present in the oxidized polysaccharide to produce alcohol moieties. Accordingly, the term "reduced polysaccharides", as used herein, includes polysaccharides that comprise alcohol moieties. In some embodiments, the reduced polysaccharide is produced by oxidizing the polysaccharide using a diol specific oxidizing agent to produce an aldehyde containing polysaccharide; and then reductively processing the oxidized polysaccharide, e.g., by using a water soluble aldehyde specific reducing agent, to produce the reduced polysaccharide. In certain examples, a reduced polysaccharide comprises a monomeric subunit having a ring opened alcohol having the following structure:

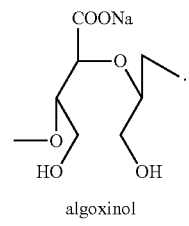

algoxinol

The term "polysaccharide", as used in this specification, refers to any polymeric carbohydrate molecule composed of chains of monosaccharide units bound together by glycosidic linkages. For example, alginate is a polysaccharide that comprises two different monomeric subunits, β-D-mannuronate (M) and its C-5 epimer α-L-guluronate (G), which are (1-4)-linked.

The polysaccharide chains may be linear or branched. The term "polysaccharide" is also intended to encompass an oligosaccharide. The polysaccharide can be a homopolysaccharide containing only monomer units of one kind (e.g., glucose), or a heteropolysaccharide, containing monomer units of different kinds (e.g., glucose and fructose). In one embodiment, the term "polysaccharide" refers to polymeric carbohydrate molecule that contains a diol, i.e., two hydroxyl groups present on adjacent carbons. Non-limiting examples of diol-containing polysaccharides include alginate, pullulan, scleroglucan, chitosan, elsinan, xanthan gum, dextran, mannose, gellan, levan, cellulose, hyaluronic acid, chondroitin sulfate A, chondroitin sulfate C, chondroitin sulfate E and β-d-glucans.

In one specific embodiment, the diol-containing polysaccharide is an alginate polymer. Alginate polymers are comprised of two different monomeric units, (1-4)-linked (3-D-mannuronic acid (M units) and a L-guluronic acid (G units) monomers, which can vary in proportion and sequential distribution along the polymer chain. Alginate polymers are polyelectrolyte systems which have a strong affinity for divalent cations (e.g., $Ca^{+2}$, $Mg^{+2}$, $Ba^{+2}$) and form stable hydrogels when exposed to these molecules. See Martinsen A., et al., Biotech. & Bioeng., 33 (1989) 79-89). For example, calcium cross-linked alginate hydrogels are useful for dental applications, wound dressings chondrocyte transplantation and as a matrix for other cell types. Without wishing to be bound by theory, it is believed that G units are preferentially crosslinked using calcium crosslinking, whereas click reaction based crosslinking is more indiscriminate with respect to G units or M units (i.e., both G and M units can be crosslinked by click chemistry).

The term "alginate", used interchangeably with the term "alginate polymers", includes unmodified alginate, oxidized alginate (e.g., comprising one or more algoxalate monomer units) and/or reduced alginate (e.g., comprising one or more algoxinol monomer units). In some embodiments, oxidized alginate comprises alginate comprising one or more aldehyde groups, or alginate comprising one or more carboxylate groups. In other embodiments, oxidized alginate comprises highly oxidized alginate, e.g., comprising one or more algoxalate units. Oxidized alginate may also comprise a relatively small number of aldehyde groups (e.g., less than 15%, e.g., 14,%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2% 0.1% or less aldehyde groups or oxidation on a molar basis). The term "alginate" or "alginate polymers" may also include alginate, e.g., unmodified alginate, oxidized alginate or reduced alginate, conjugated to at least one click reagent as described below.

The alginate polymers useful in the context of the present invention may have an average molecular weight from about 20 kDa to about 500 kDa, e.g., from about 20 kDa to about 40 kDa, from about 30 kDa to about 70 kDa, from about 50 kDa to about 150 kDa, from about 130 kDa to about 300 kDa, from about 230 kDa to about 400 kDa, from about 300 kDa to about 450 kDa, or from about 320 kDa to about 500 kDa. In one example, the alginate polymers useful in the present invention may have an average molecular weight of about 32 kDa. In another example, the alginate polymers useful in the present invention may have an average molecular weight of about 265 kDa. In some embodiments, the alginate polymer has a molecular weight of less than about 1000 kDa, e.g., less than about 900 Kda, less than about 800 kDa, less than about 700 kDa, less than about 600 kDa, less than about 500 kDa, less than about 400 kDa, less than about 300 kDa, less than about 200 kDa, less than about 100 kDa, less than about 50 kDa, less than about 40 kDa, less than about 30 kDa or less than about 25 kDa. In some embodiments, the alginate polymer has a molecular weight of about 1000 kDa, e.g., about 900 Kda, about 800 kDa, about 700 kDa, about 600 kDa, about 500 kDa, about 400 kDa, about 300 kDa, about 200 kDa, about 100 kDa, about 50 kDa, about 40 kDa, about 30 kDa or about 25 kDa. In one embodiment, the molecular weight of the alginate polymers is about 20 kDa.

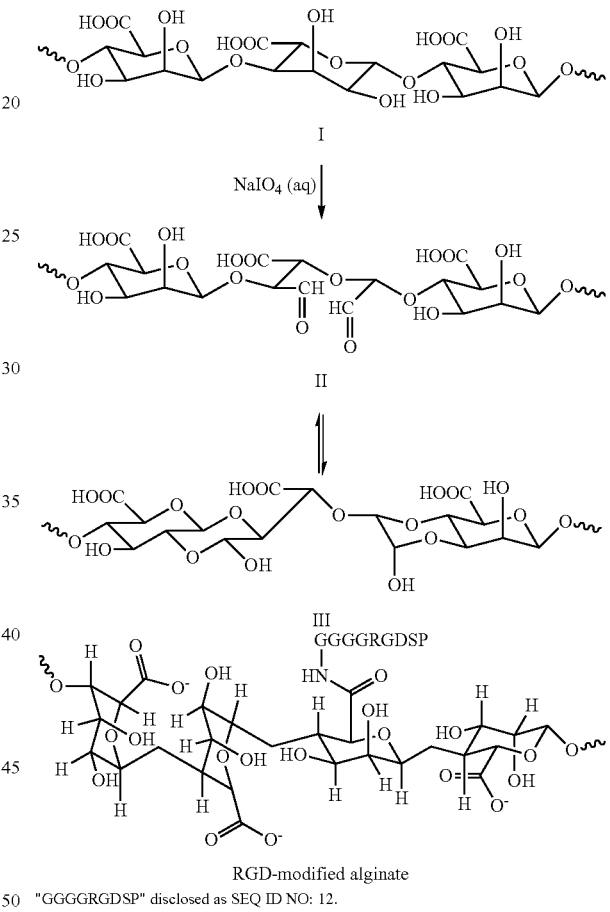

RGD-modified alginate
"GGGGRGDSP" disclosed as SEQ ID NO: 12.

A polysaccharide, e.g., a diol containing polysaccharide, such as an alginate, may be reacted in the first step with a diol specific oxidizing agent. The term "diol specific oxidizing agent" refers to an oxidizing agent that specifically reacts with a diol moiety, e.g., a diol moiety present in a polysaccharide, and does not oxidize other functional groups, e.g., alcohols, that may also be present in a polysaccharide. Non-limiting examples of diol specific oxidizing agents include sodium periodate ($NaIO_4$), periodic acid ($HIO_4$), lead tetraacetate ($PB(OAc)_4$), sodium paraperiodate ($Na_3H_2IO_6$) and potassium periodate ($KIO_4$). In a specific embodiment, the diol specific oxidizing agent is sodium periodate ($NaIO_4$).

The diol-specific oxidizing reagent reacts with a diol to cleave the carbon-carbon bond and to produce two aldehyde moieties. In certain embodiments, this reaction produces oxidized polysaccharides that are at least about 0.1%, 0.5%, 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99% or about 100% oxidized. Ranges intermediate to the recited values are also intended to be part of this invention. For example, in certain embodiments, this reaction may produce oxidized polysaccharides that are about 1% to about 5%, about 3% to about 10%, about 5% to about 20%, about 10% to about 15%, about 12% to about 25%, about 15% to about 30%, about 20% to about 25%, about 25% to about 45%, about 30% to about 50%, about 45% to about 60%, about 50% to about 70%, about 55% to about 75%, about 60% to about 80%, about 65% to about 80%, about 70% to about 90% or about 85% to about 100% oxidized.

The term "oxidized polysaccharide", e.g., "oxidized alginate", as used throughout this specification, refers to a polysaccharide that has been oxidized, e.g., reacted with an oxidizing agent, such as a diol specific oxidizing agent. An oxidized polysaccharide, e.g., an alginate, comprises aldehyde moieties which result from oxidation of the polysaccharide. An oxidized polysaccharide may be about 0.1% to about 100% oxidized, e.g., about 0.1% to about 5%, about 1% to about 10%, about 5% to about 20%, about 15% to about 40%, about 25% to about 60%, about 40% to about 70%, about 55% to about 90% or about 75% to about 100% oxidized. In some embodiments, the oxidized polysaccharide may be less than about 15% oxidized, e.g., less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, less than about 0.9%, less than about 0.8%, less than about 0.7%, less than about 0.6%, less than about 0.5%, less than about 0.4%, less than about 0.3%, less than about 0.2%, or less than about 0.1% oxidized.

The term "% oxidation" or "% oxidized", "oxidation level" or "% oxidation level", used interchangeably with the term "% oxidation on a molar basis", refers to % molar fraction of monomeric subunits in a diol containing polysaccharide, e.g., an alginate, that are ring opened as a result of oxidation. In some cases, the polysaccharide is a diol containing polysaccharide that has been subjected to a reaction with a diol specific oxidizing agent, such as sodium periodate. Methods that may be useful for measuring % oxidation of a polysaccharide are known to one of ordinary skill in the art and may include, e.g., qNMR.

For example, the term "% oxidation" may be used in reference to a polysaccharide that has been oxidized, e.g., by a diol specific oxidizing agent, and contains ring opened monomeric subunits comprising aldehyde moieties. One example of such monomeric subunit, e.g., in alginate, is shown below:

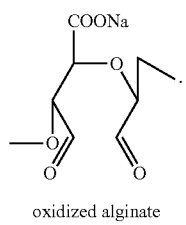

oxidized alginate

The term "% oxidation" may also be used in reference to a polysaccharide that has been oxidized, e.g., by a diol specific oxidizing agent, and has subsequently been reduced, e.g., by a water soluble aldehyde specific reducing agent, and contains ring opened monomeric subunits comprising alcohol moieties. One example of such monomeric subunit, e.g., algoxinol, is shown below:

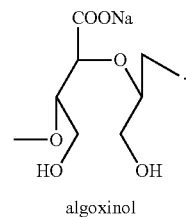

algoxinol

The term "% oxidation" may also be used in reference to a polysaccharide that has been oxidized, e.g., by a diol specific oxidizing agent, and has subsequently been further oxidized, e.g., by a second oxidizing agent, and contains ring opened monomeric subunits comprising carboxylic acid moieties. One example of such monomeric subunit, e.g., algoxalate, is shown below:

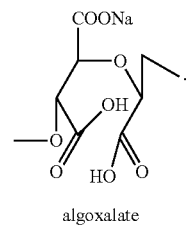

algoxalate

The term "% aldehydes", as used herein, refers to the % molar fraction of aldehydes present in ring opened monomeric subunits of a polysaccharide, e.g., a diol containing polysaccharide, e.g., an alginate.

The term "% residual oxidation", "residual oxidation level", "% residual oxidation level", "% residual oxidation on a molar basis" or "% residual aldehydes" refers to the % molar fraction of residual aldehydes, i.e., aldehyde moieties that remain in a polysaccharide after it has been reacted with a diol specific oxidizing agent and then reduced, e.g., with an aldehyde specific water soluble reducing agent, to produce reduced polysaccharide as described below. In some embodiments, the reduced polysaccharide, e.g., the reduced alginate, may comprise about 0.01% to about 3% residual aldehydes, e.g., about 0.01% to about 1%, about 0.05 to about 1.5% or about 1% to about 3% residual aldehydes. For example, the reduced polysaccharide may comprise about 2% residual aldehydes or about 3% residual aldehydes. This term may also refer to the % molar fraction of residual aldehydes, i.e., aldehyde moieties that remain in a polysaccharide after it has been reacted with a diol specific oxidizing agent and then further oxidized, e.g., with a second oxidizing agent, to produce highly oxidized polysaccharide as described below. In some embodiments, the highly oxidized polysaccharide, e.g., the highly oxidized alginate, may comprise about 0.01% to about 3% residual aldehydes, e.g., about 0.01% to about 1%, about 0.05 to about 1.5% or about 1% to about 3% residual aldehydes. For example, the highly oxidized polysaccharide may comprise about 2% residual aldehydes or about 3% residual aldehydes.

An exemplary reaction between a monomeric unit of a polysaccharide is the reaction between alginate and sodium periodate, a diol specific oxidizing agent, is illustrated in Scheme 1:

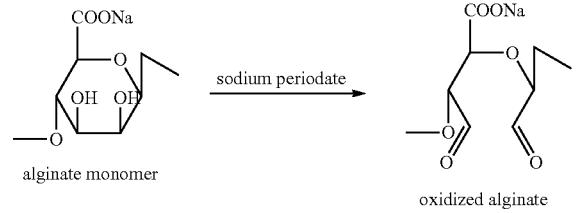

Scheme 1.

alginate monomer → sodium periodate → oxidized alginate

Further reductive processing of the aldehyde containing oxidized polysaccharides in the second step of the methods of the invention involves a reaction of the aldehyde containing oxidized polysaccharide with an aldehyde specific water soluble reducing agent. The term "aldehyde specific water soluble reducing agent" refers to a reducing agent that specifically oxidizes aldehydes, e.g., aldehydes present in a polysaccharide as a result of oxidation by a diol specific oxidizing agent, and converts them to alcohols. In certain embodiments, the aldehyde specific water soluble reagent is non-toxic and/or is a Green reagent. Non-limiting examples of aldehyde specific water soluble reducing agents include sodium borohydride ($NaBH_4$); sodium cyanoborohydride ($NaCNBH_3$); hydrogen gas ($H_2$) in the presence of a catalyst, e.g., a nickel (Ni), a platinum (Pl) or a palladium (Pd) catalyst; ammonia borane ($H_3NBH_3$); or a borane complex, e.g., a bis-carbonate borane complex ($[BH_3]_2CO_2]^{2-} \cdot 2Na^+$), a borane dimethylamine complex [$(CH_3)_2NH \cdot BH_3$]; a borane tert-butylamine complex [$(CH_3)_3CNH_2 \cdot BH_3$]; or a borane-pyrimidine complex. In a specific example, the aldehyde specific water soluble reducing agent is ammonia borane. In one embodiment, the aldehyde specific water soluble reducing agent is not sodium borohydride.

An exemplary reaction of the oxidized glucuronic acid, a product of the reaction illustrated in Scheme 1, with ammonia borane, a water soluble aldehyde specific reducing agent, is illustrated in Scheme 2.

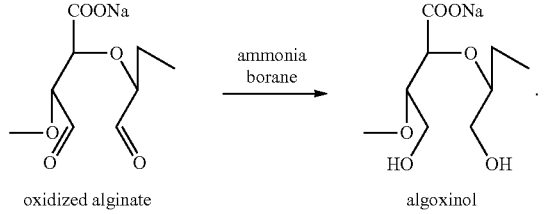

Scheme 2.

oxidized alginate → ammonia borane → algoxinol

In the context of the present invention, the term "residual aldehyde" refers to the aldehydes remaining in a reduced polysaccharide after the reduction of the oxidized polysaccharide, e.g., oxidized alginate, with an aldehyde specific water soluble reducing agent, e.g., ammonia borane, is completed. The amount of aldehydes present in a polysaccharide, e.g., the amount of residual aldehydes present in a polysaccharide after reduction with a water soluble aldehyde specific reducing agent, may be measured by any methods known to one of skill in the art. For example, the amount of residual aldehydes present in a polysaccharide may be measured by quantitative NMR, where the integral of alginate (1.5% w/v) aldehyde peaks (>5.1 ppm) are compared to an internal standard dimethylmalonic acid (2.5 mg/mL), and may be expressed as % of residual aldehydes.

It has been surprisingly discovered by the present inventors that water soluble aldehyde specific reducing agents, e.g., ammonia borane, are particularly effective at reducing aldehydes present in an oxidized polysaccharide, e.g., an alginate polymer, and converting them into alcohols. Accordingly, a reduced polysaccharide that has been obtained from subjecting an oxidized polysaccharide to further reductive processing via a reaction with a water soluble aldehyde specific reducing agent, e.g., ammonia borane, contains surprisingly low levels of residual aldehydes. In some embodiments, the reduced polysaccharide contains less than 2% of residual aldehydes, e.g., less than 1.5%, less than 1% or less than 0.5% of residual aldehydes. In other embodiments, the reduced polysaccharide contains less than 3% of residual aldehydes, e.g., less than 3%, less than 2.5%, less than 2%, less than 1.5%, less than 1%, or less than 0.5% of residual aldehydes.

It is desirable to have a low level of aldehydes in a polysaccharide, e.g., an alginate, used to prepare a hydrogel, because aldehydes can cause damage to proteins and other molecules present in the vicinity of the polysaccharide, thereby increasing the toxicity of the hydrogel. Additionally, the use of water soluble aldehyde specific reducing agents is particularly advantageous because these reagents do not produce toxic by-products and do not necessitate further processing of the polysaccharide materials. The water soluble aldehyde specific reducing agents, e.g., ammonia borane, are also non-toxic and/or are considered to be "Green Reagents".

The present invention also utilizes highly oxidized polysaccharides, e.g., highly oxidized alginate polymers. These highly charged oxidized polysaccharides are more soluble in water than oxidized polysaccharides, making their manipulation simpler. The highly oxidized polysaccharides may be prepared in two steps. The first step involves reacting a polysaccharide, e.g., an alginate polymer, with a diol specific oxidizing agent to produce an aldehyde containing oxidized polysaccharide, e.g., an aldehyde containing oxidized alginate polymer, as described above. The second step involves further oxidative processing of the aldehyde containing oxidized polysaccharide to produce a highly oxidized polysaccharide. The further oxidative processing of the oxidized polysaccharide involves converting the aldehyde moieties present in the oxidized polysaccharide into carboxylic acid moieties. Accordingly, the term "highly oxidized polysaccharide", as used herein, includes polysaccharides that comprise at least one, e.g., two additional carboxylic acid moieties per monomeric subunit. For example, a highly oxidized polysaccharide may comprise a monomeric subunit which is a ring opened carboxylic acid containing alginate, or algoxalate, having the following structure:

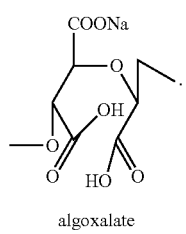

algoxalate

The further oxidative processing of the aldehyde containing oxidized polysaccharide, e.g., an alginate polymer, involves a reaction of the aldehyde containing oxidized polysaccharide with a second oxidizing agent. The term "second oxidizing agent", as used in this specification, refers to any oxidizing agent that specifically converts an aldehyde moiety into a carboxylic acid moiety, thereby producing a highly oxidized polysaccharide. Non-limiting examples of the second oxidizing agents include sodium chlorite; bromine; dilute nitric acid ($NHO_3$); silver oxide, e.g., Tollens' Reagent ($[Ag(NH_3)_2]^+$ or $AgNO_3$); copper(II) complexes, e.g., Fehling's reagent (copper (II) tartrate solution), or Benedict's reagent (copper (II) citrate solution); potassium permanganate ($KMnO_4$); and hydrogen peroxide ($H_2O_2$). In a specific embodiment, the second oxidizing agent is sodium chlorite.

An exemplary reaction of the oxidized monomeric unit of a polysaccharide is the reaction of oxidized alginate, a product of the reaction illustrated in Scheme 1, with sodium chlorite, a second oxidizing agent, is illustrated in Scheme 3.

Scheme 3.

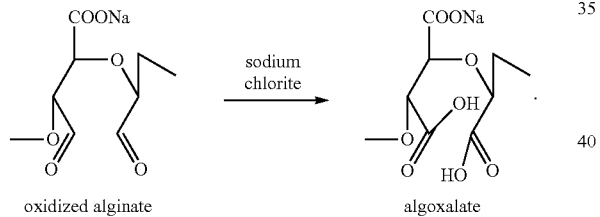

oxidized alginate → algoxalate

It has been surprisingly discovered that both reduced polysaccharides, e.g., reduced polysaccharides resulting from the reaction of oxidized polysaccharides with water soluble aldehyde specific reducing agents (e.g., ammonia borane), such as polysaccharides comprising algoxinol, as well as highly oxidized polysaccharides, e.g., the polysaccharides resulting from the reaction of oxidized polysaccharides with a second oxidizing agent, such as polysaccharides comprising algoxalate, are particularly useful for preparing hydrogels. The hydrogels prepared from reduced and highly oxidized polysaccharides, e.g., reduced and highly oxidized alginate polymers, are biodegradable and useful as drug delivery vehicles.

In some embodiments, the solubility of reduced and/or highly oxidized polysaccharide, e.g., reduced and/or highly oxidized alginate, such as alginate comprising algoxinol and/or algoxalate, is higher than the solubility of unmodified alginate. The solubility of a polysaccharide, such as a reduced and/or a highly oxidized polysaccharide, may be expressed as % w/v or in mg/mL, wherein 1% w/v is equivalent to 10 mg/mL of the polysaccharide. For example, the solubility of reduced and/or highly oxidized polysaccharide may be about 10-20% w/v, 15-30% w/v, 20-40% w/v, 30-50% w/v, 40-65% w/v, 50-75% w/v or 60-90% w/v. For example, the solubility of the reduced and/or highly oxidized polysaccharide of the invention may be about 10% w/v, about 15% w/v, about 20%, about 25% w/v, about 30% w/v, about 35% w/v, about 40% w/v, about 45% w/v, about 50% w/v, about 55% w/v, about 60% w/v, about 65% w/v, about 70% w/v, about 75% w/v, about 80% w/v or about 90% w/v.

In some embodiments, the polysaccharides of the invention are biodegradable. For example, oxidized, reduced and highly oxidized alginate is biodegradable. Alginate, e.g., oxidized, reduced and highly oxidized alginate, is not susceptible to degradation by a host endogenous enzyme, e.g., an endogenous enzyme that may be present in a human. Alginate, e.g., oxidized, reduced and highly oxidized alginate, may be chemically degraded, e.g., hydrolyzed when exposed to acidic or alkaline condition. Acidic conditions comprising a pH of 6.5 or lower, while alkaline conditions comprise a pH of 8 or higher.

II. Polysaccharides of the Invention Conjugated to Click Reagents

The reduced and highly oxidized polysaccharides of the invention, e.g., alginate, may be conjugated with a click reagent. The term "click reagent", used in this specification interchangeably with the term "click chemistry reagent" is a reagent that can rapidly and selectively react ("click") with its counterpart click reagent under mild conditions in aqueous solution. The mild conditions include neutral pH, aqueous solution and ambient temperature, with low reactant concentrations. Exemplary click pair reagents are well known to one of skill in the art and include, but are not limited to, azide and dibenzocyclooctyne (DBCO), tetrazine and transcyclooctene, and tetrazine and norbornene, with the structures illustrated below.

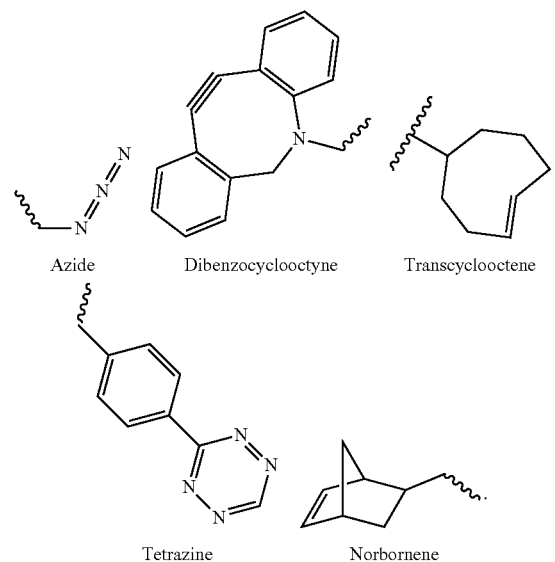

Azide  Dibenzocyclooctyne  Transcyclooctene

Tetrazine  Norbornene

In some embodiments, the click reagent is tetrazine (Tz). As used herein, the terms "tetrazine" and "tetrazine moiety" include molecules that comprise 1,2,4,5-tetrazine substituted with suitable spacer for linking to the polymer (e.g., alkylamines like methylamine or pentylamine), and optionally further substituted with one or more substituents at any available position. Exemplary tetrazine moieties suitable for the compositions and methods of the disclosure include, but are not limited to, the structures shown below (see, e.g., Karver et al., (2011) *Bioconjugate Chem.* 22:2263-2270, and WO 2014/065860, the entire contents of each of which are hereby incorporated herein by reference):

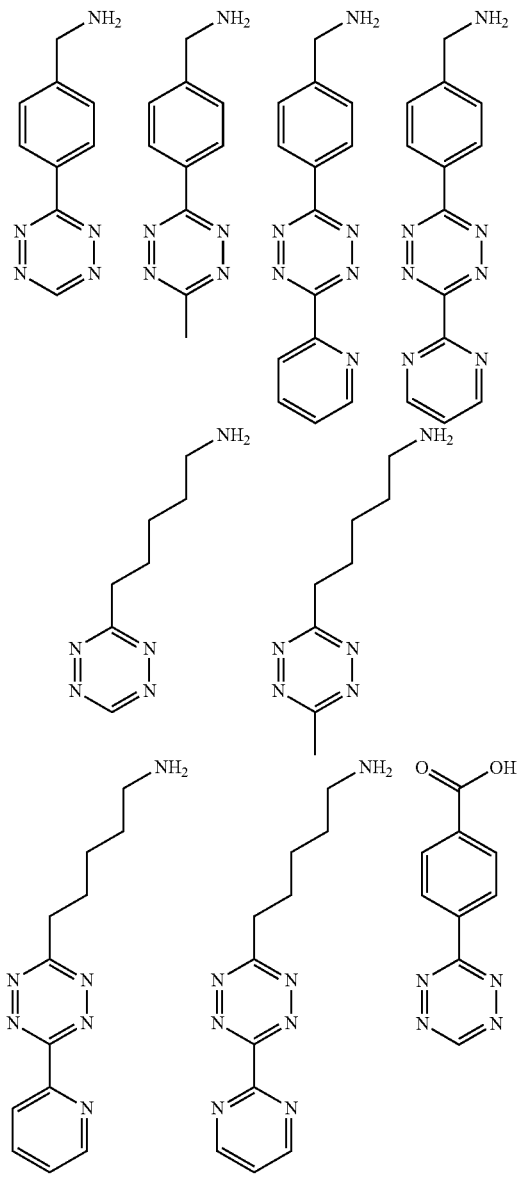

One of the counterpart reagents for tetrazine is norbornene (Nb). As used herein, the terms "norbornene" and "norbornene moieties" include but are not limited to norbornadiene and norbornene groups further comprising suitable spacer for linking to the polysaccharide (e.g., alkylamines like methylamine or pentylamine), and optionally further substituted with one or more substituents at any available position. Such moieties include, for example, norbornene-5-methylamine and norbornadienemethylamine.

Figure 1B:
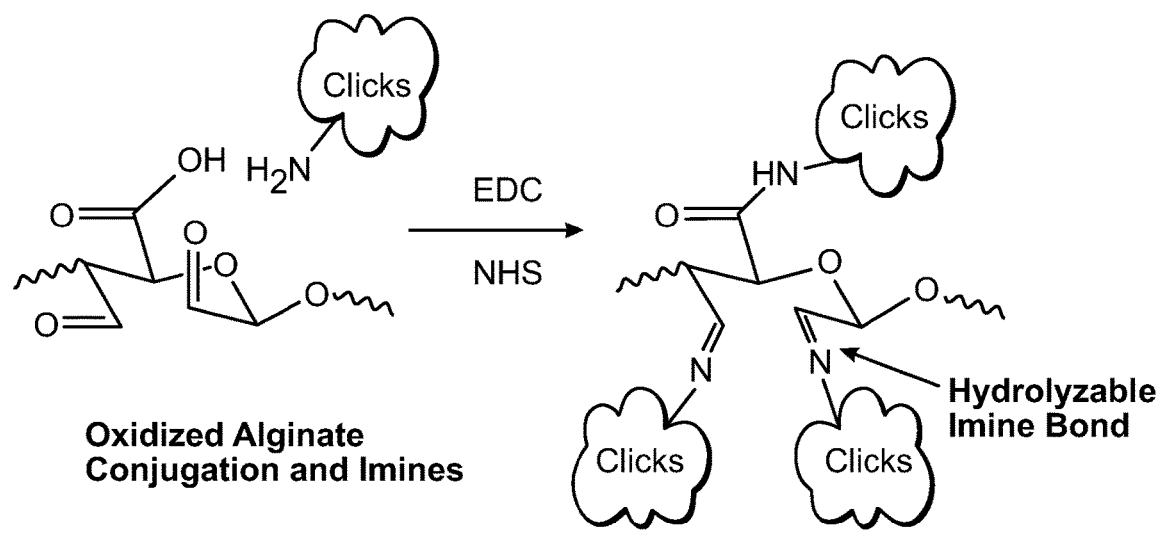
FIG. 1b is a schematic showing conjugation of click reagent to oxidized alginate, illustrating the formation of an unstable (hydrolyzable) imine bond, which is detrimental to further covalent click cross-linking.
Figure 1C:
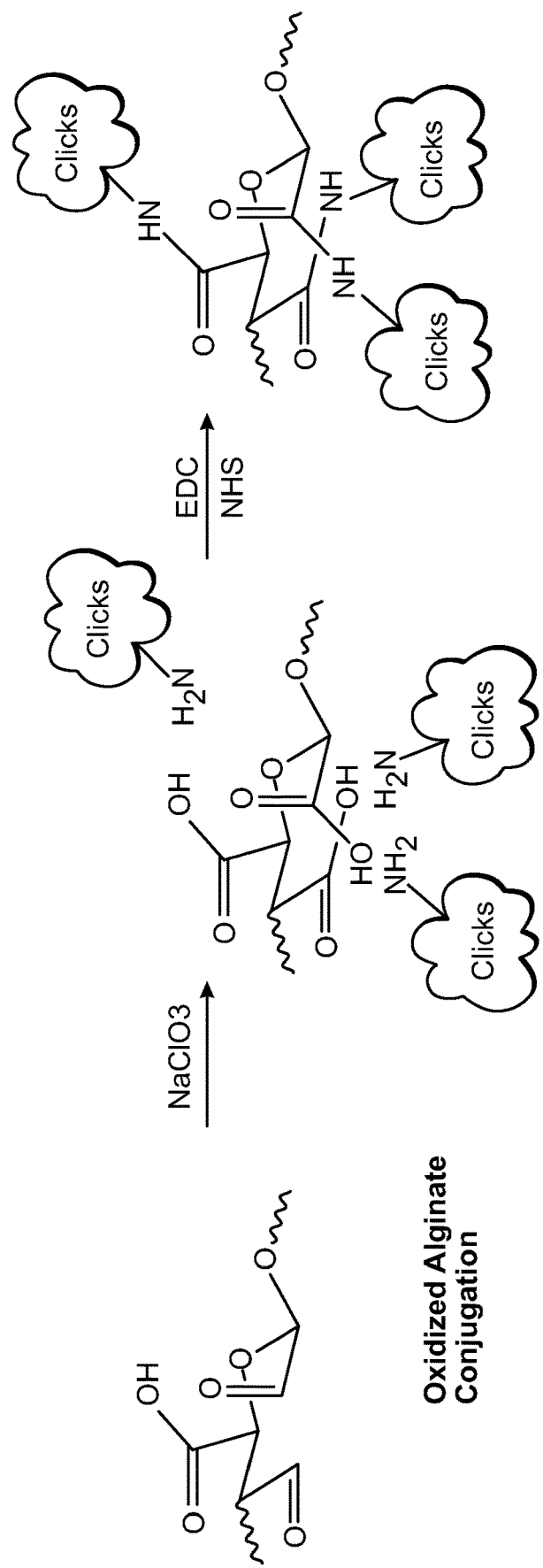
FIG. 1c is a schematic showing conjugation of click reagent to highly oxidized alginate, illustrating the additional carboxylic acid groups produced that are available for click conjugation.

Click reagents are typically conjugated to a polysaccharide, e.g., an alginate, via the carboxylic moiety. In one specific example illustrated in FIG. 1a, click reagents may be conjugated to alginate polymers via the carboxylate moiety present in the glucuronic acid in an alginate. Accordingly, one click molecule may be conjugated per glucuronate in an unprocessed alginate. Following oxidation of alginate with sodium periodate, two aldehydes per glucuronate are generated. Each aldehyde moiety may become conjugated to a click reagent via an imine bond (FIG. 1b). This conjugation of click reagents to oxidized alginates is sub-optimal because of residual aldehydes that remain in the alginate following conjugation that may result in toxicity and damage to cargo, as well as in degradation of the click reagents (see also Examples 1 and 3). Further, the imine bonds between the aldehydes and the click reagents are easily hydrolyzable, resulting in the loss of click reagents from the alginate. As shown in FIG. 1c, further oxidation of aldehydes present in oxidized alginates converts these aldehydes into carboxylic acids thereby providing two additional sites for click conjugation.

It has been surprisingly discovered that certain highly oxidized polysaccharides, e.g., highly oxidized alginate polymers, are better substrates for click reagent conjugation than oxidized polysaccharides because they contain additional sites available for click conjugation. It has also been discovered that reduced polysaccharides, e.g., reduced alginates, are better suited for click reagent conjugation than oxidized polysaccharides because they contain a lower amount of aldehydes that can react with click reagents, causing their degradation.

In some embodiments, the click reagent conjugated to a polysaccharide of the invention, e.g., an alginate, may also react with its counterpart click reagent that is, in turn, attached to a moiety, thereby conjugating the moiety to the polysaccharide. Any moiety may be conjugated to the polysaccharide of the invention using the click reagents. Non-limiting examples of such moieties include a small organic molecule, a small inorganic molecule; a saccharine; a monosaccharide; a disaccharide; a trisaccharide; an oligosaccharide; a polysaccharide; a peptide; a protein, a peptide analog, a peptide derivative; a peptidomimetic; an antibody (polyclonal or monoclonal); an antigen binding fragment of an antibody; a nucleic acid, e.g., an oligonucleotide, an antisense oligonucleotide, siRNAs, shRNAs, a ribozyme, an aptamer, microRNAs, pre-microRNAs, iRNAs, plasmid DNA (e.g. a condensed plasmid DNA), a modified RNA, and a nucleic acid analog or derivative. In some embodiments, the moiety is a therapeutic agent.

In other embodiments, a click reagent conjugated to a polysaccharide of the invention, e.g., an alginate, may function as a cross-linking agent, as described in detail below.

In certain embodiments, a polysaccharide of the invention, e.g., an alginate, may be conjugated to two or more click reagents, that belong to different click pairs. For example, in an embodiment where the polysaccharide of the invention is conjugated to two click reagents belonging to two different click pairs, a first click reagent conjugated to the polysaccharide may be azide from the azide-dibenzocyclooctyne (azide-DBCO) click pair, and a second click reagent conjugated to the polysaccharide may be tetrazine from the tetrazine-norbornene click pair. In such polysaccharides, the two click reagents may be used for different functions. For example, the first click reagent may function to promote cross-linking of the polysaccharide to form a hydrogel, and the second cross-linking reagent may function to conjugate a moiety to the polysaccharide, as described above. In a specific embodiment, when a polysaccharide of the invention is conjugated to two or more click reagents, the click reagents conjugated to the polysaccharide do not cross-react, i.e., do not react with each other, but only react with their click pairs.

III. Polysaccharides of the Invention Conjugated to Cross-Linking Agents

The reduced and highly oxidized polysaccharides of the invention may be conjugated with a cross-linking agent. The cross-linking agent may be attached to the oxidized polysaccharide ionically, covalently or physically. In one embodiment, the cross-linking agent is covalently or non-covalently attached to the reduced polysaccharide of the invention, e.g., a reduced alginate polymer. In another embodiment, the cross-linking agent is covalently or non-covalently attached to the highly oxidized polysaccharide of the invention, e.g., a highly oxidized alginate polymer.

The term "cross-linking agent", as used in this specification, is any agent that may effect and promote cross-linking of the polysaccharide to a specific location, e.g., a location inside a cell or a tissue of a subject, or that may promote cross-linking of a polysaccharide, e.g., an alginate polymer. In certain embodiments, the cross-linking agent is attached to the polysaccharide, e.g., via a covalent bond. In certain embodiments, the cross-linking agent is only coupled to one polymer chain and functions as a pendant group.

In some embodiments, the cross-linking agent is a click reagent. Exemplary pairs of click reagents that may be used for cross-linking the polysaccharide of the invention include, but are not limited to, azide and dibenzocyclooctyne (DBCO), tetrazine and trancyclooctene, and tetrazine and norbornene, with structures as illustrated above.

The reduced and/or highly oxidized polysaccharide of the invention modified with a click reagent, e.g., an alginate conjugated to a click reagent, can be covalently cross-linked to form a click-crosslinked hydrogel, e.g., a click alginate hydrogel. Formation of hydrogels via click chemistry is described in Desai et al. (2015) *Biomaterials* 50:30-37, the entire contents of which are hereby incorporated herein by reference. The cross-linking reaction has been previously shown by others to be highly specific, bio-orthogonal, and quick (see, e.g., Devaraj et al. (2008), *Bioconjugate Chem.* 19(12):2297-2299; Karver et al. (2011) *Bioconjugate Chem.* 22(11):2263-2270; and Alge et al. (2013) *Biomacromol.* 14(4):949-953), allowing for incorporation of cells with high post-encapsulation viability.

For example, to generate a hydrogel from a click-conjugated polysaccharide of the invention, e.g., a click conjugated alginate, e.g., comprising algoxinol and/or algoxalate, a polysaccharide conjugated to one member of a click pair, e.g., Nb may be mixed with a polysaccharide conjugated to the second member of a click pair, e.g., Tz and incubated at mild conditions to generate the hydrogel. Properties of such hydrogels, e.g., stiffness of the hydrogel, the time to gelation, or an average pore size of the hydrogel, may be modulated by varying a number of parameters that include the degree of click conjugation of the polysaccharide; the degree of polysaccharide oxidation, i.e., % residual aldehydes present in the polysaccharide; and the concentration of click conjugated polysaccharide during hydrogel formation, e.g., % w/v/of the alginate material present in the solution immediately prior to formation of the hydrogel.

The term "degree of click conjugation", which may be used interchangeably with the term "degree of substitution" or "DS" refers to the average number of click reagents per monomeric unit of a polysaccharide, e.g., the average number of click reagents per monomer units in an alginate. The degree of click substitution may be varied by varying the number of molar equivalents of click reagent to the moles of alginate monomers in the click conjugation reaction. For example, the click conjugation reaction may comprise about 1 to about 5000 molar equivalents of a click reagent, e.g., about 1, about 5, about 10, about 20, about 50, about 100, about 150, about 200, about 250, about 300, about 350, about 400, about 450, about 500, about 550, about 600, about 650, about 700, about 750, about 800, about 850, about 900, about 950, about 1000, about 1200, about 1500, about 1800, about 2000, about 2200, about 2500, about 2800, about 3000, about 3200, about 3500, about 4000, about 4200, about 4500 or about 5000 molar equivalents of the click reagent. Ranges intermediate to the recited values are also intended to be part of this invention. For example, the click conjugation reaction may comprise about 1 to about 50, about 10 to about 100, about 150 to about 250, about 200 to about 500, about 400 to about 800, about 700 to about 1000, about 1200 to about 1600, about 1500 to about 2000, about 1800 to about 3500, or about 3200 to about 5000 molar equivalents of a click reagent.

In some embodiments, the polysaccharide of the invention conjugated to a click reagent comprises a degree of click substitution that is about 0.01% to about 100%, e.g., about 0.01% to about 0.5%, about 0.1% to about 5%, about 1% to about 10%, about 5% to about 15%, about 10% to about 20%, about 15% to about 25%, about 20% to about 35%, about 30% to about 40%, about 35% to about 50%, about 40% to about 60%, about 50% to about 75%, about 70% to about 90% or about 85% to about 100%. For example, the polysaccharide of the invention conjugated to a click reagent may be about 0.01%, about 0.05%, about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100%.

In some embodiments, the concentration of click conjugated polysaccharide during hydrogel formation, e.g., concentration of the alginate material present in the solution immediately prior to formation of the hydrogel, may be from about 0.01% to about 50% w/v, e.g., about 0.01% to about 10% w/v, about 0.1% to about 5% w/v, about 1% to about 15% w/v, about 10% to about 30% w/v, about 12% to about 35% w/v, about 15% to about 25% w/v, about 20% to about 45% w/v or about 35% to about 50% w/v. For example, the concentration of the alginate material present in the solution immediately prior to formation of the hydrogel may be about 0.01%, about 0.05%, about 1%, about 0.5%, about 1%, about 2%, about 3%, about 4%, about 5%, about 10%, about 15%, about 20%, about 25%, about 30%, about 35%, about 40%, about 45% or about 50%.

Stiffness of the hydrogel may depend on the degree of click substitution and may be determined by measuring an elastic modulus (or a storage modulus) G'. For example, G' of a hydrogel of the invention may vary from about 0 to about 40000 Pa when measured at 1% strain at 1 Hz, e.g., about 0 to about 100 Pa, about 50 to about 300 Pa, about 100 to about 450 Pa, about 130 to about 600 Pa, about 300 to about 450 Pa, about 500 to about 900 Pa, about 600 to about 1500 Pa, about 1200 to about 2000 Pa, or about 1900 to about 40000 Pa. For example, G' of a hydrogel of the invention when measured at 1% strain at 1 Hz, may be about 100 Pa, about 200 Pa, about 500 Pa, about 1000 Pa, about 1500 Pa, about 2000 Pa, about 2200 Pa, about 2500 Pa or about 3000 Pa.

In some embodiments, the cross-linking agent is a peptide, e.g., a cell adhesive peptide. Accordingly, a reduced and/or highly oxidized polysaccharide of the invention, e.g., a reduced and/or highly oxidized alginate polymer, may be modified by a cell adhesive peptide, e.g., an extracellular cell matrix (ECM) component. The cell adhesive peptide can comprise, for example, the amino acid sequence arginine-glycine-aspartate (RGD). Examples include the amino acid sequence arginine-glycine-aspartate-cysteine (RGDC) (SEQ ID NO: 1) and arginine-glycine-aspartate-serine (RGDS) (SEQ ID NO: 2). In other examples, the cell adhesive peptide comprises the amino acid sequence of lysine-glutamine-alanine-glycine-aspartate-valine (KQAGDV) (SEQ ID NO: 3) or valine-alanine-proline-glycine (VAPG) (SEQ ID NO: 4). In some examples, the cell adhesive peptide is CGGGGRGDSP (SEQ ID NO: 5). Other cell adhesive peptides may be used based on the desired application and will be apparent to one of skill in the art.

In some cases, the cell adhesive peptide is covalently linked to the reduced and/or highly oxidized polysaccharide via a thiol-ene reaction, e.g., via thiol-ene photochemistry. For example, the cell adhesive peptide can be covalently linked to the polysaccharide (e.g., an alginate polymer) prior to or following crosslinking of the polysaccharide to form a hydrogel. Such use of thiol-ene reaction to covalently link the cell adhesive peptide to the polysaccharide is significantly faster and more efficient than the previously disclosed methods, such as methods using of carboxyl activating agents (e.g., EDC) to couple the peptide to the polymer.

IV. Hydrogels of the Invention

The reduced and/or highly oxidized polysaccharides described herein may be used to prepare hydrogels for therapeutic applications. The hydrogels prepared from the reduced and/or highly oxidized polysaccharides, e.g., reduced and/or highly oxidized alginates, are biodegradable and non-toxic, as compared to the hydrogels prepared from the oxidized polysaccharides, e.g., oxidized alginates. In some embodiments, when the hydrogels prepared using the reduced and/or highly oxidized polysaccharides of the invention encapsulate a cell, less cell toxicity is observed, as compared to the hydrogel prepared from the oxidized polysaccharides. In other embodiments, in which the hydrogels produced from the reduced and/or highly oxidized polysaccharides of the invention are used to encapsulate a therapeutic agent, e.g., a protein, less protein damage is observed, as compared to hydrogel prepared from oxidized polysaccharides. In embodiments, in which the hydrogels produced from the reduced and/or highly oxidized polysaccharides of the invention are used to encapsulate a lipid based nanoparticle, e.g., a liposome or a virosome, the lipid based nanoparticle is delivered intact to a desired location within a host.

The hydrogels of the invention may be used to prepare a dosage form comprising a therapeutic or a diagnostic agent encapsulated by the hydrogels of the invention. The hydrogels of the invention may also be used to prepare an implantable device which may comprise a therapeutic or a diagnostic agent. The hydrogels of the invention may also be used to prepare a drug delivery composition comprising a lipid based nanoparticle, e.g., a liposome or a virosome encapsulating a therapeutic or a diagnostic agent and the hydrogel of the invention encapsulating the lipid based nanoparticle.

It has been presently discovered that the reduced and/or highly oxidized polysaccharides of the invention are useful for preparing hydrogels in which an average mesh size, measured as an average diameter of the pores, varies over a relatively wide range. For example, the hydrogels prepared using the reduced and/or highly oxidized polysaccharides of the invention may have pores with an average diameter ranging from about 0.5 nm to about 500 nm, e.g., about 0.5 nm to about 1 nm, about 0.5 nm to about 5 nm, about 1 nm to about 20 nm, about 10 nm to about 50 nm, about 25 nm to about 80 nm, about 50 nm to about 100 nm, about 70 nm to about 150 nm, about 100 nm to about 250 nm, about 200 nm to about 350 nm, about 250 nm to about 400 nm or about 350 nm to about 500 nm. In some embodiments, the hydrogels of the invention may have pores with an average diameter of about 0.5 nm, about 1 nm, about 5 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 150 nm, about 200 nm, about 250 nm, about 300 nm, about 350 nm, about 400 nm, about 450 nm or about 500 nm. Ranges intermediate to the recited values are also intended to be part of this invention.

In one example, the hydrogels of the invention have a surprisingly small average pore size, e.g., an average diameter of about 10 nm or less. In some embodiments, the diameter of the pore in a hydrogel of the invention is about 10.00 nm or less, about 9.5 nm or less, about 9.0 nm or less, about 8.5 nm or less, about 8.0 nm or less, about 7.5 nm or less, about 7.0 nm or less, about 6.5 nm or less, about 6.0 nm or less, about 5.5 nm or less, about 5.0 nm or less, about 4.5 nm or less, about 4.0 nm or less, about 3.5 nm or less, about 3.0 nm or less, about 2.5 nm or less, about 2.0 nm or less, about 1.5 nm or less or about 1 nm or less. For example, the hydrogel of the invention may comprise pores having an average diameter of about 10 nm to about 1 nm, about 10 nm to about 4 nm, about 7 nm to about 3 nm, about 5 nm to about 1 nm, about 4 nm to about 2 nm, or about 3 nm to about 0.5 nm. Ranges intermediate to the recited values are also intended to be part of this invention.

Accordingly, the hydrogels of the invention may be used to encapsulate a therapeutic or diagnostic agent, or to encapsulate a lipid based nanoparticle, e.g., a liposome or a virosome comprising a therapeutic or diagnostic agent, of a small molecular weight. For example, the hydrogels of the invention may be used to encapsulate therapeutic or diagnostic agents, or a lipid based nanoparticle, e.g., a liposome or a virosome, encapsulating therapeutic or diagnostic agents, e.g., polypeptides, having a molecular weight of 1000 kDa or less, e.g., 950 kDa or less, 900 kDa or less, 850 kDa or less, 800 kDa or less, 750 kDa or less, 700 kDa or less, 650 kDa or less, 600 kDa or less, 550 kDa or less, 500 kDa or less, 450 kDa or less, 400 kDa or less, 350 kDa or less, 300 kDa or less, 250 kDa or less, 200 kDa or less, 150 kDa or less, 100 kDa or less, 90 kDa or less, 80 kDa or less, 70 kDa or less, 60 kDa or less, 50 kDa or less, 40 kDa or less, 30 kDa or less, 20 kDa or less, 10 kDa or less, 8 kDa or less, 6 kDa or less, 4 kDa or less, 2 kDa or less, 1 kDa or less, 0.8 kDa or less, 0.6 kDa or less, 0.4 kDa or less, 0.2 kDa or less, or 0.1 kDa or less.

In some embodiments, a therapeutic or diagnostic agent that may be encapsulated by the hydrogel of the invention, or by a lipid based nanoparticle, e.g., a liposome or a virosome, encapsulated by the hydrogel of the invention, does not diffuse through the pores of the hydrogel because the pores of the hydrogel are sufficiently small as compared to the size of the therapeutic agent. Accordingly, the release of the therapeutic agent from the hydrogel occurs gradually upon biodegradation of the hydrogel inside a subject. This provides sustained release of the therapeutic or diagnostic agent, or a lipid based nanoparticle, e.g., a liposome or a virosome, encapsulating the therapeutic or diagnostic agent, in the subject, e.g., a human.

As used herein, the term "therapeutic or diagnostic agent" that is encapsulated by the hydrogels of the invention, includes any agent that may be used to treat, prevent or diagnose a disorder in a subject in need thereof. A therapeutic or diagnostic agent may be a cell, e.g., a mammalian cell, such as a human mesenchymal stem cell (hMSC), a small molecule or a biologic. The biologic may be a peptide, a protein, a DNA molecule, an RNA molecule, a PNA molecule, an antibody or a vaccine. Exemplary therapeutic agents include, but are not limited to, those found in *Harrison's Principles of Internal Medicine,* 13$^{th}$ Edition, Eds. T. R. Harrison et al. McGraw-Hill N.Y., NY; Physicians' Desk Reference, 50$^{th}$ Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the entire contents of all of which are incorporated herein by reference.

In some embodiments, a therapeutic or diagnostic agent encapsulated by the hydrogel of the invention, or by a lipid based nanoparticle, e.g., a liposome or a virosome, encapsulated by the hydrogel of the invention, may comprise a compound selected from the group consisting of a small organic molecule, a small inorganic molecule; a saccharine; a monosaccharide; a disaccharide; a trisaccharide; an oligosaccharide; a polysaccharide; a peptide; a protein; a peptide analog; a peptide derivative; a peptidomimetic; an antibody (polyclonal or monoclonal); an antigen binding fragment of an antibody; a nucleic acid, e.g., an oligonucleotide, an antisense oligonucleotide, siRNAs, shRNAs, a ribozyme, an aptamer, microRNAs, a pre-microRNAs, iRNAs, plasmid DNA (e.g. a condensed plasmid DNA), modified RNA, a nucleic acid analog or derivative; an extract made from biological materials such as bacteria, plants, fungi, or animal cells; animal tissues; naturally occurring or synthetic compositions; and any combinations thereof. The nucleic acid may comprise one or more unnatural nucleotides. The peptide or the protein may comprise one or more unnatural amino acids.

As used herein, the term "small molecule" can refer to a compound that is "natural product-like," however, the term "small molecule" is not limited to "natural product-like" compounds. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases, it is preferred that a small molecule have a molecular mass equal to or less than 700 Daltons.

As used herein, the term "peptide" is used in its broadest sense to refer to compounds containing amino acids, amino acid equivalents or other non-amino groups, while still retaining the desired functional activity of a peptide. Peptide equivalents can differ from conventional peptides by the replacement of one or more amino acids with related organic acids (such as PABA), amino acids or the like or the substitution or modification of side chains or functional groups. The peptides can be linear or cyclic. A peptide can be modified to include one or more of D-amino acids, beta-amino acids, chemically modified amino acids, naturally occurring non-proteogenic amino acids, rare amino acids, and chemically synthesized compounds that have properties known in the art to be characteristic of an amino acid.

As used herein, the term "nucleic acid" or "oligonucleotide" means at least two nucleotides, including analogs or derivatives thereof, that are covalently linked together. Exemplary oligonucleotides include, but are not limited to, single-stranded and double-stranded siRNAs and other RNA interference reagents (RNAi agents or iRNA agents), shRNA (short hairpin RNAs), antisense oligonucleotides, aptamers, ribozymes, and microRNAs (miRNAs). The nucleic acids can be single stranded or double stranded. The nucleic acid can be DNA, RNA or a hybrid, where the nucleic acid contains any combination of deoxyribo- and ribo-nucleotides, and any combination of uracil, adenine, thymine, cytosine and guanine. An RNA molecule may be selected from the group consisting of an mRNA, an RNAi, an siRNA, an shRNA, a microRNA, an isRNA, a lncRNA and an antisense RNA.

The nucleic acid may also include one or more unnatural nucleotides. For example, the nucleic acid can comprise one or more nucleic acid modifications known in the art. For example, the nucleic acids can comprise one or more backbone modifications, e.g., phosphoramide (Beaucage et al., *Tetrahedron* 49(10):1925 (1993) and references therein; Letsinger, *J. Org. Chem.* 35:3800 (1970)), phosphorothioate, phosphorodithioate, O-methylphophoroamidite linkages (see Eckstein, Oligonucleotides and Analogues: A Practical Approach, Oxford University Press), or peptide nucleic acid linkages (see Egholm, *J. Am. Chem. Soc.* 114:1895 (1992); Meier et al., *Chem. Int. Ed. Engl.* 31:1008 (1992); and Nielsen, *Nature,* 365:566 (1993), the entire contents of all of which are herein incorporated by reference. The nucleic acids can also include modifications to nucleobase and/or sugar moieties of nucleotides. Exemplary sugar modifications at the sugar moiety include replacement of 2'-OH with halogens (e.g., fluoro), O-methyl, O-methoxyethyl, $NH_2$, SH and S-methyl.

In some embodiments, the term "therapeutic or diagnostic agent" comprises biological material, for example, an extracellular matrix material such as fibronectin, vitronection and laminin; a cytokines; a growth factor; a differentiation factor, a nucleic acid; a protein; a peptide; an antibody or a fragment thereof or an antigen binding portion thereof, or a cell.

Suitable growth factors and cytokines that may be incorporated into the hydrogels of the invention include, but are not limited, to stem cell factor (SCF), granulocyte-colony stimulating factor (G-CSF), granulocyte-macrophage stimulating factor (GM-CSF), stromal cell-derived factor-1, steel factor, VEGF, TGFβ, platelet derived growth factor (PDGF), angiopoeitins (Ang), epidermal growth factor (EGF), bFGF, HNF, NGF, bone morphogenic protein (BMP), fibroblast growth factor (FGF), hepatocye growth factor, insulin-like growth factor (IGF-1), interleukin (IL)-3, IL-1α, IL-1β, IL-6, IL-7, IL-8, IL-11, and IL-13, colony-stimulating factors, thrombopoietin, erythropoietin, fit3-ligand, and tumor necrosis factor α (TNFα). Other examples are described in Dijke et al., "Growth Factors for Wound Healing", *Bio/Technology,* 7:793-798 (1989); Mulder G D, Haberer P A, Jeter K F, eds. Clinicians' Pocket Guide to Chronic Wound Repair. 4th ed. Springhouse, P A: Springhouse Corporation; 1998:85; Ziegler T. R., Pierce, G. F., and Herndon, D. N., 1997, International Symposium on Growth Factors and Wound Healing: Basic Science & Potential Clinical Applications (Boston, 1995, Serono Symposia USA), Publisher: Springer Verlag.

Examples of therapeutic or diagnostic agents which can be incorporated in the hydrogels of the invention, or incorporated into the lipid based nanoparticles, e.g., a liposomes or a virosome, encapsulated by the hydrogels of the invention, include, but are not limited to, narcotic analgesic drugs; salts of gold; corticosteroids; hormones; antimalarial drugs; indole derivatives; pharmaceuticals for arthritis treatment; antibiotics, including Tetracyclines, Penicillin, Streptomycin and Aureomycin; antihelmintic and canine distemper drugs, applied to domestic animals and large cattle, such, as, for example, phenothiazine; drugs based on sulfur, such, as sulfioxazole; antitumor drugs; pharmaceuticals supervising addictions, such as agents controlling alcohol addiction and agents controlling tobacco addiction; antagonists of drug addiction, such, as methadone; weight controlling drugs; thyroid gland controlling drugs; analgesics; drugs controlling fertilization or contraception hormones; amphetamines; antihypertensive drugs; antiinflammatories agents; antitussives; sedatives; neuromuscular relaxants; antiepileptic drugs; antidepressants; antidisrhythmic drugs; vasodilating drugs; antihypertensive diuretics; antidiabetic agents; anticoagulants; antituberculous agents; antipsychotic agents; hormones and peptides. It is understood that above list is not full and simply represents the wide diversification of therapeutic agents that may be included in the compositions. In some embodiments, therapeutic agent is Mitoxantrone, peptide, polyclonal antibody, monoclonal antibody, antigen binding fragment of an antibody, protein (e.g. VEGF) or plasmid DNA.

Those of ordinary skill in the art will recognize numerous other therapeutic or diagnostic agents that may be incorporated into the hydrogels of the invention, or into lipid based nanoparticles, e.g., liposomes or virosomes, encapsulated by the hydrogels of the invention. Examples include a radiosensitizer, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifingal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; anti-angina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopres sin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

Anti-cancer agents include alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists/antagonists, endothelinA receptor antagonists, retinoic acid receptor agonists, immuno-modulators, hormonal and anti-hormonal agents, photodynamic agents, and tyrosine kinase inhibitors.

Antibiotics include aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztreonam), penicillins (e.g., penicillin G, penicillin V, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancomycin; and bacteriostatic agents such as chloramphenicol, clindanyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin.

Enzyme inhibitors are substances which inhibit an enzymatic reaction. Examples of enzyme inhibitors include edrophonium chloride, N-methylphysostigmine, neostigmine bromide, physostigmine sulfate, tacrine, tacrine, 1-hydroxy maleate, iodotubercidin, p-bromotetramiisole, 10-(alpha-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, N°-monomethyl-L-arginine acetate, carbidopa, 3-hydroxybenzylhydrazine, hydralazine, clorgyline, deprenyl, hydroxylamine, iproniazid phosphate, 6-MeO-tetrahydro-9H-pyrido-indole, nialamide, pargyline, quinacrine, semicarbazide, tranylcypromine, N,N-diethylaminoethyl-2,2-diphenylvalerate hydrochloride, 3-isobutyl-1-methylxanthne, papaverine, indomethacind, 2-cyclooctyl-2-hydroxyethylamine hydrochloride, 2,3-dichloro-a-methylbenzylamine (DCMB), 8,9-dichloro-2,3,4, 5-tetrahydro-1H-2-benzazepine hydrochloride, p-amino glutethimide, p-aminoglutethimide tartrate, 3-iodotyrosine, alpha-methyltyrosine, acetazolamide, dichlorphenamide, 6-hydroxy-2-benzothiazolesulfonamide, and allopurinol.

Antihistamines include pyrilamine, chlorpheniramine, and tetrahydrazoline, among others.

Anti-inflammatory agents include corticosteroids, non-steroidal anti-inflammatory drugs (e.g., aspirin, phenylbutazone, indomethacin, sulindac, tolmetin, ibuprofen, piroxicam, and fenamates), acetaminophen, phenacetin, gold salts, chloroquine, D-Penicillamine, methotrexate colchicine, allopurinol, probenecid, and sulfinpyrazone.

Muscle relaxants include mephenesin, methocarbomal, cyclobenzaprine hydrochloride, trihexylphenidyl hydrochloride, levodopa/carbidopa, and biperiden.

Anti-spasmodics include atropine, scopolamine, oxyphenonium, and papaverine.

Analgesics include aspirin, phenybutazone, idomethacin, sulindac, tolmetic, ibuprofen, piroxicam, fenamates, acetaminophen, phenacetin, morphine sulfate, codeine sulfate, meperidine, nalorphine, opioids (e.g., codeine sulfate, fentanyl citrate, hydrocodone bitartrate, loperamide, morphine sulfate, noscapine, norcodeine, normorphine, thebaine, norbinaltorphimine, buprenorphine, chlomaltrexamine, funaltrexamione, nalbuphine, nalorphine, naloxone, naloxonazine, naltrexone, and naltrindole), procaine, lidocain, tetracaine and dibucaine.

Ophthalmic agents include sodium fluorescein, rose bengal, methacholine, adrenaline, cocaine, atropine, alpha-chymotrypsin, hyaluronidase, betaxalol, pilocarpine, timolol, timolol salts, and combinations thereof.

Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Trophic factors are factors whose continued presence improves the viability or longevity of a cell. Trophic factors include, without limitation, platelet-derived growth factor (PDGP), neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, glial derived neurotrophic factor, ciliary neurotrophic factor, nerve growth factor, bone growth/cartilage-inducing factor (alpha and beta), bone morphogenetic proteins, interleukins (e.g., interleukin inhibitors or interleukin receptors, including interleukin 1 through interleukin 10), interferons (e.g., interferon alpha, beta and gamma), hematopoietic factors, including erythropoietin, granulocyte colony stimulating factor, macrophage colony stimulating factor and granulocyte-macrophage colony stimulating factor; tumor necrosis factors, and transforming growth factors (beta), including beta-1, beta-2, beta-3, inhibin, and activin.

Hormones include estrogens (e.g., estradiol, estrone, estriol, diethylstibestrol, quinestrol, chlorotrianisene, ethinyl estradiol, mestranol), anti-estrogens (e.g., clomiphene, tamoxifen), progestins (e.g., medroxyprogesterone, norethindrone, hydroxyprogesterone, norgestrel), antiprogestin (mifepristone), androgens (e.g., testosterone cypionate, fluoxymesterone, danazol, testolactone), anti-androgens (e.g., cyproterone acetate, flutamide), thyroid hormones (e.g., triiodothyronne, thyroxine, propylthiouracil, methimazole, and iodixode), and pituitary hormones (e.g., corticotropin, sumutotropin, oxytocin, and vasopressin). Hormones are commonly employed in hormone replacement therapy and/or for purposes of birth control. Steroid hormones, such as prednisone, are also used as immunosuppressants and anti-inflammatories.

The therapeutic or diagnostic agent can be an osteogenic protein. Accordingly, in some embodiments, the therapeutic or diagnostic agent is selected from the family of proteins known as the transforming growth factors beta (TGF-β) superfamily of proteins, which includes the activins, inhibins and bone morphogenetic proteins (BMPs). Most preferably, the active agent includes at least one protein selected from the subclass of proteins known generally as BMPs, which have been disclosed to have osteogenic activity, and other growth and differentiation type activities. These BMPs include BMP proteins BMP-2, BMP-3, BMP-4, BMP5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO 95/16035; BMP-14; BMP-15, disclosed in U.S. Pat. No. 5,635,372; or BMP-16, disclosed in U.S. Pat. No. 5,965,403. Other TGF-β proteins, which can be used include Vgr-2, Jones et al., Mol. Endocrinol. 611961 (1992), and any of the growth and differentiation factors (GDFs), including those described in PCT applications WO94/15965; WO94/15949; WO95/01801; WO95/01802; WO94/21681; WO94/15966; WO95/10539; WO96/01845; WO96/02559 and others. Also useful in the invention can be BIP, disclosed in WO94/01557; HP00269, disclosed in JP Publication number: 7-250688; and BMP-14 (also known as MP52, CDMP1, and GDF5), disclosed in PCT application WO93/16099. The disclosures of all of the above applications are incorporated herein by reference. Subsets of BMPs which can be used include BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, and BMP18. Other osteogenic agents known in the art can also be used, such as teriparatide (FORTEO™), CHRYSALIN®, prostaglandin E2, or LIM protein, among others.

The therapeutic or diagnostic agent, e.g., a protein or a peptide, can be recombinantly produced, or purified from a protein composition. The active agent, if a TGF-β such as a BMP, or other dimeric protein, can be homodimeric, or can be heterodimeric with other BMPs (e.g., a heterodimer composed of one monomer each of BMP-2 and BMP-6) or with other members of the TGF-β superfamily, such as activins, inhibins and TGF-β1 (e.g., a heterodimer composed of one monomer each of a BMP and a related member of the TGF-β superfamily). Examples of such heterodimeric proteins are described for example in Published PCT Patent Application WO 93/09229, the content of which is incorporated herein by reference.

The therapeutic or diagnostic agent can further refer to additional agents such as the Hedgehog, Frazzled, Chordin, Noggin, Cerberus and Follistatin proteins. These families of proteins are generally described in Sasai et al., (1994) Cell 791779-790 (Chordin); PCT Patent Publication WO94/05800 (Noggin); and Fukui et al., Devel. Biol. 159: 1-31 (1993) (Follistatin). Hedgehog proteins are described in WO96/16668; WO96/17924; and WO95/18856. The Frazzled family of proteins is a recently discovered family of proteins with high homology to the extracellular binding domain of the receptor protein family known as Frizzled. The Frizzled family of genes and proteins is described in Wang et al., Biol. Chem. 271:44684476 (1996). The active agent can also include other soluble receptors, such as the truncated soluble receptors disclosed in PCT patent publication WO95/07982. From the teaching of WO95/07982, one skilled in the art will recognize that truncated soluble receptors can be prepared for numerous other receptor proteins. The above publications are hereby incorporated by reference herein.

The hydrogels of the invention may comprise cells. The cells amenable to be encapsulated by the hydrogels of the invention include, but are not limited to, stem cells (embryonic stem cells, mesenchymal stem cells, bone-marrow derived stem cells and hematopoietic stem cells), chondrocytes progenitor cells, pancreatic progenitor cells, myoblasts, fibroblasts, keratinocytes, neuronal cells, glial cells, astrocytes, pre-adipocytes, adipocytes, vascular endothelial cells, hair follicular stem cells, endothelial progenitor cells, mesenchymal cells, neural stem cells and smooth muscle progenitor cells.

In some embodiments, the cell is a genetically modified cell. A cell can be genetically modified to express and secrete a desired compound, e.g., a bioactive agent, a growth factor, differentiation factor, cytokines, and the like. Methods of genetically modifying cells for expressing and secreting compounds of interest are known in the art and easily adaptable by one of skill in the art.

Differentiated cells that have been reprogrammed into stem cells can also be used. For example, human skin cells reprogrammed into embryonic stem cells by the transduction of Oct3/4, Sox2, c-Myc and Klf4 (Junying Yu, et. al., Science, 2007, 318:1917-1920 and Takahashi K. et. al., Cell, 2007, 131:1-12).

Cells useful for incorporation into the composition can come from any source, e.g., a mammal. For example, the cell can be from a human, a rat or a mouse. Human cells include, but are not limited to, human cardiac myocytes-adult (HCMa), human dermal fibroblasts-fetal (HDF-f), human epidermal keratinocytes (HEK), human mesenchymal stem cells-bone marrow, human umbilical mesenchymal stem cells, human hair follicular inner root sheath cells, human umbilical vein endothelial cells (HUVEC), and human umbilical vein smooth muscle cells (HUVSMC), human endothelial progenitor cells, human myoblasts, human capillary endothelial cells, and human neural stem cells.

Exemplary rat and mouse cells include, but not limited to, RN-h (rat neurons-hippocampal), RN-c (rat neurons-cortical), RA (rat astrocytes), rat dorsal root ganglion cells, rat neuroprogenitor cells, mouse embryonic stem cells (mESC) mouse neural precursor cells, mouse pancreatic progenitor cells, mouse mesenchymal cells and mouse endodermal cells.

In some embodiments, tissue culture cell lines can be used in the hydrogels described herein. Examples of cell lines include, but are not limited to, C166 cells (embryonic day 12 mouse yolk), C6 glioma Cell line, HL1 (cardiac muscle cell line), AML12 (nontransforming hepatocytes), HeLa cells (cervical cancer cell line) and Chinese Hamster Ovary cells (CHO cells).

An ordinary skill artisan in the art can locate, isolate and expand such cells. In addition, the basic principles of cell culture and methods of locating, isolation and expansion and preparing cells for tissue engineering are described in "Culture of Cells for Tissue Engineering" Editor(s): Gordana Vunjak-Novakovic, R. Ian Freshney, 2006 John Wiley & Sons, Inc., and Heath C. A., Trends in Biotechnology, 2000, 18:17-19, content of both of which is herein incorporated by reference in its entirety.

In one embodiment, the biologic may be a peptide, e.g., a peptide having a molecular weight of 250 kDa or less. In a further embodiment, the peptide is an angiogenesis factor, e.g., FGF, VEGF, VEGFR, IGF, NRP-1, Ang1, Ang2, PDGF, PDGFR, TGF-β, endoglin, a TGF-β receptor, MCP-1, integrin, an integrin ligand (e.g., an RGD peptide), VE-cadherin, CD31, ephrin, plasminogen activator, plasminogen activator inhibitor-1, eNOS, COX-2, AC133, ID1 or ID3. In a specific embodiment, the peptide encapsulated by the hydrogels of the present invention is VEGF.

Biologics, such as polynucleotides, polypeptides, or other agents (e.g., antigens) are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. The preparations herein can also be at least 75%, more preferably at least about 90%, and most preferably at least about 99%, by weight the compound of interest. For example, a purified compound is one that is at least about 90%, about 91%, about 92%, about 93%, about 94%, about 95%, about 98%, about 99%, or about 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents.

Similarly, by "substantially pure" is meant that a nucleotide, polypeptide, or other compound has been separated from the components that naturally accompany it. Typically, the nucleotides and polypeptides are substantially pure when they are at least about 60%, about 70%, about 80%, about 90%, about 95%, about 99%, or even 100%, by weight, free from the proteins and naturally-occurring organic molecules with they are naturally associated. Examples include synthesized compounds, recombinant compounds (e.g., peptides, proteins, nucleic acids) or purified compounds, such as purified by standard procedures including chromatographic methods.

An "isolated nucleic acid" is a nucleic acid, the structure of which is not identical to that of any naturally occurring nucleic acid, or to that of any fragment of a naturally occurring genomic nucleic acid spanning more than three separate genes. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybridgene, i.e., a gene encoding a fusion protein. Isolated nucleic acid molecules according to the present disclosure further include molecules produced synthetically, as well as any nucleic acids that have been altered chemically and/or that have modified backbones.

The therapeutic or diagnostic agent which may be encapsulated in the hydrogel of the invention or in a liposome encapsulated in the hydrogel of the invention, may be a STING adjuvant, a CRISPR-Cas 9 reagent and an adjuvant-loaded subcellular vesicle derived from disrupted cancer cells.

In one embodiment, the therapeutic or diagnostic agent may also be a vaccine.

The polymers (e.g., alginate polymers) of the hydrogel may be about 1-90% crosslinked, e.g., at least about 1%, about 10%, about 20%, about 30%, about 40%, about 50%, about 60%, or about 70% crosslinked. Ranges intermediate to the recited values are also intended to be part of this invention. For example, the polymers of the hydrogel may be about 1% to about 10%, about 7% to about 15%, about 12% to about 20%, about 15% to about 30%, about 20% to about 40%, about 30% to about 50%, about 45% to about 65% or about 50% to about 90% crosslinked.

The term "% crosslinked", used interchangeably with the term "crosslinking density", refers to the number of moles of click moieties conjugated per moles of alginate monomers that have reacted with each other.

The polymer (e.g., alginate) can be oxidized (e.g., highly oxidized), reduced, or be a mixture thereof. For example, a hydrogel of the invention may comprise a mixture of polysaccharide polymers, e.g., alginate polymers, that comprise algoxinol and algoxalate. In some cases, oxidized polymers or partially oxidized polymers are biodegradable. For example, hydrogels comprising oxidized or partially oxidized alginate are biodegradable.

Therapeutic or diagnostic agent or a lipid based nanoparticle, e.g., a liposome or a virosome, encapsulating a therapeutic or diagnostic agent is released from the hydrogel of the invention in a sustained release manner, e.g., at a constant rate during a given number of hours, e.g., 1, 2, 3, 4, 5, 6, 7, 8, 9, 10, 11, 12, 13, 14, 15, 16, 17, 18, 19, 20, 21, 22, 23 or 24 hours; or days, e.g., 1, 2, 3, 4, 5, 6, 7, or 8 days; or weeks, e.g., 1, 2, 3, 4, 5, 6, 7 or 8 weeks; or months, e.g., 1, 2, 3, 4, 5, 6, 7, 8, 9, 10, 11 or 12 months. When a therapeutic or a diagnostic agent or a lipid based nanoparticle, e.g., a liposome or a virosome, encapsulating a therapeutic or diagnostic agent is released from the hydrogel of the invention at a constant rate, the amount of the therapeutic or diagnostic agent or the amount of lipid based nanoparticle released from the hydrogel in a given time period is about the same, e.g., within about 0% to about 20%, of the amount of the therapeutic or diagnostic agent or the lipid based nanoparticle released from the hydrogel during the time period immediately prior or immediately after the given time period.

The rate of release of the therapeutic or diagnostic agent or of lipid based nanoparticle encapsulating the therapeutic or diagnostic agent may be modulated by changing one or more parameters during the preparation of the hydrogel. Such parameters include, but are not limited to, the degree of click substitution; % polysaccharide oxidation; concentration of the click conjugated polysaccharide during the cross-linking reaction (gelation); or the pH of the surrounding environment.

The degree of click substitution may be modulated by varying the number of molar equivalents of the click reagent in the click conjugation reaction with the oxidized and reduced or a highly oxidized polysaccharide, e.g., algoxinol or algoxalate. For example, one may increase the number of click molecules conjugated to a polysaccharide of the invention by increasing the number of molar equivalents of the click reagent in the click conjugation reaction. In another example, one may decrease the number of click molecules conjugated to a polysaccharide of the invention by decreasing the number of molar equivalents of the click reagent in the click conjugation reaction. In one embodiment, the click conjugation reaction may comprise about 1 to about 2000 molar equivalents of a click reagent, e.g., about 1, about 5, about 10, about 20, about 50, about 100, about 150, about 200, about 250, about 300, about 350, about 400, about 450, about 500, about 550, about 600, about 650, about 700, about 750, about 800, about 850, about 900, about 950 or about 1000 molar equivalents of the click reagent. Ranges intermediate to the recited values are also intended to be part of this invention. For example, the click conjugation reaction may comprise about 1 to about 5, about 2 to about 10, about 5 to about 10, about 10 to about 50, about 40 to about 150, about 100 to about 400, about 300 to about 500, about 400 to about 1000, about 500 to about 1500 or about 1500 to about 2000 molar equivalents of the click reagent.

In one embodiment, the polysaccharide, e.g., the oxidized and reduced or a highly oxidized polysaccharide, e.g., comprising algoxinol or algoxalate, may comprise a degree of click substitution that is about 0.01% to about 90%, e.g., about 0.01%, about 0.05%, about 0.1%, about 0.5%, about 1%, about 5%, about 10%, about 15%, about 20%, about 25%, about 30%, about 35%, about 40%, about 45% or about 90%. Ranges intermediate to the recited values are also intended to be part of this invention. For example, the polysaccharide may be about 0.01% to about 0.05%, about 0.01% to about 1%, about 0.1% to about 5%, about 5% to about 15%, about 10% to about 20%, about 15% to about 25%, about 20% to about 35%, about 30% to about 40% or about 35% to about 50% click substituted.

One may also modulate the number of click molecules conjugated to a polysaccharide of the invention by modulating % oxidation of the polysaccharide. For example, higher % oxidation of the polysaccharide prior to its reduction, e.g., with ammonia borane, or, prior to its further oxidation, e.g., with sodium chlorite, may create additional aldehyde moieties, which, upon their conversion to alcohol moieties upon reduction, or to carboxylic acid moieties upon further oxidation, may serve as sites for click reagent conjugation.

Modulating the degree of click substitution of the polysaccharide of the invention may allow modulating the time to gelation, or the time it takes the click conjugated polysaccharide to cross-link and to produce a hydrogel. For example, a higher degree of click substitution may lead to shorter gelation times.

Modulating the degree of click substitution also allows modulating the cross-linking density and the average diameter of pores in the resulting hydrogel, i.e., mesh size of the resulting hydrogel. For example, a higher degree of click substitution may lead to smaller average pore diameter, or mesh size of the hydrogel, which may lead to a decreased rate of release of the therapeutic or diagnostic agent or a lipid based nanoparticle, e.g., a liposome or a virosome, comprising the therapeutic or diagnostic agent. A higher degree of click substitution may also lead to longer retention of the lipid based nanoparticles comprising the therapeutic or diagnostic agent in the hydrogel.

In yet another example, the concentration of the polysaccharide of the invention during the cross-linking reaction may be varied. For example, a higher concentration of a polysaccharide, e.g., a click conjugated polysaccharide, in the click conjugation reaction, may lead to smaller mesh size of the resulting hydrogel, which may, in turn, cause a decreased rate of release of the therapeutic or diagnostic agent or a lipid based nanoparticle, e.g., a liposome or a virosome, comprising the therapeutic or diagnostic agent from the hydrogel of the invention. A higher degree of click substitution may also lead to longer retention of lipid based nanoparticles comprising the therapeutic or diagnostic agent in the hydrogel. In some embodiments, the concentration of click conjugated polysaccharide during hydrogel formation, e.g., concentration of the alginate material present in the solution immediately prior to formation of the hydrogel, may be from about 0.01% to about 50% w/v, e.g., about 0.01% to about 10% w/v, about 0.1% to about 5% w/v, about 1% to about 15% w/v, about 10% to about 30% w/v, about 12% to about 35% w/v, about 15% to about 25% w/v, about 20% to about 45% w/v or about 35% to about 50% w/v.

Hydrogels of the present invention, e.g., hydrogels comprising alginate, such as hydrogels comprising algoxinol and/or algoxalate, are not degraded by endogenous enzymes present in a host or a subject, e.g., a human. The hydrogels of the invention may be chemically degraded, e.g., hydrolyzed when exposed to acidic or alkaline condition. Acidic conditions comprise a pH 6.5 or lower, while alkaline conditions comprise a pH 8 or higher. Without wishing to be bound by a theory, it is believed that the rate of chemical degradation of the hydrogels of the invention is pH dependent. For example, the rate of chemical degradation of the hydrogels of the invention at pH 2 is higher than at pH 6, and the rate of chemical degradation of the hydrogels of the invention at pH 8 is higher than at pH 12.

When the hydrogel of the invention is exposed to acidic or alkaline conditions, the cargo comprised in the hydrogel, e.g., a therapeutic or diagnostic agent, or a lipid based nanoparticle, e.g., a liposome or a virosome, encapsulating a therapeutic or diagnostic agent, is released from the hydrogel at an increased rate as compared to its rate of release at neutral pH, e.g., pH of 7.4. For example, because the intratumoral environment may be characterized by an acidic pH of 6.5 or lower, the rate of cargo release from the hydrogels of the invention may be increased in the intratumoral environment, thereby allowing sustained and targeted delivery of anti-cancer agents.

V. Lipid Based Nanoparticles Encapsulated in the Hydrogels of the Invention

The present invention also provides a drug delivery composition comprising a lipid based nanoparticle encapsulating a therapeutic or diagnostic agent and a hydrogel of the invention encapsulating the liposome. The term "lipid based nanoparticle", as used herein, refers to any nanoparticle that comprises lipids and that may be used for delivery for a therapeutic or diagnostic agent to a subject. In one embodiment, the lipid based nanoparticle is a liposome. In another embodiment, the lipid based nanoparticle is a virosome.

Delivering a therapeutic or a diagnostic agent in a liposome may be desirable because liposomes may provide protection of such agents against systemic enzymatic degradation, or may be used to mimic antigen presenting cells (APCs). However, there are challenges associated with liposomal drug delivery. For example, the composition of a liposome may have a big effect on the loading efficiency, efficacy of the therapeutic or diagnostic agent encapsulated by the liposome and the systemic toxicity of the therapeutic or diagnostic agent encapsulated by the liposome. Accordingly, there is a need for sustained, localized liposomal drug delivery that may reduce systemic toxicity and provide localization of drug cargos to target tissues. However, currently available liposome delivery compositions cannot retain liposomal cargos, with release of the liposomal cargos occurring within hours or days. The compositions currently available in the art are also unable to deliver intact liposomes to target locations, e.g., in cases intact liposomes are required for cargos to cross the cell membrane for cytosolic delivery.

It has been surprisingly discovered that the reduced and/or highly oxidized polysaccharides of the invention, e.g., polysaccharides comprising algoxinol and/or algoxalate, e.g., made using a method described herein, are particularly useful for preparing hydrogels that may be used to encapsulate liposomes. Specifically, it has been surprisingly discovered that the hydrogels of the invention, e.g., hydrogels prepared from alginate comprising algoxinol and/or algoxalate conjugated to click reagents, can retain intact liposomes over a long period of time and can deliver intact liposomes to a desired location in a subject, e.g., to a cytosol of a cell.

As used herein, the term "intact liposome" includes a liposome that retains its size, e.g., average diameter, while it is encapsulated by a hydrogel, or while it is in the process of being delivered to a desired location within a host or a subject, e.g., a human. An intact liposome is one that resembles the therapeutic input and does not coalesce with other liposomes to generate polydisperse liposomes of a larger size, e.g., larger average diameter, nor fragment into smaller liposomes or micelles.

The liposome may be delivered to a desired location, e.g., to a cytosol of a cell, in an intact form after the hydrogel encapsulating the liposome is degraded inside a host, e.g., a subject, such as a human. In one example, the hydrogel comprises alginate, e.g., algoxinol or algoxalate, which is not susceptible to degradation by a host endogenous enzyme. Because alginate, e.g., algoxinol or algoxalate, is not susceptible to degradation by a host endogenous enzyme, a hydrogel comprising alginate is capable of retaining a liposome for a prolonged period of time. For example, a liposome of the invention may remain encapsulated in the hydrogel for at least 5 days, at least 10 days, at least 15 days, at least 20 days, at least 25 days, at least 30 days, at least 35 days, at least 40 days, at least 45 days, at least 50 days, at least 55 days, at least 60 days, at least 65 days, at least 70 days, at least 75 days or at least 80 days.

A liposome that remains intact during delivery to a desired location within a host or a subject is a liposome that retains it average size, e.g., an average diameter, during the delivery. For example, the average diameter of an intact liposome that has been encapsulated by a hydrogel of the invention is within about 50%, e.g., about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2% or about 1%, of the average diameter of the same liposome prior to encapsulation, or within about 25%, e.g., about 24%, about 23%, about 22%, about 21%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2% or about 1%, of the average diameter of a standard. The standard may be a liposome prepared in the same manner as the liposome used for encapsulation with a hydrogel. Size of a liposome may be measured by any method known to one of skill in the art, for example, by dynamic light scattering (DLS).

A liposome useful in the context of the present invention may be any liposome known in the art that may be used to deliver a therapeutic or diagnostic agent. For example, the liposome may be a neutral liposome, e.g., a liposome comprising uncharged lipids (Niosome). Examples of such lipids include, but are not limited to, 1,2-dioleoyl-sn-glycero-3-phosphocholine (DOPC) and cholesterol (CHOL). The liposome may also be a charged liposome, e.g., a cationic or an anionic liposome comprising, e.g., a positively charged or a negatively charged lipids. Non-limiting examples of positively charged lipids include N-[1-(2,3-Dioleoyloxy)propyl]-N,N,N-trimethylammonium methyl-sulfate (DOTAP) and hydrogenated soy phosphatidilcholine (Hydro Soy PC). Non-limiting examples of negatively charged lipids include 1,2-diolcoyl-sn-glycero-3-phospho-(1'-rac-glycerol) (DOPG). In some embodiments, the liposome useful in the context of the present invention is a therapeutic liposome or a diagnostic liposome, e.g., a liposome comprising a therapeutic or diagnostic agent as described above.

A virosome is a drug or vaccine delivery mechanism consisting of unilamellar phospholipid membrane (either a mono- or bi-layer) vesicle incorporating virus derived proteins to allow the virosomes to fuse with target cells. Virosomes are not able to replicate but are pure fusion-active vesicles. A virosome useful in the context of the present invention may be any virosome known in the art that may be used to deliver any virus derived proteins. In some embodiments, the virosome may comprise a protein derived from an influenza virus, e.g., hemagglutinin or neuraminidase. In some embodiments, a virosome is a therapeutic or a diagnostic virosome, e.g., a virosome comprising a therapeutic or diagnostic agent as described above. In some embodiments, a virosome comprises a vaccine.

VI. Pharmaceutical Compositions of the Invention

For administration to a subject, the hydrogels of the invention can be provided in pharmaceutically acceptable (e.g., sterile) compositions. Accordingly, another aspect described herein is a pharmaceutical composition comprising a hydrogel and a pharmaceutically acceptable carrier. These pharmaceutically acceptable compositions comprise a hydrogel formulated together with one or more pharmaceutically acceptable carriers (additives) and/or diluents. As described in detail below, the pharmaceutical compositions of the present disclosure can be specifically formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and/or systemic absorption), boluses, powders, granules, pastes for application to the tongue; (2) parenteral administration, for example, by subcutaneous, intramuscular, intravenous (e.g., bolus or infusion) or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., *Ann. Rev. Pharmacol. Toxicol.* 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, content of all of which is herein incorporated by reference.

As used herein, the term "pharmaceutically acceptable" or "pharmacologically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Moreover, for animal (e.g., human) administration, it will be understood that compositions should meet sterility, pyrogenicity, general safety and purity standards as required by FDA Office of Biological Standards.

As used herein, the term "pharmaceutically acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL;

(22) $C_2$-$C_{12}$ alcohols, such as ethanol; and (23) other nontoxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable carrier" or the like are used interchangeably herein.

The hydrogel of the invention comprising the therapeutic agent can be delivered to an in vivo locus in a subject. Exemplary in vivo loci include, but are not limited to site of a wound, trauma or disease. The hydrogel can be delivered to the in vivo locus by, for example, implanting the compositions into a subject. Hydrogels that are to be implanted, i.e., implantable devices, can additionally include one or more additives. Additives can be resolving (biodegradable) polymers, mannitol, starch sugar, inosite, sorbitol, glucose, lactose, saccharose, sodium chloride, calcium chloride, amino acids, magnesium chloride, citric acid, acetic acid, hydroxyl-butanedioic acid, phosphoric acid, glucuronic acid, gluconic acid, poly-sorbitol, sodium acetate, sodium citrate, sodium phosphate, zinc stearate, aluminium stearate, magnesium stearate, sodium carbonate, sodium bicarbonate, sodium hydroxide, polyvinylpyrolidones, polyethylene glycols, carboxymethyl celluloses, methyl celluloses, starch or their mixtures.

The implantable device can have virtually any regular or irregular shape including, but not limited to, spheroid, cubic, polyhedron, prism, cylinder, rod, disc, or other geometric shape. Accordingly, in some embodiments, the implant is of cylindrical form from about 0.5 to about 10 mm in diameter and from about 0.5 to about 10 cm in length. Preferably, its diameter is from about 1 to about 5 mm and length from about 1 to about 5 cm.

In some embodiments, the implantable device is of spherical form. When the implantable device is in a spherical form, its diameter can range from about 0.5 to about 50 mm in diameter. In some embodiments, a spherical implant's diameter is from about 5 to about 30 mm. Preferably the diameter is from about 10 to about 25 mm.

In some embodiments, the hydrogel of the present invention may be used to prepare a drug delivery device or a drug depot. The drug delivery device may also be biodegradable and refillable. Refillable biodegradable drug delivery devices are described, e.g., in PCT/US2015/024540 and U.S. application Ser. No. 14/878,578, the entire contents of each of which are hereby incorporated herein by reference. The refillable biodegradable drug delivery devices comprise a target recognition moiety capable of interacting with a target conjugated to a drug refill.

In some embodiments, the hydrogel of the invention used to prepare a refillable biodegradable drug delivery device may comprise a polysaccharide conjugated to at least two click reagents belonging to two different click pairs as described above. For example, the polysaccharide may comprise a first click reagent that functions as a target recognition moiety for the drug delivery device by reacting with its click pair conjugated to the drug refill. The polysaccharide may also comprise a second click reagent that functions as a cross-linking agent as described above, or that functions to conjugate a moiety, e.g., a therapeutic agent, to the polysaccharide. In one embodiment, the first click reagent and the second click reagent do not cross-react, i.e., do not react with each other, but only react with their click pairs.

In other embodiments, the hydrogel of the invention may be used to prepare a drug refill for the refillable biodegradable drug delivery device as described above. The hydrogel used to prepare the drug refill may comprise a polysaccharide conjugated to at least two click reagents as described above, where at least one click reagent may function as a target by reacting with its click pair conjugated to the drug delivery device.

VII. Methods of Treatment Using Hydrogels of the Invention

The present invention also relates to methods of treating a subject in need thereof. The methods comprise administering to the subject an effective amount of a hydrogel, a dosage form, a pharmaceutical composition or an implantable drug delivery device of the invention.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

In some embodiments, administration includes implanting a composition, e.g., a hydrogel, described herein in a subject.

The term "therapeutically effective amount", as used herein, means that amount of a compound, material, or composition comprising a compound described herein which is effective for producing some desired therapeutic effect in at least a sub-population of cells in a subject at a reasonable benefit/risk ratio applicable to any medical treatment. Thus, "therapeutically effective amount" means that amount which, when administered to a subject for treating a disease, is sufficient to effect such treatment for the disease.

Determination of an effective amount is well within the capability of those skilled in the art. Generally, the actual effective amount can vary with the specific compound, the use or application technique, the desired effect, the duration of the effect and side effects, the subject's history, age, condition, sex, as well as the severity and type of the medical condition in the subject, and administration of other pharmaceutically active agents. Accordingly, an effective dose of compound described herein is an amount sufficient to produce at least some desired therapeutic effect in a subject.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of use or administration utilized.

The effective dose can be estimated initially from cell culture assays. A dose can be formulated in animal models to achieve a circulating plasma concentration range that includes the $IC_{50}$ (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay.

Generally, the term "treatment" or "treating" is defined as the application or administration of a therapeutic agent to a patient, or application or administration of a therapeutic agent to an isolated tissue or cell line from a patient, said patient having a disease, a symptom of disease or a predisposition toward a disease, with the purpose to cure, heal, alleviate, relieve, alter, remedy, ameliorate, improve or affect the disease, the symptoms of disease or the predisposition toward disease. Thus, treating can include suppressing, inhibiting, preventing, treating, or a combination thereof. Treating refers, inter alia, to increasing time to sustained progression, expediting remission, inducing remission, augmenting remission, speeding recovery, increasing efficacy of or decreasing resistance to alternative therapeutics, or a combination thereof. "Suppressing" or "inhibiting", refers, inter alia, to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. In one embodiment the symptoms are primary, while in another embodiment, symptoms are secondary. "Primary" refers to a symptom that is a direct result of a disorder, e.g., diabetes, while, secondary refers to a symptom that is derived from or consequent to a primary cause. Symptoms may be any manifestation of a disease or pathological condition.

Accordingly, as used herein, the term "treatment" or "treating" includes any administration of a compound described herein and includes: (i) preventing the disease from occurring in a subject which may be predisposed to the disease but does not yet experience or display the pathology or symptomatology of the disease; (ii) inhibiting the disease in an subject that is experiencing or displaying the pathology or symptomatology of the diseased (i.e., arresting further development of the pathology and/or symptomatology); or (iii) ameliorating the disease in a subject that is experiencing or displaying the pathology or symptomatology of the diseased (i.e., reversing the pathology and/or symptomatology).

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

Efficacy of treatment is determined in association with any known method for diagnosing the disorder. Alleviation of one or more symptoms of the disorder indicates that the compound confers a clinical benefit. Any of the therapeutic methods described to above can be applied to any suitable subject including, for example, mammals such as dogs, cats, cows, horses, rabbits, monkeys, and most preferably, humans.

As used herein, the term "subject" includes any subject who may benefit from being administered a hydrogel or an implantable drug delivery device of the invention. The term "subject" includes animals, e.g., vertebrates, amphibians, fish, mammals, non-human animals, including humans and primates, such as chimpanzees, monkeys and the like. In one embodiment of the invention, the subject is a human.

The term "subject" also includes agriculturally productive livestock, for example, cattle, sheep, goats, horses, pigs, donkeys, camels, buffalo, rabbits, chickens, turkeys, ducks, geese and bees; and domestic pets, for example, dogs, cats, caged birds and aquarium fish, and also so-called test animals, for example, hamsters, guinea pigs, rats and mice.

In one embodiment, the present invention provides a method for treating ear related disorders. The method comprises administering to a subject in need thereof a hydrogel, or a dosage form for treating ear related disorders, such as otitis. Such dosage forms are administered into an external auditory canal of a subject in need thereof. The dosage forms may comprise a variety of therapeutic agents, e.g., at least one antibiotic. The drug delivery devices for delivering therapeutic agents into an ear are described, e.g., in US 2014/0107423, the entire contents of which are hereby incorporated herein by reference.

In another embodiment, the present invention also provides a hydrogel, or a dosage form for treating eye related disorders. The method comprises administering into an eye of a subject in need thereof a hydrogel, or a dosage form of the invention. The hydrogel, or a dosage form of the invention may comprise at least one therapeutic agent. Non-limiting examples of the therapeutic agents that may be used in an ophthalmic dosage form include, e.g., antibiotics, corticoids, local anaesthetics, decongestants, non-steroidal antiphlogistics, virustatics, antiseptics, cortisone, anti-allergic active substances, prostaglandin analogues, active substances from the active substance class of antihistamines and corticosteroids, anti-allergic active substances, pantothenic acid derivatives, non-steroidal anti-inflammatory drugs, vasoconstrictors and/or anti-glaucoma active substances in a pharmaceutically effective concentration. Suitable dosage forms for administration into an eye are described, e.g., in US 20150139973, the entire contents of which are hereby incorporated herein by reference.

The present invention also provides methods for treating chronic ischemia in a subject in need thereof. The method comprises administering to the subject an effective amount of a hydrogel, a dosage form, or an implantable device, of the invention. In an embodiment, the hydrogel, the dosage form, or an implantable device of the invention comprises VEGF.

It has been previously found that delivering VEGF locally to the site of ischemia may increase the half-life of VEGF in a subject's body and reduce side treatment related side effects. Accordingly, in one embodiment, the hydrogel, the dosage form or the implantable device is administered locally to the site of ischemia. In some embodiments, the hydrogel, the dosage form or the implantable device is administered to the tissue to be engrafted before and/or after transplantation.

The present invention also provides methods for regenerating a tissue in a subject in need thereof. The method comprises administering to the subject an effective amount of a hydrogel, a dosage form, or an implantable device, of the invention that further comprises a cell. For example, the cell may be a mammalian cell, and the tissue may be a mammalian tissue. In some embodiments, the mammalian cell is of the same type as the tissue to be regenerated. In other embodiments, the mammalian cell is a stem cell. Embodiments of the methods provided herein include contacting a mammalian tissue with a hydrogel, a dosage form, or an implantable device of the invention that further comprises a cell.

In another example, a method for regenerating a tissue in a subject comprises providing a hydrogel, a dosage form, or an implantable device described herein, wherein the hydrogel comprises a cell immobilized within the hydrogel (i.e., the cell remains within the hydrogel for an extended period of time without exiting the hydrogel). The method includes contacting a tissue with the hydrogel, wherein the cell is immobilized within the hydrogel. In some embodiments, the cell is a progeny cell. In some embodiments, the hydrogel remains stable and does not allow for host cell infiltration.

In one embodiment, the hydrogels described herein are useful as an immunoprotective barrier, e.g., for pancreatic islet transplantation. In some cases, pancreatic islet transplantation is a treatment for diabetes, e.g., Type I diabetes. Transplanted cells, such as islets, can be destroyed by immune reactions, and the hydrogels of the invention are capable of encapsulating cells, such as islet cells, prior to implantation/injection of the hydrogel. This way, the hydrogels serve as an immunoprotective barrier in a subject and minimize immune rejection of transplanted cells and tissues.

The present invention is further illustrated by the following examples which should not be construed as limiting. The entire contents of all of the references cited throughout this application are hereby expressly incorporated herein by reference.

EXAMPLES

Example 1: Aldehydes Present in Alginates can React with Cargo Proteins and Click Reagents Alginates of high and low molecular weight were oxidized by reaction with sodium periodate. To this end, alginate with MW of ~265 kDa (MVG or Protanol LF 20/40, FMC Technologies; I-1G or 1-8, Kimica Corp.) and MW of ~32 kDa (VLVG, FMC Technologies) was dissolved in ddH$_2$O at the concentration of 1% w/v. Sodium periodate (Sigma-Aldrich) was added to the solution in an amount that was based on the percent molar ratio to moles of alginate monomer. The solution was then allowed to react overnight in the dark at room temperature. Sodium chloride was added to the solution to the concentration of 0.3 M, and the oxidized product was purified by Tangential Flow Filtration (TFF) or dialyzed using 12-14 kDa MWCO dialysis tubing (Spectrum Labs) overnight with extensive water changes against a decreasing salt gradient from 150 mM to 0 mM NaCl in diH$_2$O.

Figure 2A:
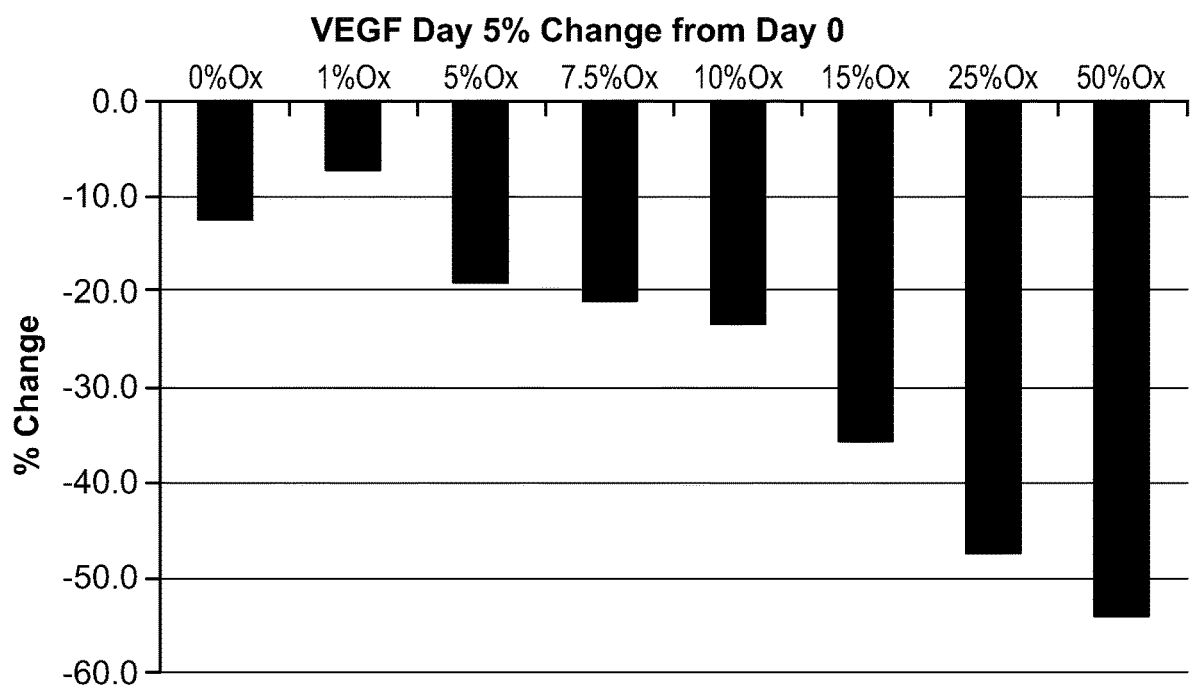
FIG. 2a is a bar graph showing the loss of VEGF bioactivity, as determined by ELISA, as a function of exposure to oxidized alginates.

Oxidized alginates containing 0%-50% aldehydes were incubated with VEGF. Percent change in soluble, un-denatured, VEGF (2% w/v alginate, 4 mcg/mL VEGF) was measured 5 days after incubation by ELISA (R&D Systems Cat # DVE00). As is shown in FIG. 2a, an increase in the % of aldehydes is directly correlated with % change in VEGF, with alginates containing 50% aldehydes resulting in 50% change in VEGF. The data demonstrates that aldehydes incubated with oxidized alginates can react with VEGF.

Figure 2B:
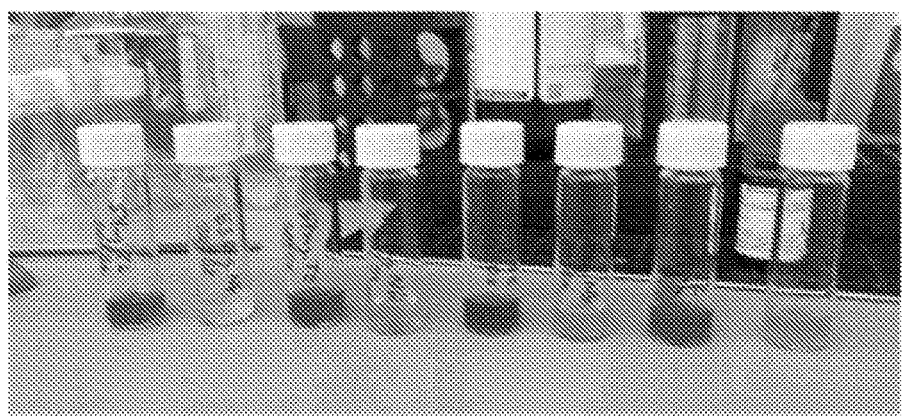
FIG. 2b is a picture of vials containing the oxidized alginates conjugated to Tz and Nb after incubation, illustrating the apparent change in click conjugates due to the presence of aldehydes in oxidized alginates.

Oxidized alginates containing 20%-50% aldehydes were also conjugated with click reagents tetrazine (Tz) and norbornene (Nb). The oxidized alginates showed significant color changes after resuspension at room temperature, indicating an aldehyde concentration dependence on degradation. Shown in FIG. 2b is a picture of vials containing the oxidized alginates conjugated to Tz and Nb after resuspension. Shown from left to right are:

alginate with 20% aldehydes conjugated to Tz;
alginate with 20% aldehydes conjugated to Nb;
alginate with 30% aldehydes conjugated to Tz;
alginate with 30% aldehydes conjugated to Nb;
alginate with 40% aldehydes conjugated to Tz;
alginate with 40% aldehydes conjugated to Nb;
alginate with 50% aldehydes conjugated to Tz;
alginate with 50% aldehydes conjugated to Nb.

The data demonstrate that aldehydes can also react with click reagents to form colored products and imines in a manner dependent on aldehyde concentration. These color shifts represent undesirable changes to the click moieties. Imines can be hydrolyzed back to aldehydes in acidic conditions.

Example 2. Reduction of Alginate Aldehydes

Figure 3A:
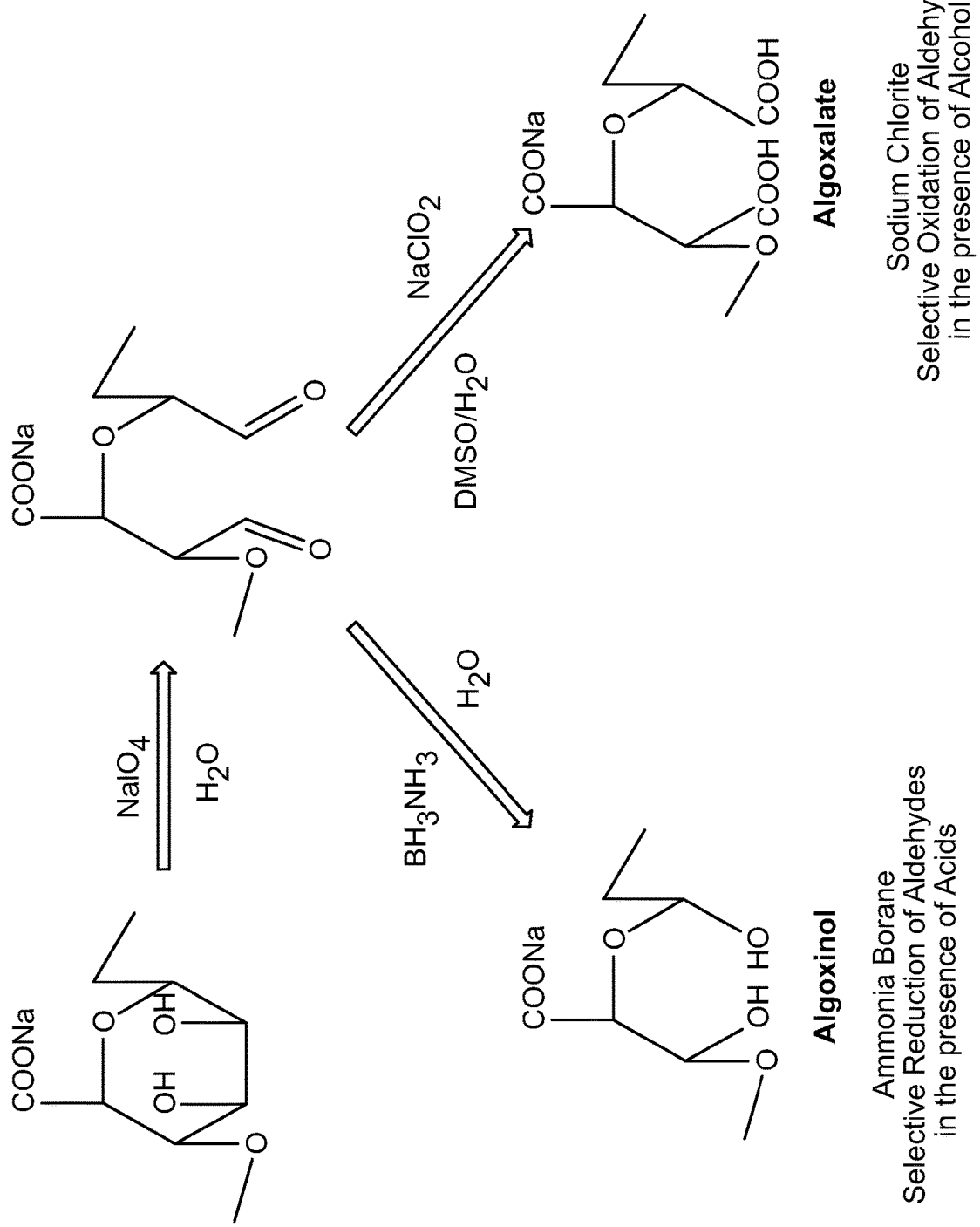
FIG. 3a is a chemical scheme showing oxidation of alginate to produce oxidized alginate containing reactive aldehydes; and subsequent selective reduction or oxidation of the oxidized alginate in order to eliminate the reactive aldehydes.

The purpose of this experiment was to determine the content of residual aldehydes in oxidized alginates that have been reacted with sodium borohydride (NaBH$_4$), ammonia borane (BH$_3$NH$_3$) and sodium chlorite (NaClO$_2$). As is illustrated in FIG. 3a, both sodium borohydride and ammonia borane react with aldehydes present in alginates to form alcohols, while sodium chlorite reacts with aldehydes to form carboxylic acids.

Alginate was oxidized with sodium periodate, such that it contained 5-50% residual aldehydes. The oxidized alginate was then reacted with sodium borohydride, ammonia borane and sodium chlorite, and % of residual aldehydes were quantified using qNMR after each reaction.

Sodium periodate oxidation of alginate was carried out using the procedure as described in Example 1.

To reduce oxidized alginate with sodium borohydride, the alginate solution was treated with sodium borohydride (SB, Sigma-Aldrich) at the molar ratio of SB to alginate oxidized monomers of >1.5:1. The reaction was allowed to proceed overnight at room temperature. Sodium chloride was added to the solution to reach the concentration of 0.3 M, and the SB treated product was purified by Tangential Flow Filtration (TFF) or dialyzed using 12-14 kDa MWCO dialysis tubing (Spectrum Labs) overnight with extensive water changes against a decreasing salt gradient from 150 mM to 0 mM NaCl in diH$_2$O. The solution containing reduced alginate was then frozen and lyophilized to dryness.

To reduce oxidized alginate with ammonia borane, the alginate solution was treated with ammonia borane (AB) complex (Sigma-Aldrich) at the molar ratio of AB to alginate aldehydes of >1.5:1. The reaction was allowed to proceed overnight at room temperature. Sodium chloride was added to the solution to reach the concentration of 0.3M, and the AB treated product was purified by Tangential Flow Filtration (TFF) or dialyzed using 12-14 kDa MWCO dialysis tubing (Spectrum Labs) overnight with extensive water changes against a decreasing salt gradient from 150 mM to 0 mM NaCl in diH$_2$O. The solution containing reduced alginate was then frozen and lyophilized to dryness.

To further oxidize oxidized alginate, the alginate solution was treated with sodium chlorite (SC) at the molar ratio of SC to alginate aldehydes of >1.5:1. Prior to addition of sodium chlorite, dimethylsufoxide (DMSO; Sigma-Aldrich) was added to the solution at the molar ratio of DMSO to sodium chlorite of 5:1 and mixed until the solution became homogenous. The reaction was allowed to proceed overnight at room temperature. Sodium chloride was then added to the solution to reach the concentration of 0.3M, and the SC treated product was purified by Tangential Flow Filtration (TFF) or dialyzed using 12-14 kDa MWCO dialysis tubing (Spectrum Labs) overnight with extensive water changes against a decreasing salt gradient from 150 mM to 0 mM NaCl in diH$_2$O. The solution containing the highly oxidized alginate was then frozen and lyophilized to dryness.

Figure 3B:
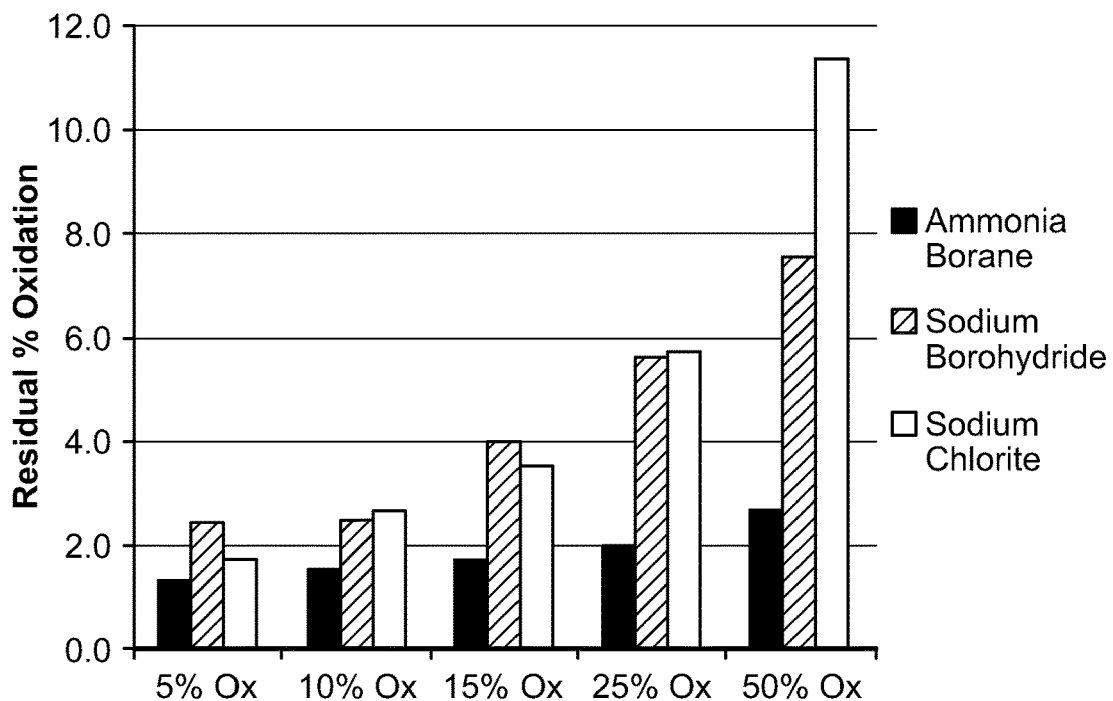
FIG. 3b is a bar graph showing % residual oxidation in oxidized alginates that have been further reduced with ammonia borane or sodium borohydride, or that have been further oxidized with sodium chlorite.
Figure 6A:
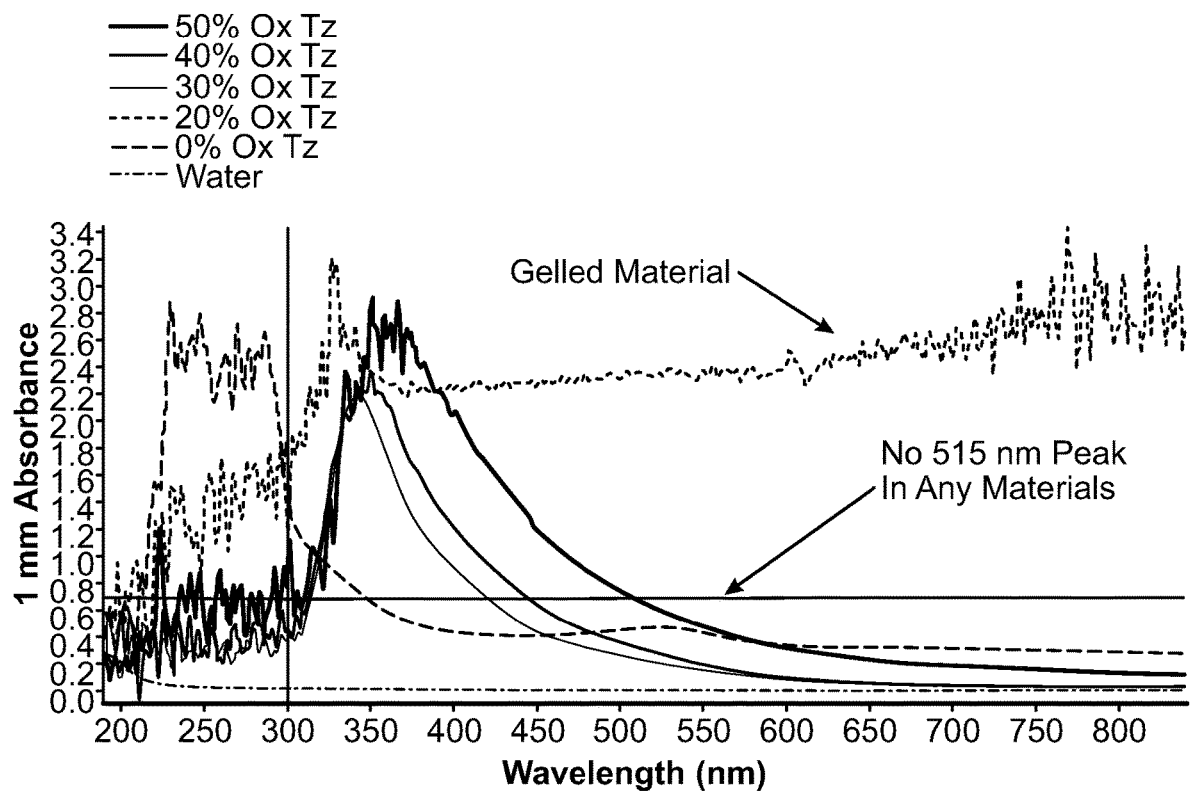
FIG. 6a is a UV-Vis spectrum of Tz-conjugated HighOx alginate material with 20-50% oxidation at day 28 (top panel) and a UV-Vis spectrum of Tz-conjugated HighOx alginate material treated with sodium chlorite containing 20% and 30% conjugation at day 14.
Figure 6A:
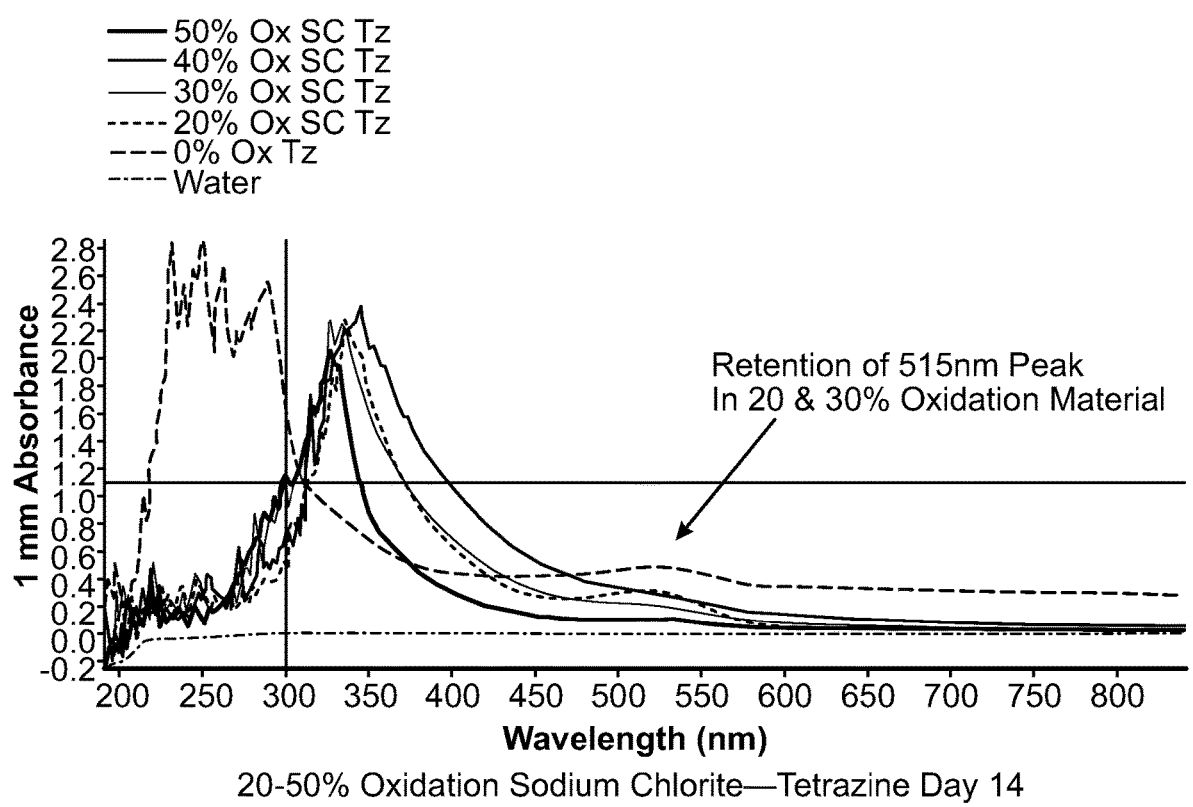
Figure 6B:
FIG. 6b is a panel of two pictures of vials containing Tz-conjugated HighOx alginate material treated with ammonia borane and the HighOx alginate materials treated with sodium chlorite.
Figure 6B:
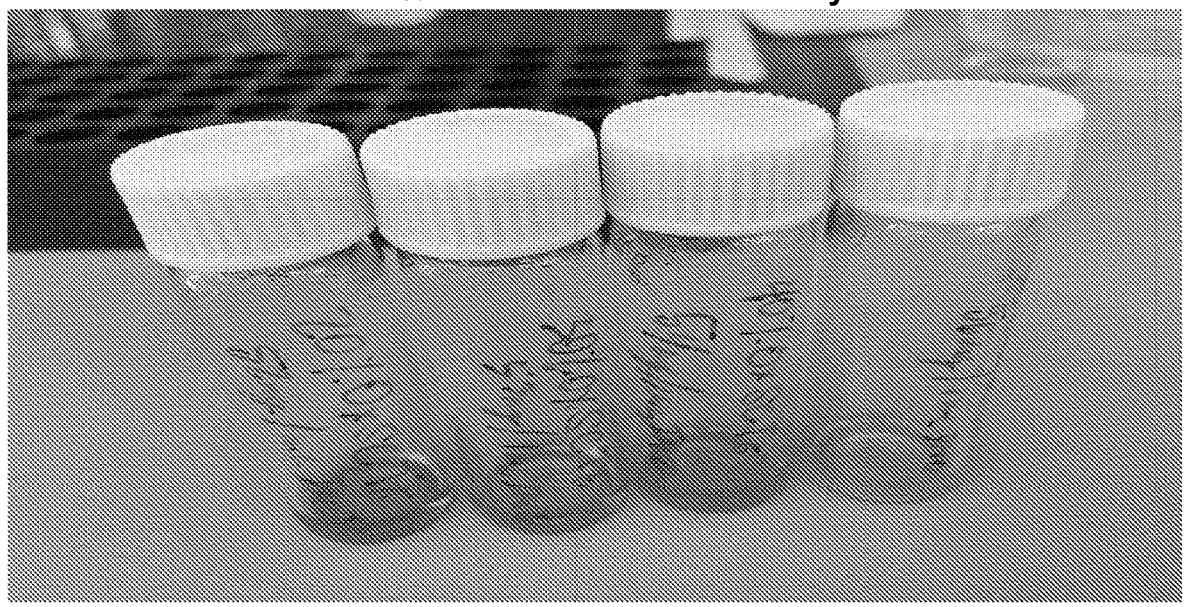

FIG. 3b is a bar graph showing % residual oxidation in oxidized alginates that have been further reduced with ammonia borane or sodium borohydride, or that have been further oxidized with sodium chlorite. The data indicate that ammonia borane is superior to sodium borohydride in its ability to reduce aldehydes and produces alginate containing the lowest level of residual aldehydes. This effect is particularly evident for alginates with higher levels of oxidation. The data also indicate that sodium chlorite oxidation of aldehydes does not reach completion at the "initial DMSO reaction conditions" (1:1 water:DMSO). The residual aldehydes may be eliminated by changing the reaction conditions to 33:1 water:DMSO, as shown in FIG. 6k.

Example 3. Reductive Processing of Oxidized Alginates Reduces the Effect of Aldehydes on Cargo Proteins The goal of this experiment was to evaluate the effect of aldehydes present in oxidized alginate on the biological activity of VEGF. To this end, alginates were oxidized by reaction with sodium periodate to produce oxidized alginates containing 0%-50% aldehydes. The oxidized alginates were then reacted with sodium borohydride (NaBH$_4$), ammonia borane (BH$_3$NH$_3$) and sodium chlorite (NaClO$_2$). The different alginates were incubated with VEGF at 37° C. in PBS containing 1% BSA at alginate concentration of 20 mg/mL and VEGF concentration of 4 µg/mL. Percent change in soluble, un-denatured, VEGF (2% w/v alginate, 4 mcg/mL VEGF) was measured 5 days after incubation in EBM cell culture media or in a solution containing 1% BSA by ELISA (R&D Systems Cat # DVE00).

Figure 4A:
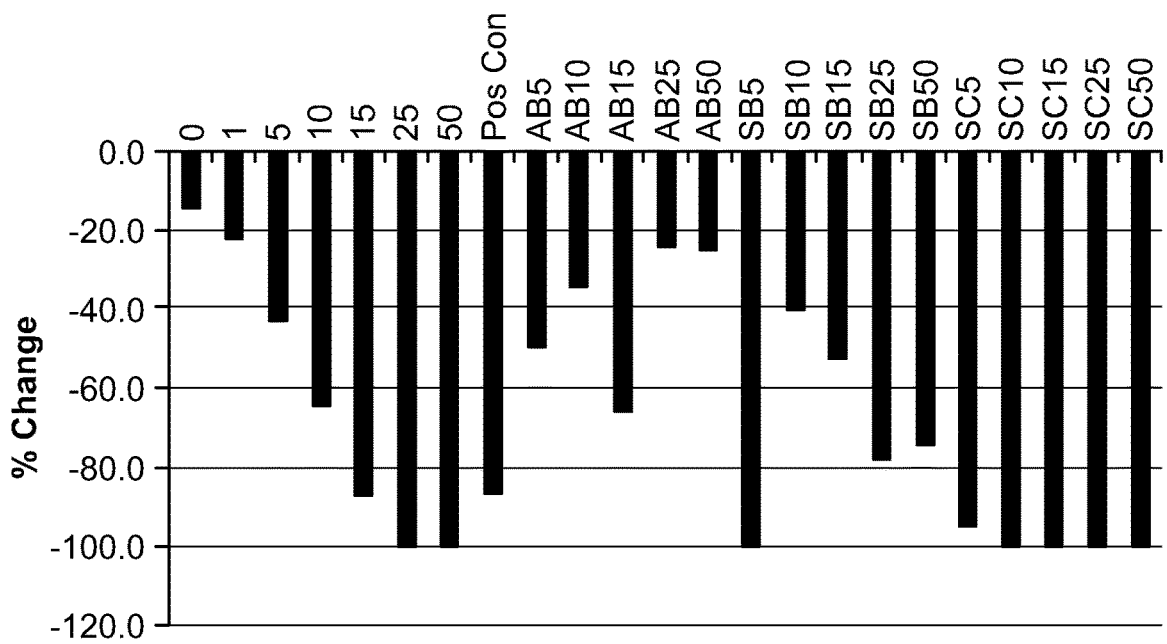
FIG. 4a is a bar graph showing % change in VEGF bioactivity measured by ELISA after 5 days of incubation in EBM, illustrating the loss of VEGF bioactivity as a function of exposure to oxidized or reduced alginate.
Figure 4B:
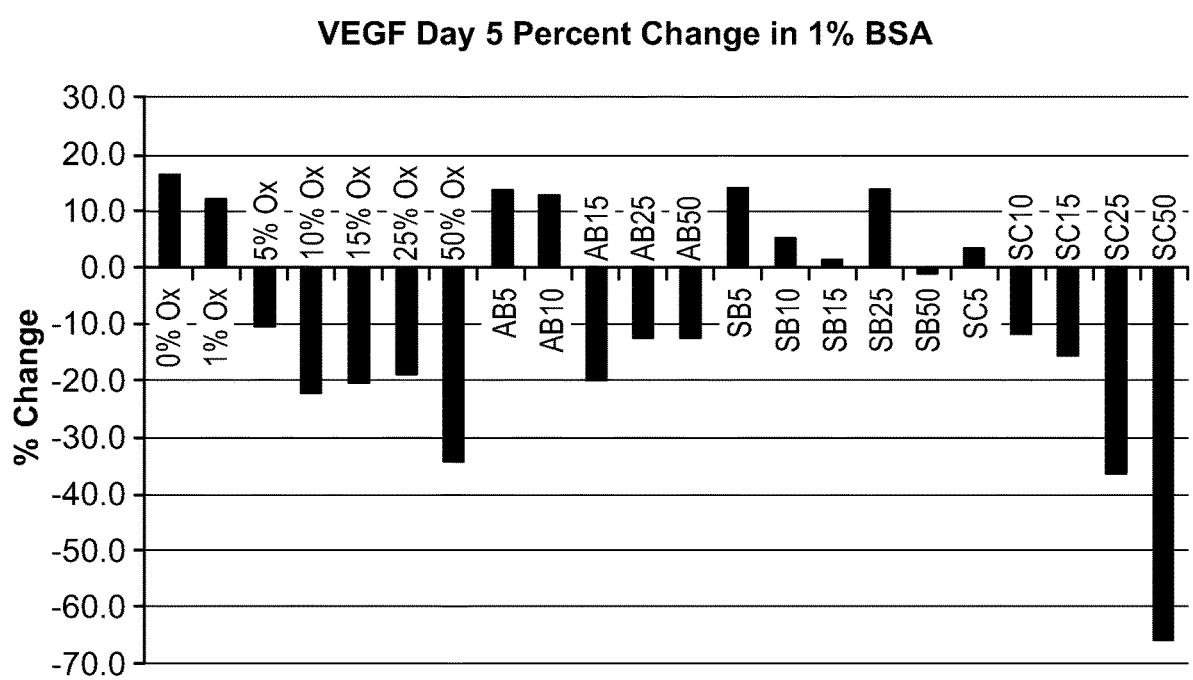
FIG. 4b is a bar graph showing % change in VEGF bioactivity measured by ELISA after 5 days of incubation in 1% BSA solution, illustrating the loss of VEGF bioactivity as a function of exposed to oxidized alginates.

The data is shown in FIGS. 4a and 4b. FIG. 4a shows % change in VEGF measured after 5 days of incubation in EBM. The data indicates that for oxidized alginates that have not been further processed, the % change in VEGF is directly correlated with the percent of aldehydes contained in alginate (see first 7 bars from the left, labeled as "0", "1", "5", "10", "15", "25" and "50"). The % change in VEGF reaches 100% for alginates containing 25% and 50% of aldehydes. The data also indicates that % change in VEGF is significantly reduced for oxidized alginates that have been reacted with ammonia borane (see bars labeled as "AB5", "AB10", "AB15", "AB25" and "AB50"), with the highest % change of about 60% in VEGF seen for the alginate containing 15% of aldehydes. Reduction with sodium borohydride is not as effective at protecting VEGF, with higher % change in VEGF seen for each studied alginate material (see bars labeled as "SB5", "SB10", "SB15", "SB25" and "SB50"). Oxidation with sodium chlorite resulted in significant % change measured for all studied samples (see bars labeled as "SC5", "SC10", "SC15", "SC25" and "SC50"), due to the residual aldehydes maintained by reaction inefficiency at the time (initial DMSO reaction conditions).

FIG. 4b shows % change in VEGF measured after 5 days of incubation in 1% BSA solution. The data indicates that % change in VEGF can reach more than 30% for oxidized alginate materials that have not been further processed (see first 7 bars from the left, labeled as "0% Ox", "1% Ox", "5% Ox", "10% Ox", "15% Ox", "25% Ox" and "50% Ox"). Reductive processing with ammonia borane (see bars labeled as "AB5", "AB10", "AB15", "AB25" and "AB50") or sodium borohydride (see bars labeled as "SC5", "SC10", "SC15", "SC25" and "SC50") reduced % change in VEGF, with sodium borohydride being more effective than ammonia borane. Oxidative processing with sodium chlorite (initial DMSO reaction conditions) resulted in an increase in % change in VEGF (see bars labeled as "SC5", "SC10", "SC15", "SC25" and "SC50"), as compared to controls.

The data shown in FIGS. 4a and 4b indicate that there are differences in the ability of variously processed alginates to protect protein cargo.

Example 4. The Degree of Click Reagent Substitution is Increased for Oxidized Alginates after Reaction with Sodium Chlorite The purpose of this experiment was to determine if the degree of click reagent conjugation with a click reagent may be increased following reaction of oxidized alginates with sodium chlorite. As shown in FIG. 1a, click reagents may be typically conjugated to alginates via the carboxylate moiety present in the glucuronic acid in an alginate, resulting in one click molecule per alginate monomer. Following alginate oxidation with sodium periodate, two aldehyde reagents are generated per alginate monomer, which may also be conjugated to a click reagent via an imine bond (FIG. 1b). This conjugation of click reagents to oxidized alginates is suboptimal because of residual aldehydes that remain in the alginate following conjugation that may result in toxicity and damage to cargo, as well as degradation of the click reagents (see examples 1 and 3). Further, the imine bonds between the aldehydes and the click reagents are easily hydrolyzable, resulting in the loss of click reagents from the alginate. However, as shown in FIG. 1c, further oxidation of aldehydes present in oxidized alginates converts these aldehydes to carboxylic acids provides two additional sites for click conjugation.

In order to determine if further oxidation of oxidized alginates can increase click conjugation, alginate reacted with sodium periodate only, or alginate oxidized with sodium periodate (HighOx alginate) and further oxidized with sodium chlorite (alginate containing algoxalate) were conjugated with click reagents tetrazine (Tz) and norbornene (Nb), and the relative amounts of conjugated tetrazine and norbornene were compared. To this end, alginate was oxidized using sodium periodate and SC using the procedure described in Examples 1 and 2. These products were then modified with either 1-bicyclo[2.2.1]hept-5-en-2-ylmethanamine (Norbornene Methanamine; TCI) or 3-(p-benzylamino)-1,2,4,5-tetrazine. First, the SC treated alginate was dissolved in stirred buffer containing 0.1 M MES, 0.3 M NaCl, pH 6.5 at the concentration of 0.5% w/v. Next, N-hydroxysuccinimide (NHS; Sigma-Aldrich) and 1-ethyl-3-(3-dimethylaminopropyl)-carbodiimide hydrochloride (EDC; Sigma-Aldrich) were added in 5× molar excess of the carboxylic acid groups present on the alginate. Either norbornene (Nb) or tetrazine (Tz) was then added at defined molar ratios of Nb or Tz to alginate monomer to yield Alg-N or Alg-T, respectively. The coupling reaction was stirred at room temperature overnight, and the product is purified by Tangential Flow Filtration (TFF) or dialyzed using 12-14 kDa MWCO dialysis tubing (Spectrum Labs) overnight with extensive water changes against a decreasing salt gradient from 150 mM to 0 mM NaCl in diH$_2$O. The purified Alg-N and Alg-T polymers were then treated with activated charcoal, sterile filtered (0.22 mm), and freeze-dried. This resulted in purified Alg-N or Alg-T polymers with various degrees of substitution of the available carboxylic acid groups of alginate.

Figure 5A:
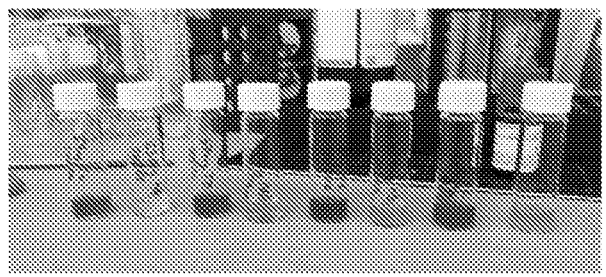
FIG. 5a is a panel of two pictures of vials containing HighOx alginates conjugated to Tz and Nb at day 0 (top panel) and HighOx Sc alginates conjugated to Tz and Nb at day 0 (bottom panel), illustrating the apparent change in click conjugates due to the presence of aldehydes in oxidized alginates and the lack of change in the conjugates containing algoxinol and algoxalate.
Figure 5A:
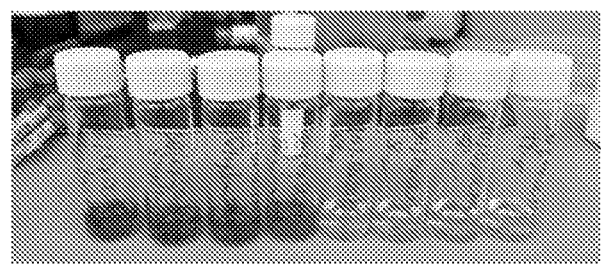
Figure 5B:
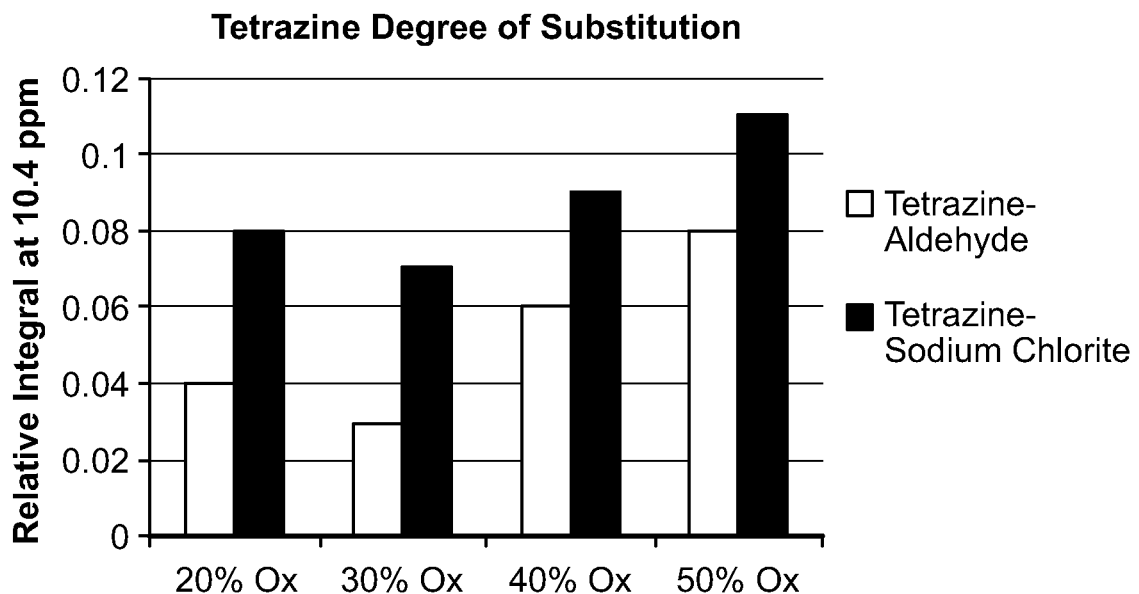
FIG. 5b is a bar graph showing relative amounts of Tz present in HighOx and HighOx SC alginates as measured by NMR, illustrating the additional potential for click conjugation of the algoxalate containing alginate via the additional carboxylic acid moieties.

FIG. 5a shows pictures of vials containing HighOx alginates conjugated to Tz and Nb at day 0 (top panel) and HighOx Sc alginates conjugated to Tz and Nb at day 0 (bottom panel). Tz- and Nz-conjugated material is nominally pink/red and slightly off clear, respectively. FIG. 5b shows relative amounts of Tz present in HighOx and HighOx SC alginates, measured by NMR. The data indicate that there is a 1.4 to 2.3 times more Tz molecules conjugated to HighOx SC alginate, as compared to the HighOx alginate, for alginates containing 20-50% oxidation, indicating that the alginate containing algoxalate has an extended conjugation potential.

Example 5. Characterization of Click Conjugated Oxidized Alginates

The purpose of this experiment was to characterize the properties of click conjugated HighOx SC alginate material and compare it with the properties of click conjugated HighOx alginate material. The stability of both alginate materials was investigated by UV-Vis spectral analysis. The data for Tz-conjugated materials is shown in FIGS. 6a and 6b. FIG. 6a shows a UV-Vis spectrum of Tz-conjugated HighOx alginate material with 20-50% oxidation at day 28 (top panel) and a UV-Vis spectrum of Tz-conjugated HighOx SC material with 20% and 30% conjugation at day 14. FIG. 6b also shows pictures of vials containing these Tz-conjugated HighOx and the HighOx SC alginate materials. The data indicates that tetrazine conjugated HighOx alginate material loses the characteristic Tz peak at 515 nm at 28 days, while this peak is still present at day 14 in HighOx SC alginate material containing 20% and 30% oxidation. These data suggest that the sodium chlorite processed tetrazine conjugated material exhibits greater stability in solution.

Figure 6C:
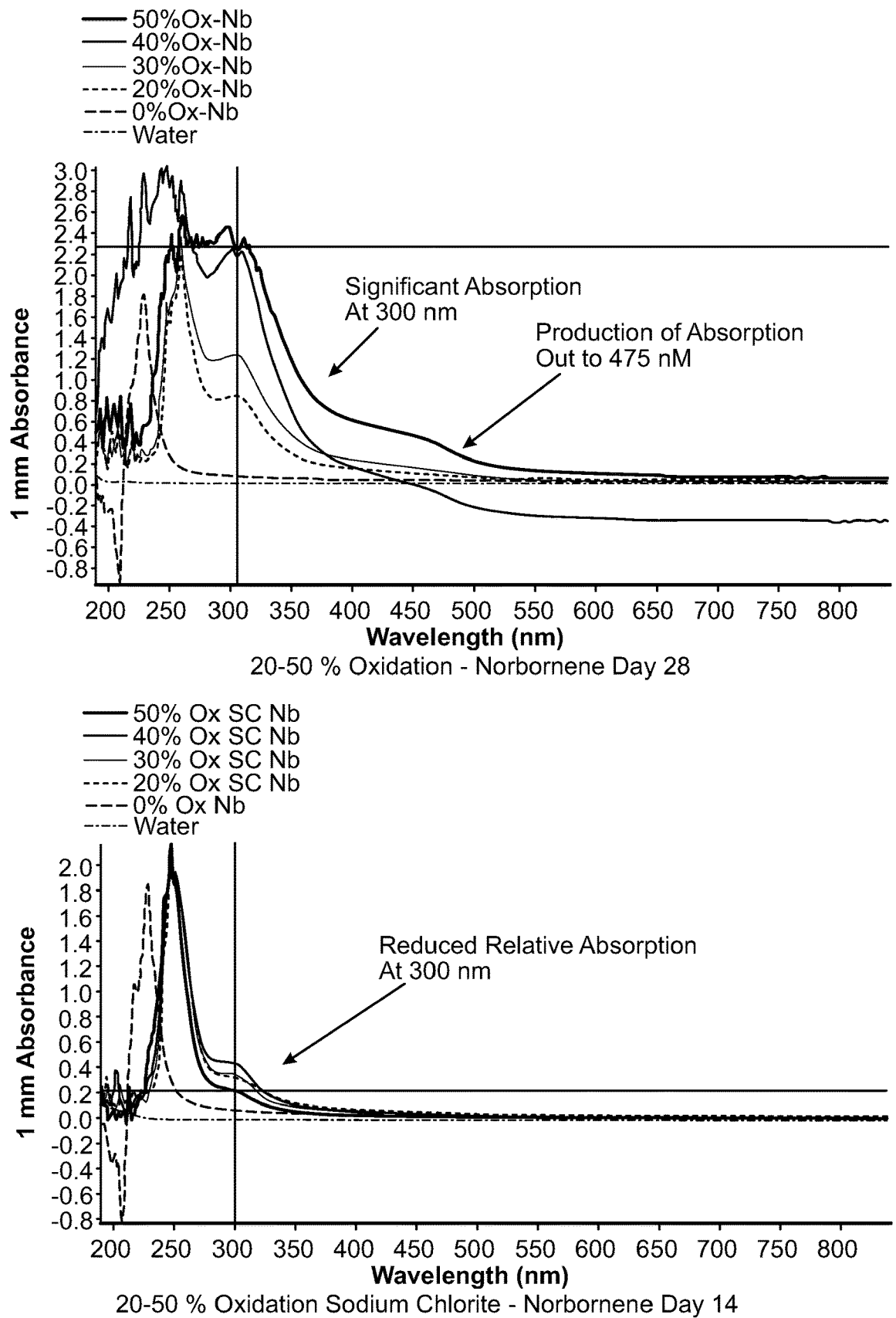
FIG. 6c is a UV-Vis spectrum of Nb-conjugated HighOx alginate material with 20-50% oxidation at day 28 (top panel) and a UV-Vis spectrum of Nb-conjugated HighOx alginate material treated with sodium chlorite, containing 20%-50% conjugation at day 14.
Figure 6D:
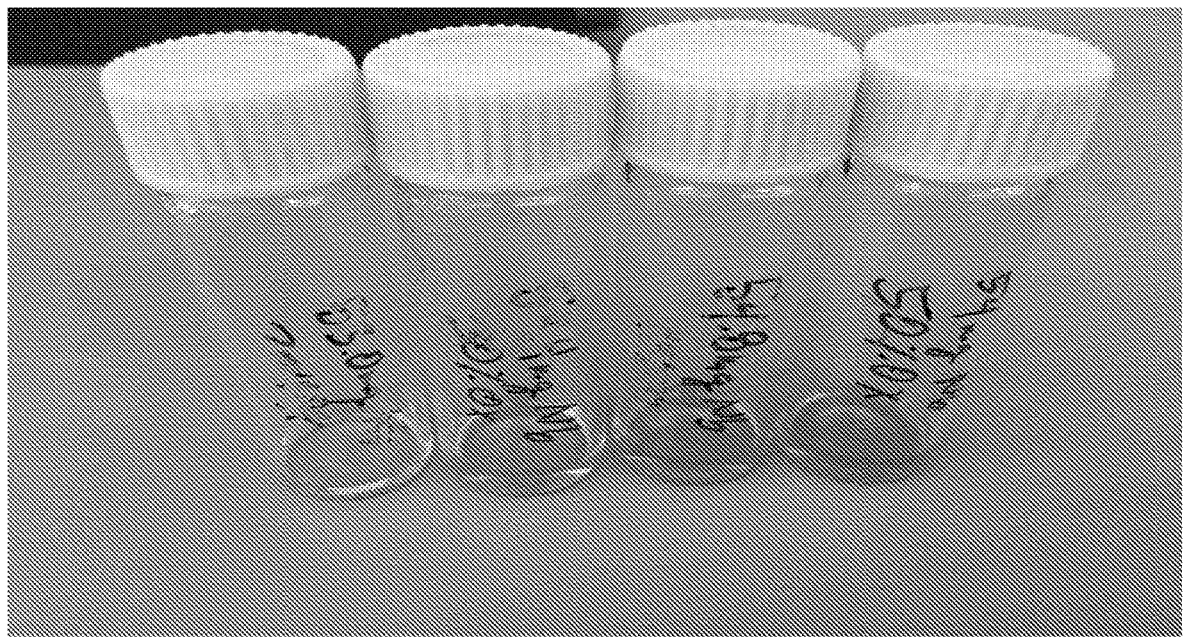
FIG. 6d is a panel of two pictures of vials containing Nb-conjugated HighOx alginate material with 20-50% oxidation at day 28 (top panel) and Nb-conjugated HighOx alginage material treated with sodium chlorite containing 20%-50% conjugation at day 14 (bottom panel).
Figure 6D:
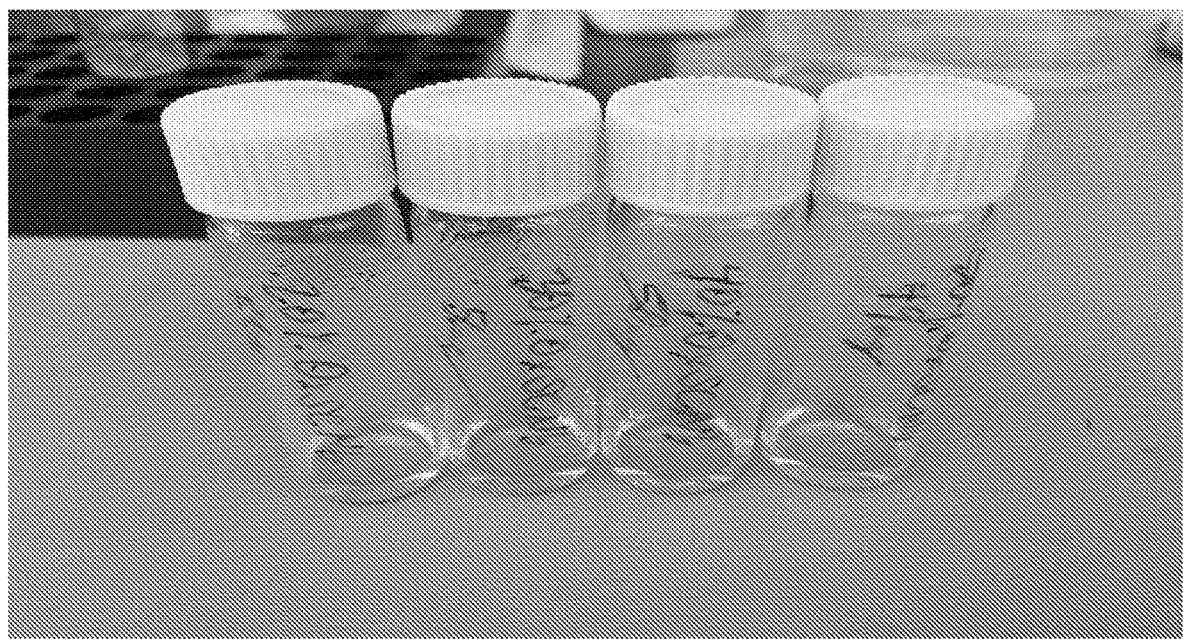
Figure 6E:
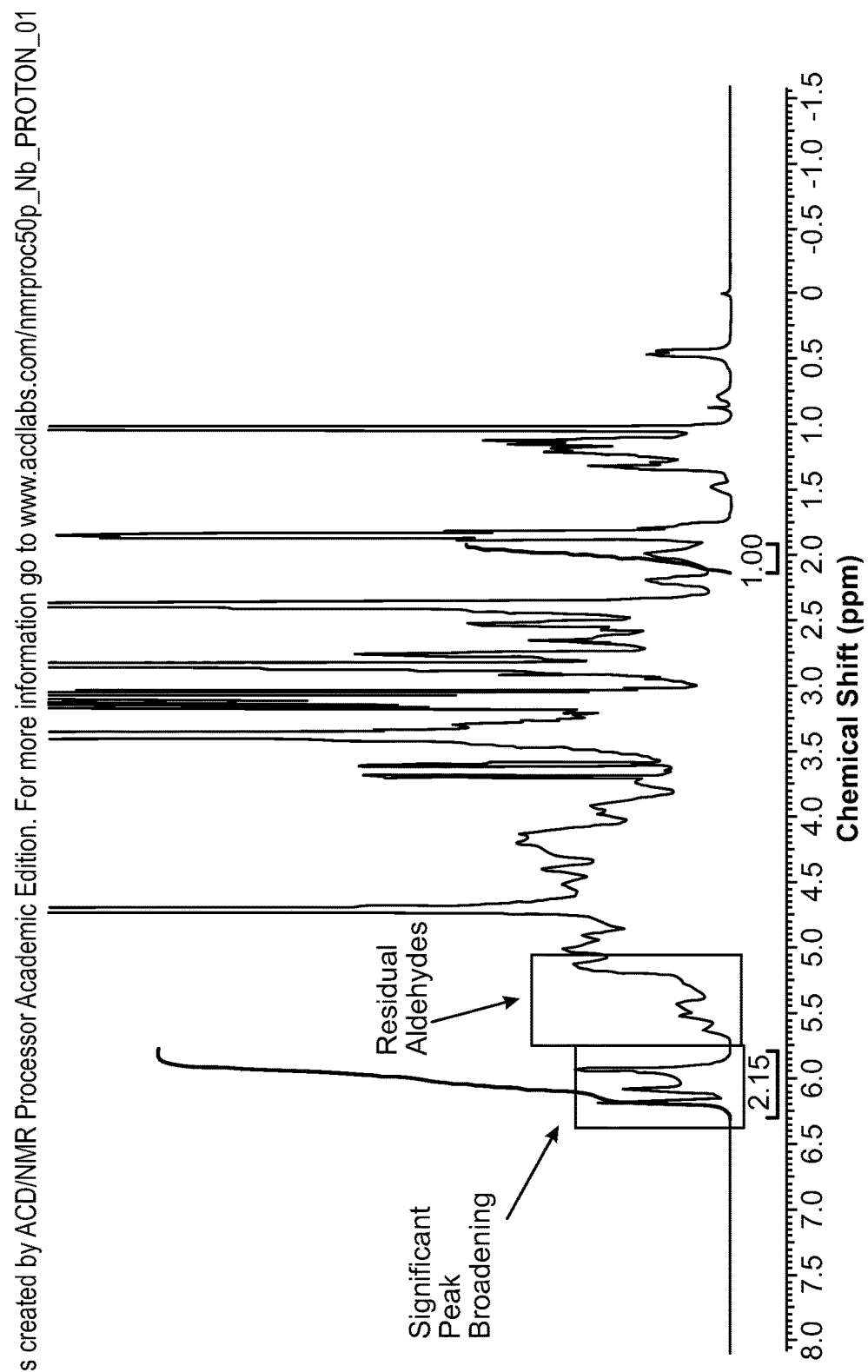
FIG. 6e is an NMR spectrum of Nb-conjugated alginate material that has been oxidized with sodium periodate, showing the broadening of Nb peaks as well as the presence of aldehyde peaks.
Figure 6F:
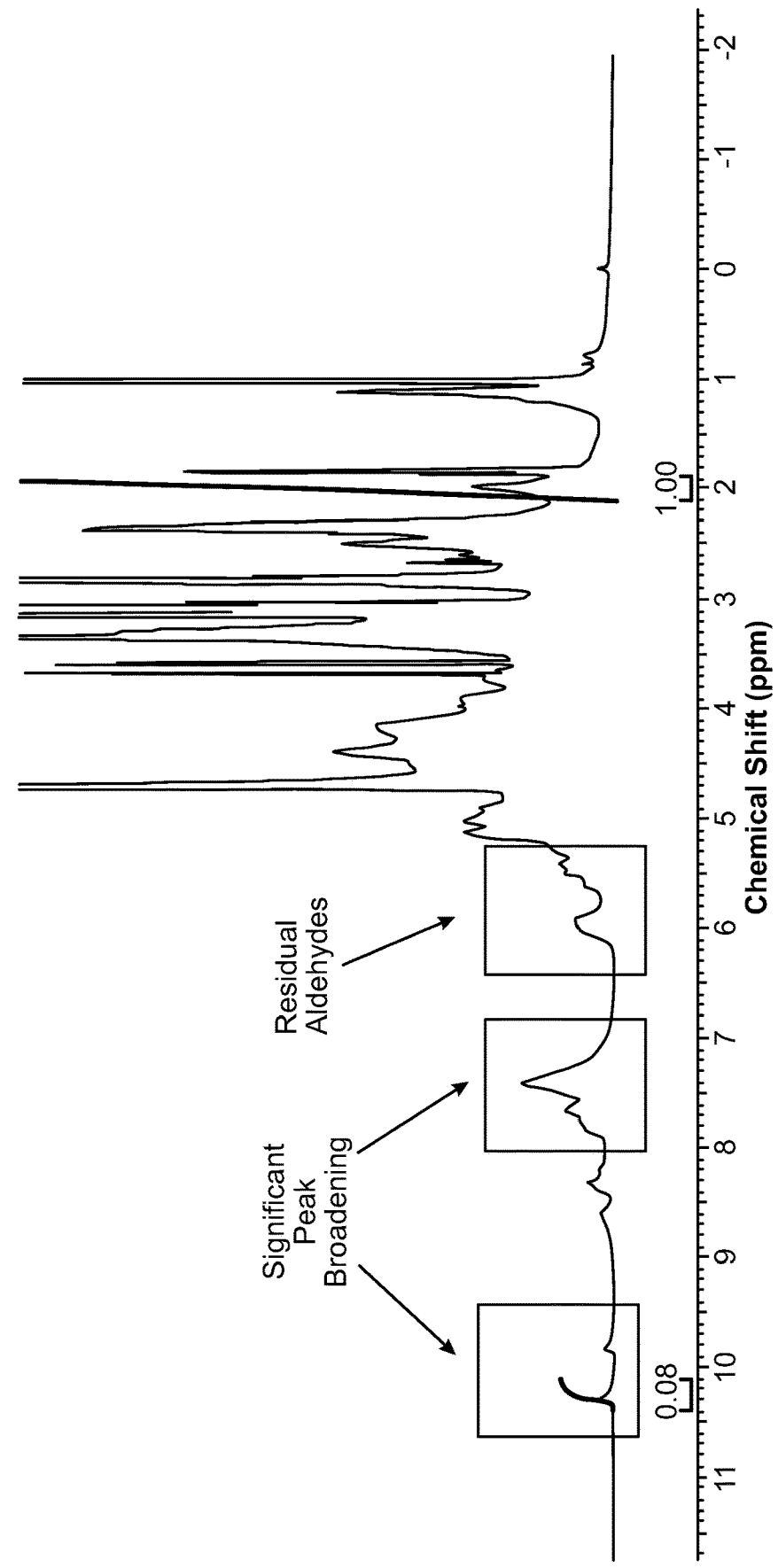
FIG. 6f is an NMR spectrum of Tz-conjugated alginate material that has been oxidized with sodium periodate, showing the broadening of Nb peaks and the presence of aldehyde peaks.
Figure 6G:
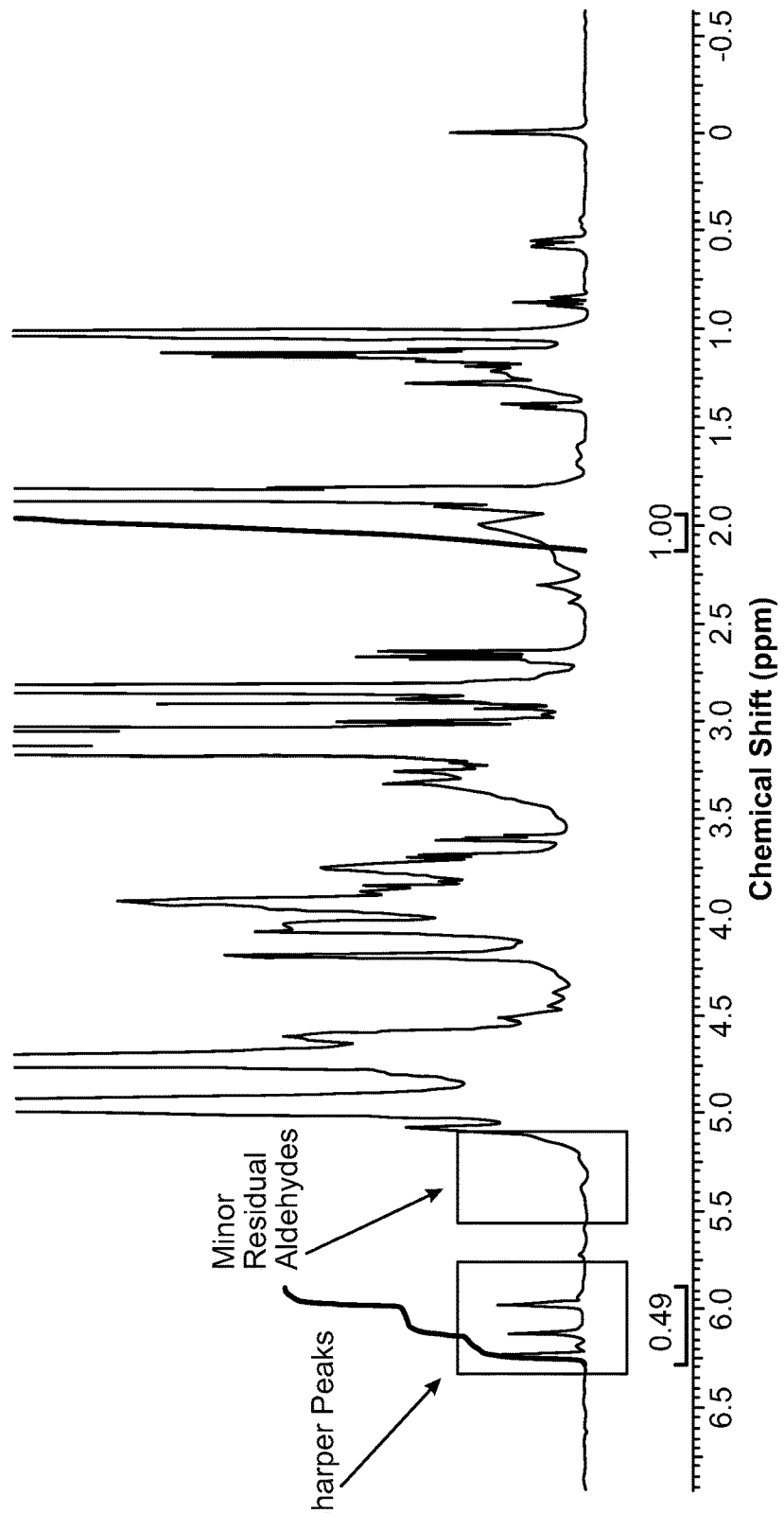
FIG. 6g is an NMR spectrum of Nb-conjugated alginate material that has been oxidized with sodium periodate and then further oxidized with sodium chlorite, showing the lack of broadening of Nb peaks and the absence of aldehyde peaks.
Figure 6H:
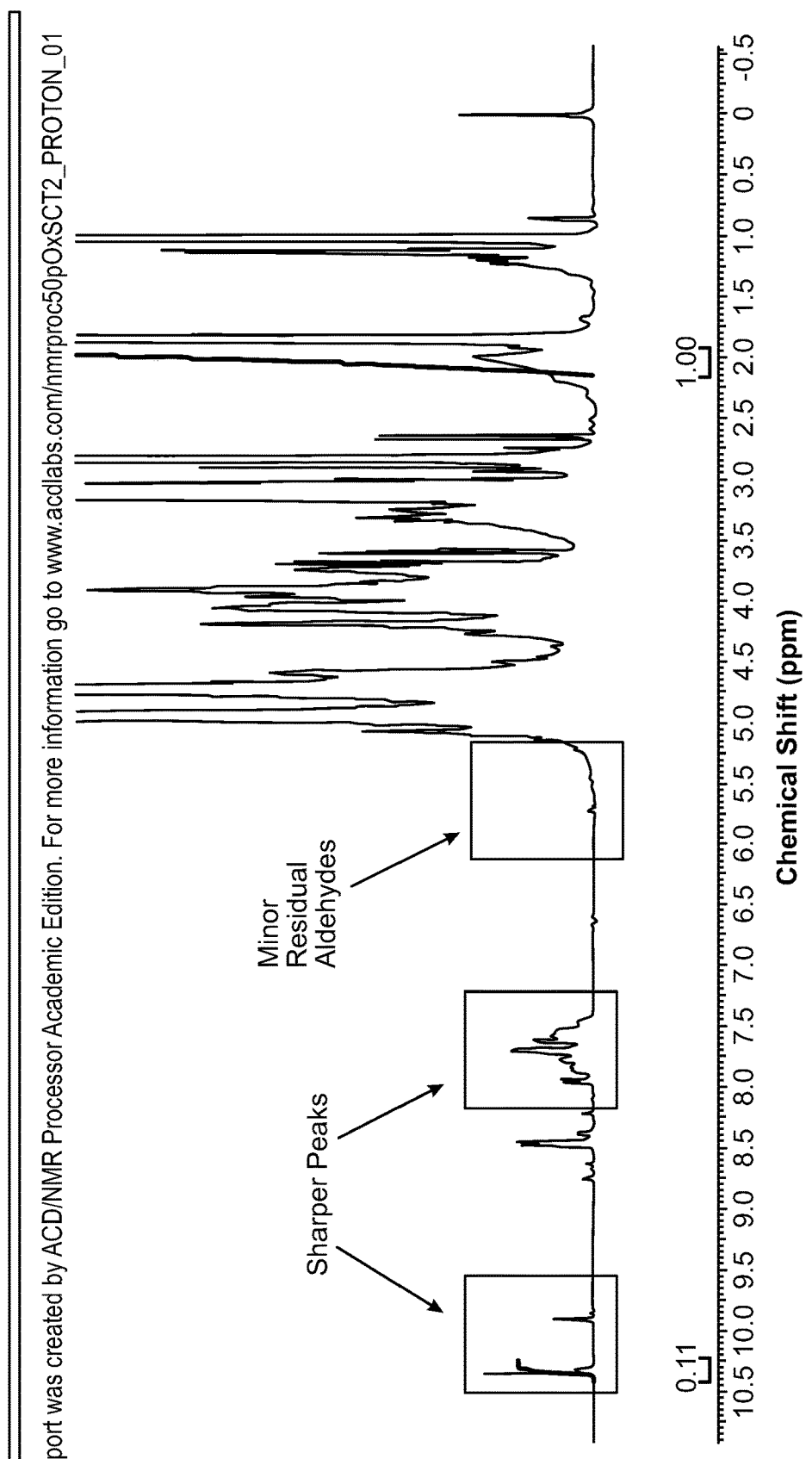
FIG. 6h is an NMR spectrum of Tz-conjugated alginate material that has been oxidized with sodium periodate and then further oxidized with sodium chlorite, showing the lack of broadening of Nb peaks and the absence of aldehyde peaks . . . .
Figure 6I:
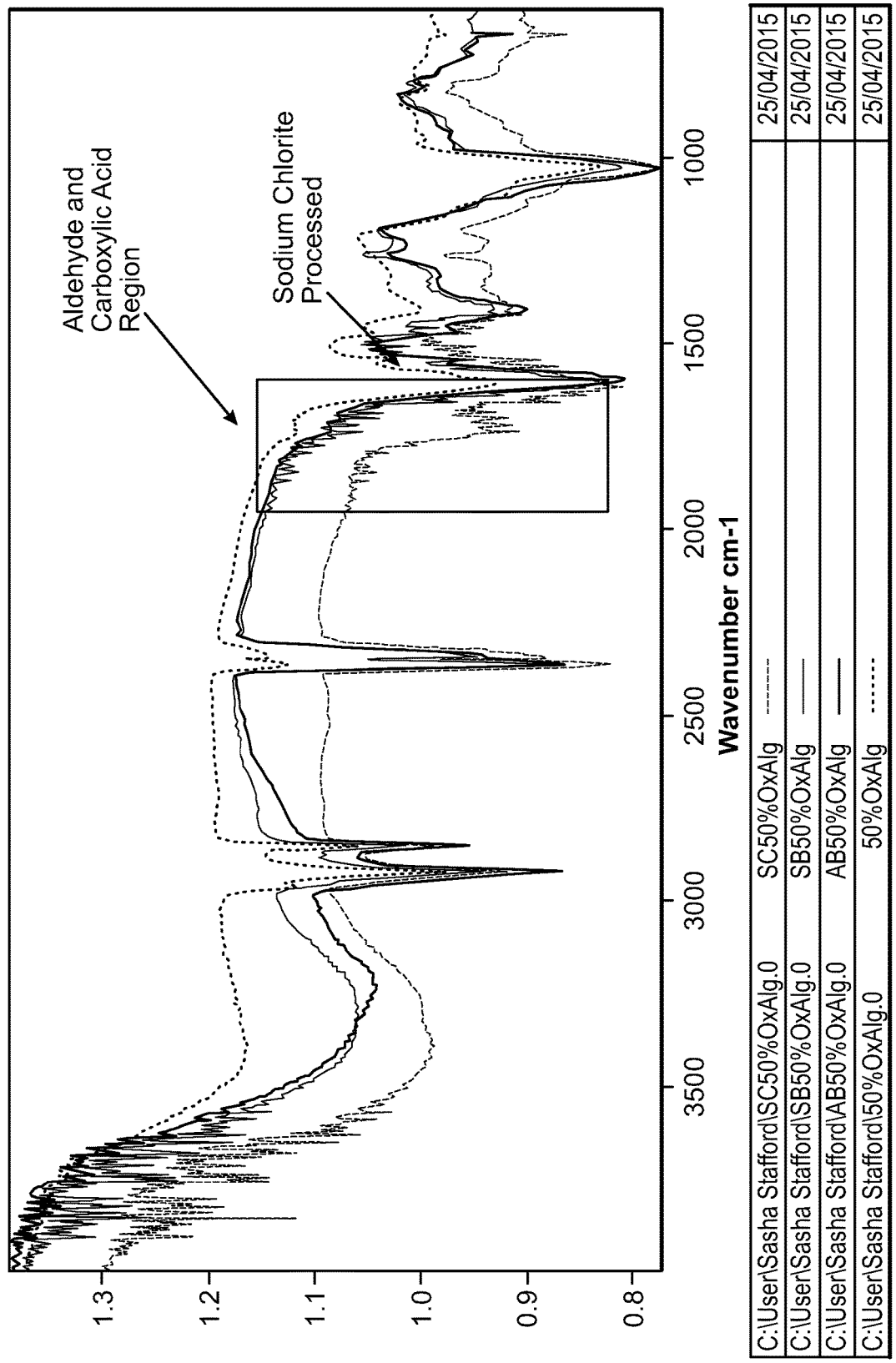
FIG. 6i is a representative FTIR spectrum of the alginate material, demonstrating the production of carboxylic acid peaks following the treatment with sodium chlorite.

The data for Nb-conjugated materials is shown in FIGS. 6c and 6d. FIG. 6c shows a UV-Vis spectrum of Nb-conjugated HighOx alginate material with 20-50% oxidation at day 28 (top panel) and a UV-Vis spectrum of Nb-conjugated HighOx SC material with 20%-50% conjugation at day 14. FIG. 6d also shows pictures of vials containing these Nb-conjugated HighOx and the HighOx SC alginate materials. The data indicates that a plateau at 475 nm is produced in HighOx alginate material at day 28, while this peak is absent in the HighOx SC alginate material at day 14. The HighOx SC alginate material is also characterized by a reduced absorption at 300 nm. These data suggest that the Sodium Chlorite processed norbornene conjugated material exhibits greater stability in solution.

Figure 6J:
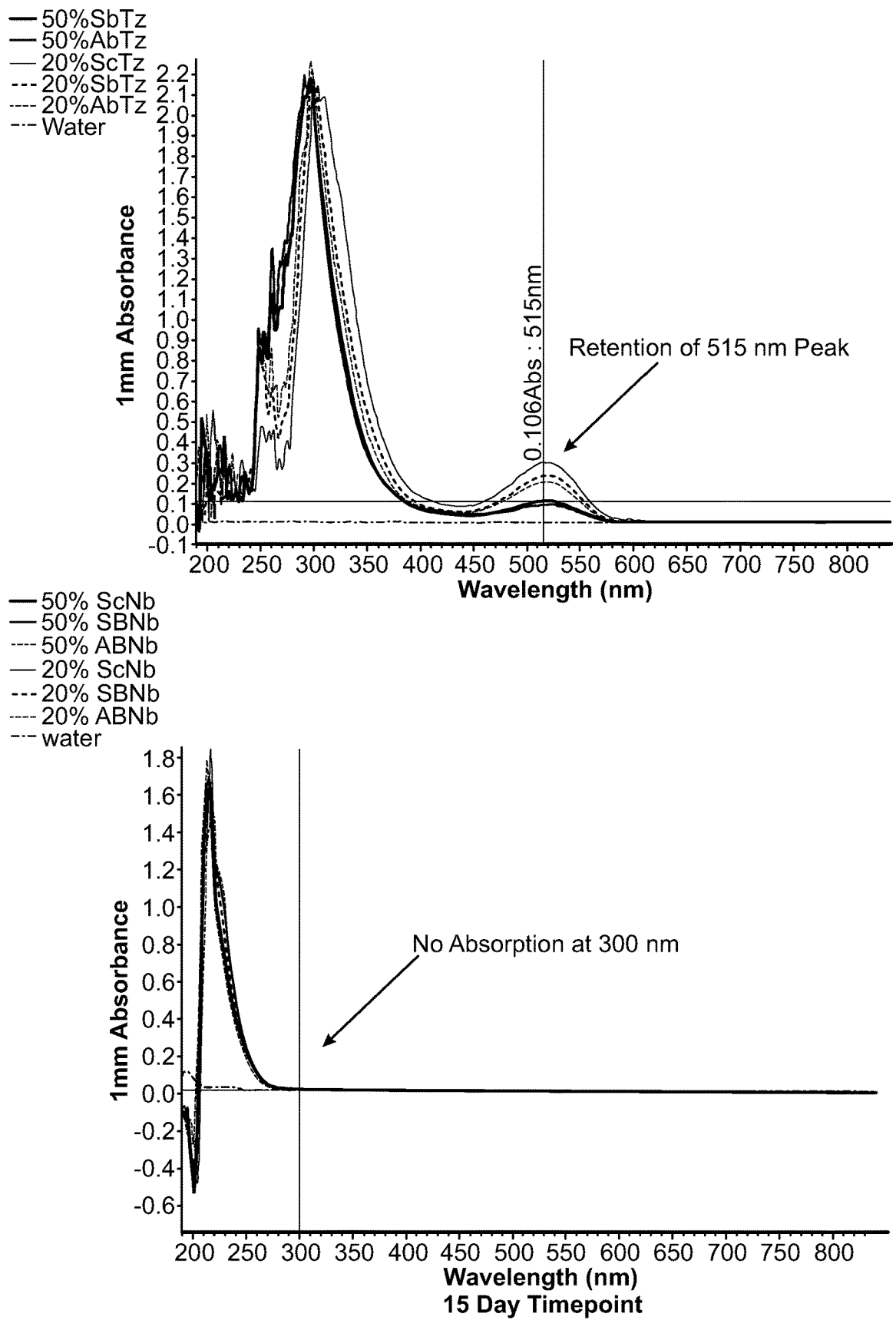
FIG. 6j is a UV-Vis spectra for Tz-conjugated and Nb-conjugated alginate materials at day 15, showing the lack of color change for click conjugated alginates containing algoxinol and algoxalate.
Figure 6K:
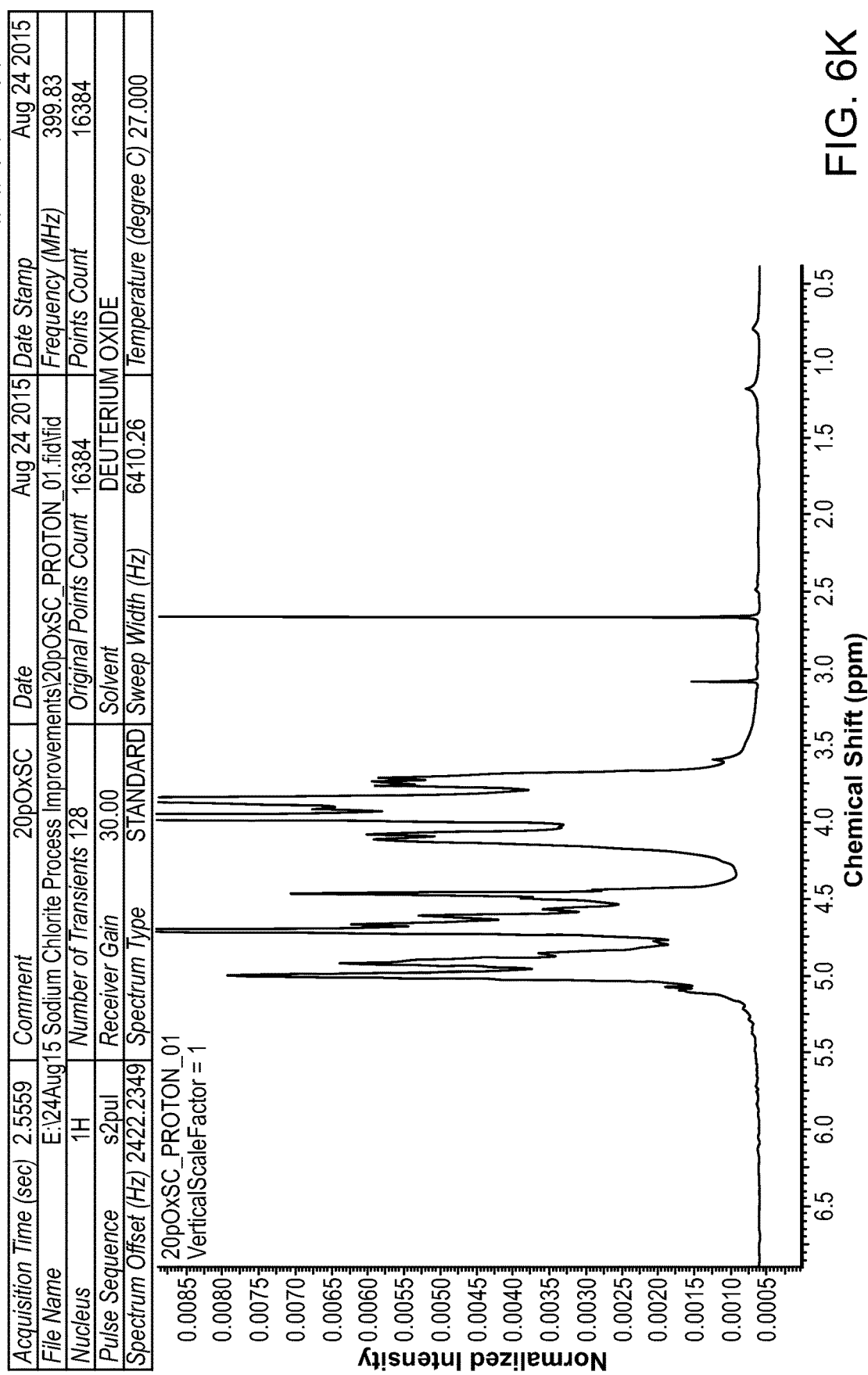
FIG. 6k is an NMR spectra for the alginate material that has been oxidized with sodium periodate and further oxidized with sodium chlorite, showing the absence of aldehyde associated peaks (~≥5.1 ppm).
Figure 6K:
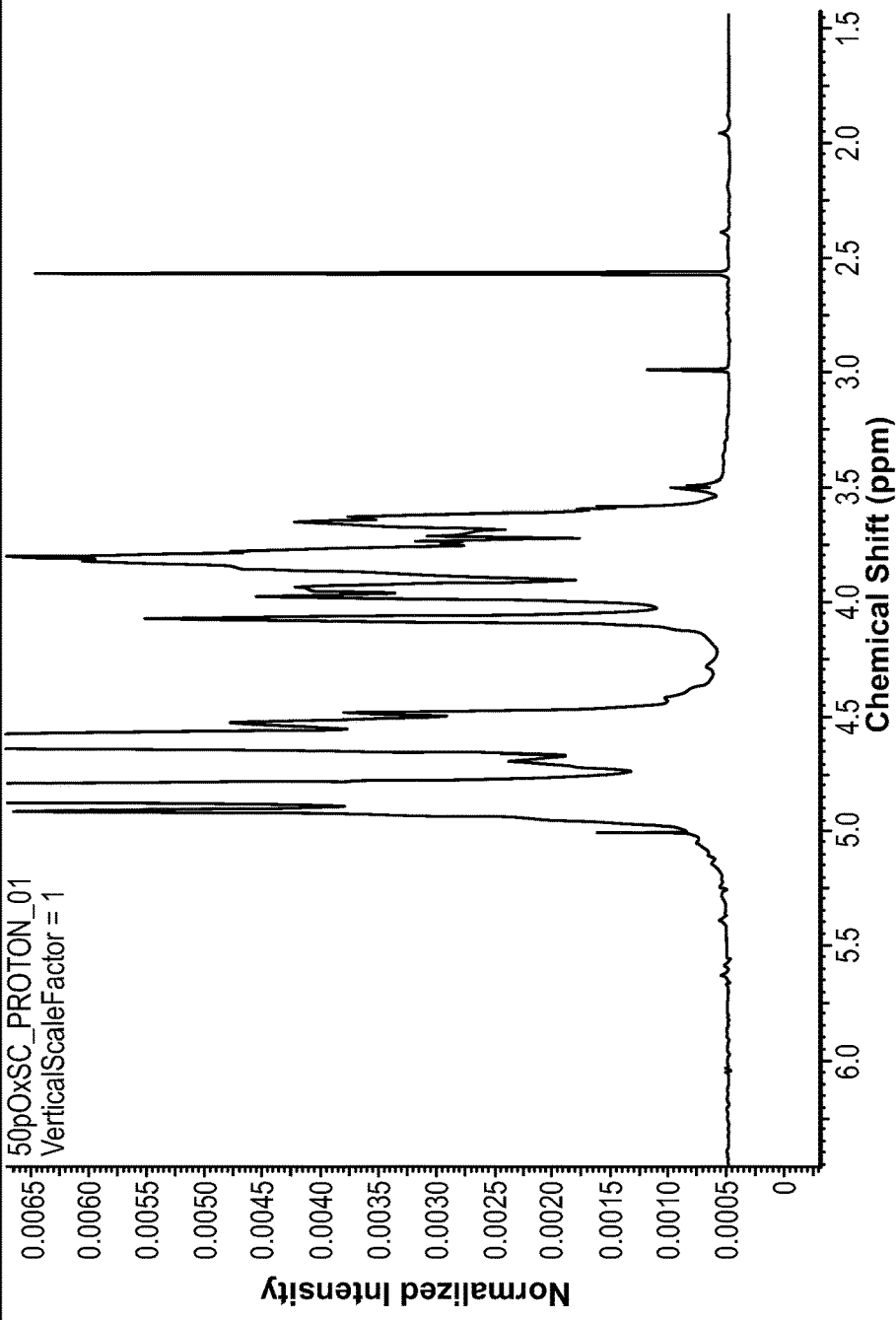

The UV-Vis spectra for Tz-conjugated and Nb-conjugated HighOx (20% and 50% aldehyde) ammonia borane (AB), sodium borohydride (SB), and sodium chlorite (SC) alginate materials at day 15 (4% w/v solutions stored at room temperature) are shown in FIG. 6j. The spectra indicate that after 15 days the peak at 515 nm for Tz-conjugated HighOx material is retained, and that there is no absorption at 300 nm for the Nb-conjugated HighOx material. This data indicates that reduction or further oxidation of the alginate aldehydes confers greater stability of the click conjugated moieties in solution.

The Tz-conjugated and Nb-conjugated HighOx and HighOx SC materials were also investigated by quantitative NMR to determine their aldehyde content. Quantification of the aldehyde content was performed on a Varian 400 MHz by comparing the proton peaks generated by sodium periodate at >~5.1 ppm to an internal standard of Dimethylmalonic Acid (DMMA; 6H @ 1.3 pmm; Sigma-Aldrich). Samples were prepared at 15 mg/mL alginate and 2.5 mg/mL DMMA in deuterium oxide (D$_2$O; Sigma-Aldrich).

The results are shown in FIGS. 6e, 6f, 6g and 6h. Specifically, FIGS. 6e and 6f show NMR spectra of HighOx alginate material with 50% oxidation conjugated to Nb and Tz, respectively. FIGS. 6g and 6h show NMR spectra of of HighOx SC alginate material with 50% aldehyde conjugated to Nb and Tz, respectively. The data indicate that there is a significant peak broadening in HighOx aldehyde alginate material, indicating that this material is more dynamic. The NMR spectra for HighOx alginate material also contain peaks indicating presence of residual aldehydes. In contrast, the NMR spectra for HighOx SC alginate material show sharp peaks, indicating greater definition in the HighOx SC material, and a near absence of residual aldehydes. The absence of residual aldehydes in HighOx SC alginate material is also confirmed by the FTIR analysis, with the FTIR spectrum shown in FIG. 6i. Overall, the data indicate that click-conjugated HighOx SC alginate material is less dynamic, more chemically stable and contains only minor amounts of residual aldehydes.

The reaction conditions of oxidized alginate with sodium chlorite were evaluated. Initial reaction conditions used to generate the data shown in FIG. 3b used a mixture of 1:1 water:DMSO as a solvent, where DMSO was used as a scavenger for the hypochlorous acid (HOCl), a by-product. By changing the DMSO content in the mixture to 33:1 water:DMSO, the reaction was driven further to completion. The NMR spectrum for the HighOx SC alginate material produced at optimal conditions is shown in FIG. 6k demonstrating that there are not any significant residual aldehydes in the material with 20% and 50% oxidation after further processing the aldehydes with sodium chlorite under these conditions.

Example 6. Gelation of Click Conjugated Oxidized Alginates

Click conjugated HighOx and HighOx SC material with 20-50% oxidation was investigated for the ability to form a hydrogel. Preparations of complimentary degrees of oxidation (e.g. 20% aldehyde-TZ and 20% aldehyde-Nb) were made at 10% (w/v), mixed and allowed to gel for 20 minutes. FIGS. 8a and 8b demonstrate that periodate oxidized, reduced (AB, SB) and further oxidized (SC) materials degrade as a function of time in solution (e.g. dialysis residence time), which limits hydrogel formation. Thus, in order to potentiate gelation, the process has been modified to replace dialysis with tangential flow filtration (TFF) in order to minimize solution residence time.

FIG. 8c demonstrates that the solubility of the HighOx and HighOx SC material increases as a function of % oxidation and is highest for the HighOx SC material.

Example 7. In Vitro Degradation and Solubility of Oxidized and Reduced Alginates The purpose of this experiment was to investigate the degradation and solubility of oxidized alginates with and without click conjugation after further reductive processing (i.e., reaction with sodium borohydride or ammonia borane) or oxidative processing (i.e., reduction with sodium chlorite).

Click conjugated alginate material (MVG alginate, 280 kDa) was prepared by reacting alginate with sodium periodate, followed by precipitation with tetrahydrofuran (THF). The precipitated material was then reduced by reacting it with either sodium borohydride or ammonia borane, or further oxidized by reacting it with sodium chlorite, and further dialyzed for 1 day. It was then conjugated with Tz or Nb, and dialyzed again for 1 day.

Control alginate materials not conjugated with clicks (VLVG alginate, 30 kDa) was prepared by reacting alginate with sodium periodate, followed by a 3-day dialysis. The dialyzed material was then reduced by reacting it with either sodium borohydride or ammonia borane, or further oxidized by reacting it with sodium chlorite, and further dialyzed for 3 days.

The MVG and VLVG alginate materials were then incubated at 37° C. for up to 29 days, and were analyzed by gel permeation chromatography (GPC) to determine the average molecular weight of the alginate material. To this end, samples were prepared in PBS at the concentration of the alginate material of 2 mg/mL. The samples were then analyzed using Agilent 1260 HPLC equipped with G4000PWx1 and G5000PWx1 columns in series. Analysis was conducted using 100 µL injections, with 0.5 mL/min flow rate, 0.1 M Sodium Nitrate (Sigma-Aldrich) mobile phase, with column and detector temperatures at 35° C. Samples were compared to a calibrated PEO standard (34 kDa; Agilent Technologies) using triple detection.

Figure 7A:
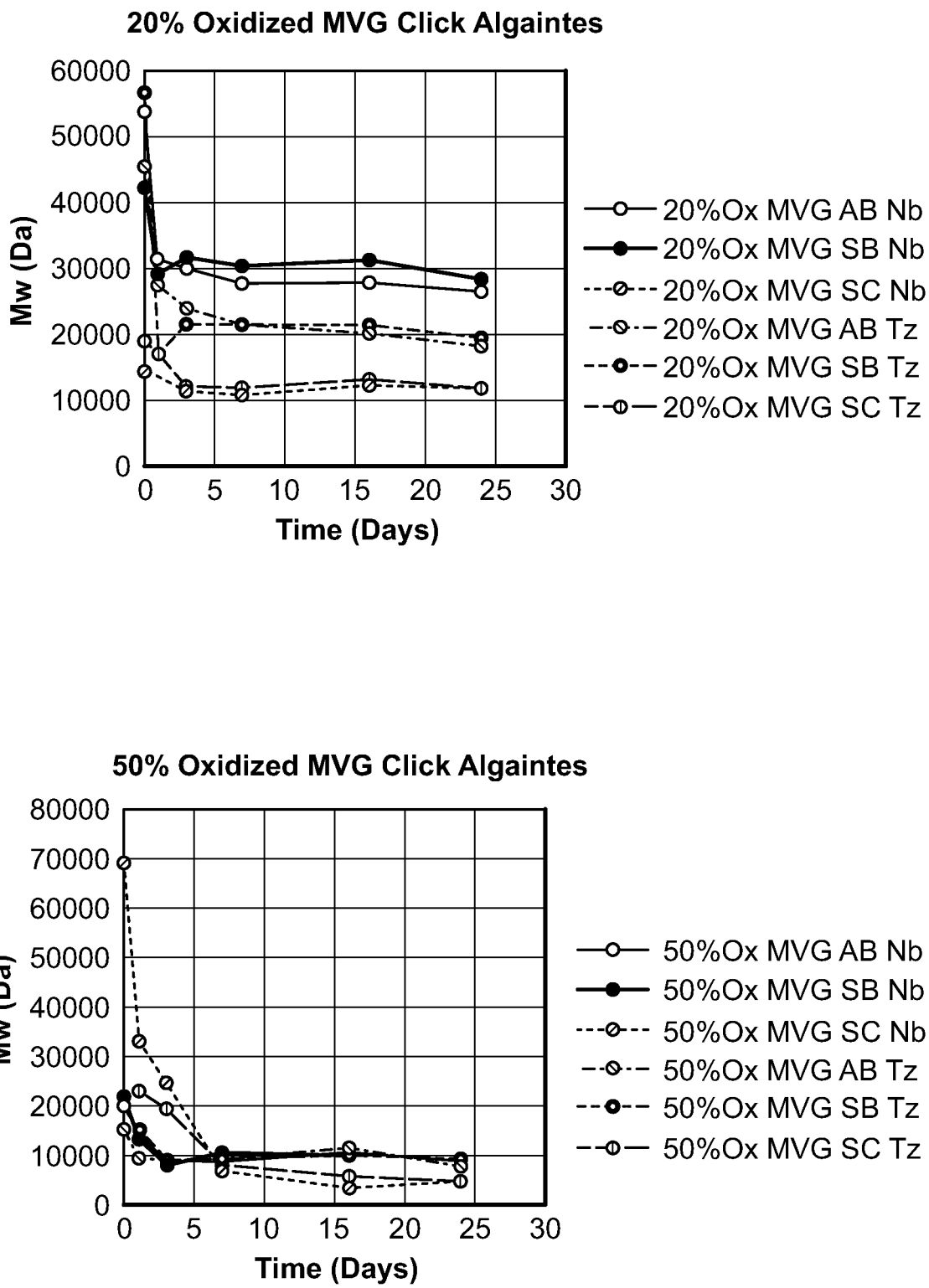
FIG. 7a is a panel of two graphs showing degradation of Tz-conjugated and Nb-conjugated MVG alginate (~250 kDa starting MW) with 20% oxidation (left panel) and 50% oxidation (right panel), showing hydrolysis of the alginate polymer backbone as a function of time.
Figure 7B:
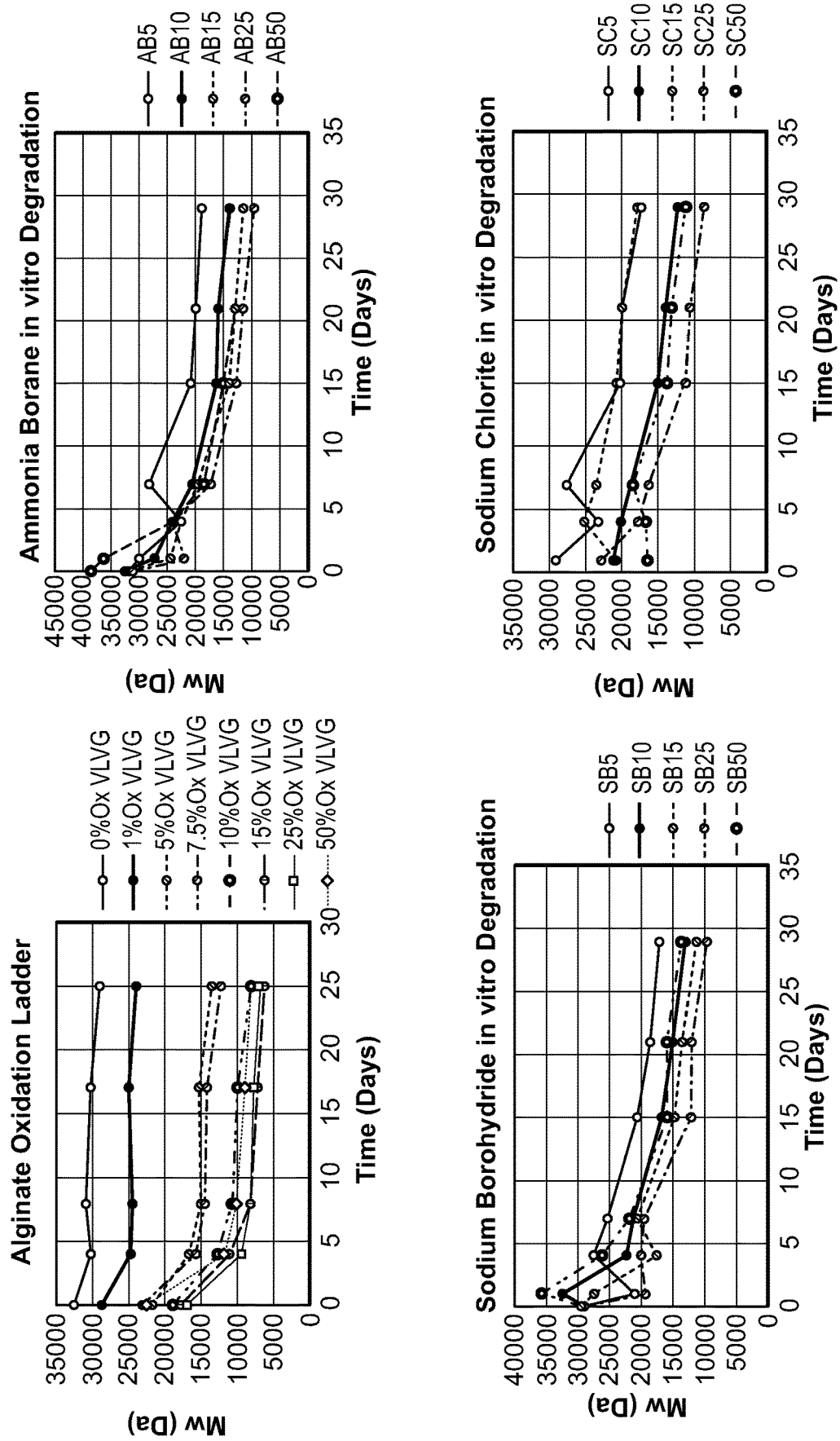
FIG. 7b is a panel of four graphs showing degradation of VLVG (30 kDa starting MW) alginate containing 0%-50% oxidation at 37° C. for non-processed alginate (upper left panel), alginate reductively processed with ammonia borane (upper right panel), alginate reductively processed with sodium borohydride (lower left panel), and alginate reductively processed with ammonia borane (lower right panel)), showing hydrolysis of the alginate polymer backbone as a function of time.

The results are shown in FIGS. 7a and 7b. Specifically, FIG. 7a shows degradation of Tz-conjugated and Nb-conjugated MVG alginate with 20% oxidation (left panel) and 50% oxidation (right panel). The data indicates that reductively processed MVG alginates (AB, SB) and further oxidized (SC) materials all exhibit degradability.

FIG. 7b shows degradation of VLVG alginate containing 0%-50% oxidation at 37° C. for non-processed alginate (upper left panel), alginate reductively processed with ammonia borane (upper right panel), alginate reductively processed with sodium borohydride (lower left panel) and alginate processed with sodium chlorite (lower right panel). The data indicate that reduced and further oxidized materials exhibit degradation profiles similar to the periodate oxidized material controls.

Figure 7C:
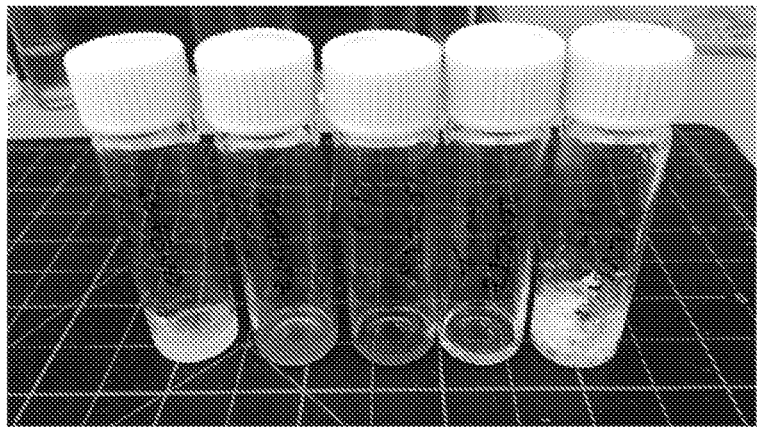
FIG. 7c is a picture of vials containing 50% w/v solutions of MVG and VLVG materials with 20% oxidation and unoxidized VLVG at 50% w/v for comparison. Unlike the parental alginate, the alginate material containing algoxinol and algoxalate show increased solubility.

FIG. 7c is a picture of vials containing 50% w/v solutions of MVG (280 kDa) materials with 20% oxidation processed with either ammonia borane or sodium chlorite. Unoxidized VLVG (30 kDa) at 50% (w/v) is provided as a control. Unoxidized MVG is only soluble to ~5% w/v, while unoxidized VLVG is soluble to ~10% w/v. Surprisingly, this photograph shows that both ammonia borane and sodium chlorite processed materials (having a molecular weight similar to VLVG, see FIG. 8a) are readily soluble at 50% w/v. The data indicate that Tz-conjugated and Nb-conjugated MVG materials that have been further oxidized with sodium chlorite are the most soluble.

Example 8. Upper Limit of Click Conjugation for Tetrazine and Norbornene

The purpose of this experiment was to determine the upper limit of click conjugation for the VLVG material prepared as described in Example 7. The MVG material, also prepared as described in Example 7, uses 250 molar equivalents of the click material in the conjugation reaction to obtain approximately 5% degree of substitution (DS), defined as the number of click moieties per monomer unit, with the upper limit for Tz being approximately 7.5%, and for Nb being 20%. In this experiment, the unoxidized VLVG material was reacted with different equivalents of Tz or Nb, and the % DS was measured by qNMR. The data is displayed in the table below. Norbornene NMR peaks broaden significantly at higher molar equivalence, thus values for norbornene are assumed to be over reported (OR).

| Equivalents of Click Reagent | % DS by qNMR |
| --- | --- |
| 600 eq tetrazine | 12.0 |
| 600 eq norbornene | 37.1 (OR) |
| 900 eq tetrazine | 12.9 |
| 900 eq norbornene | 72.9 (OR) |
| 1200 eq tetrazine | 21.8 |
| 1200 eq norbornene | 97.0 (OR) |

Figure 8:
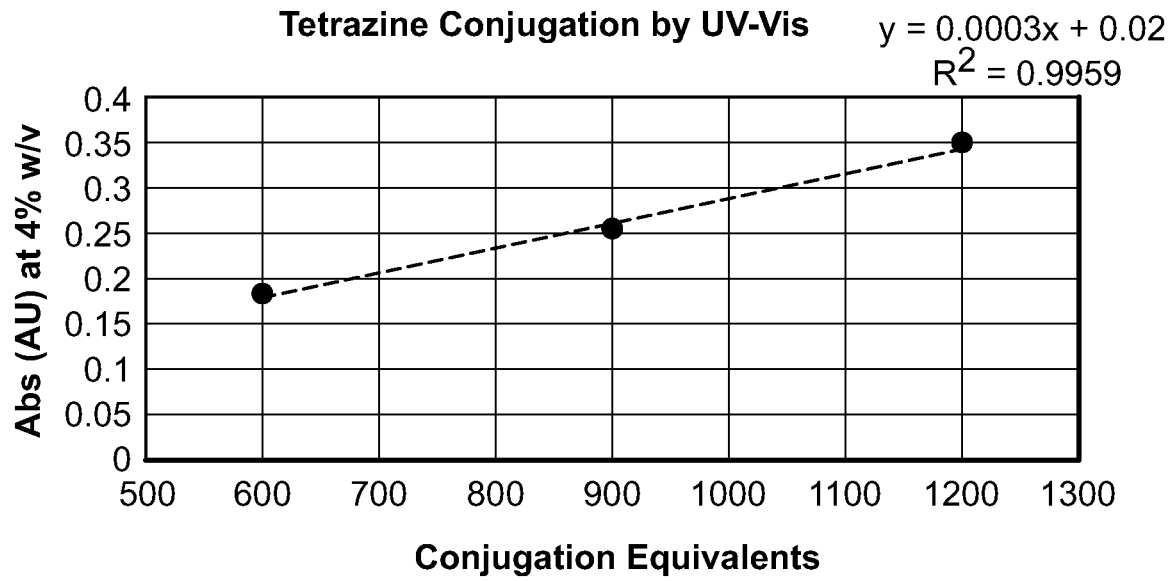
FIG. 8 is a graph showing UV-Vis absorption at 515 nm of Tz-conjugated alginate material versus the conjugation equivalents.

Tetrazine conjugation was also measured using UV-Vis spectrometry, as shown in FIG. 8. The data indicates that the degree of substitution for tetrazine is linear for the reaction with 600-1200 tetrazine equivalents. These data indicate that greater degrees of substitution can be obtained using lower molecular weight alginates and that the upper limit has not yet been reached. This experiment is extended to the reduced and further oxidized materials to determine the upper limit of their conjugation potential, and thus crosslinking density.

Example 9. Effect of Aldehydes Present in Oxidized Alginate on Cell Viability

Figure 9:
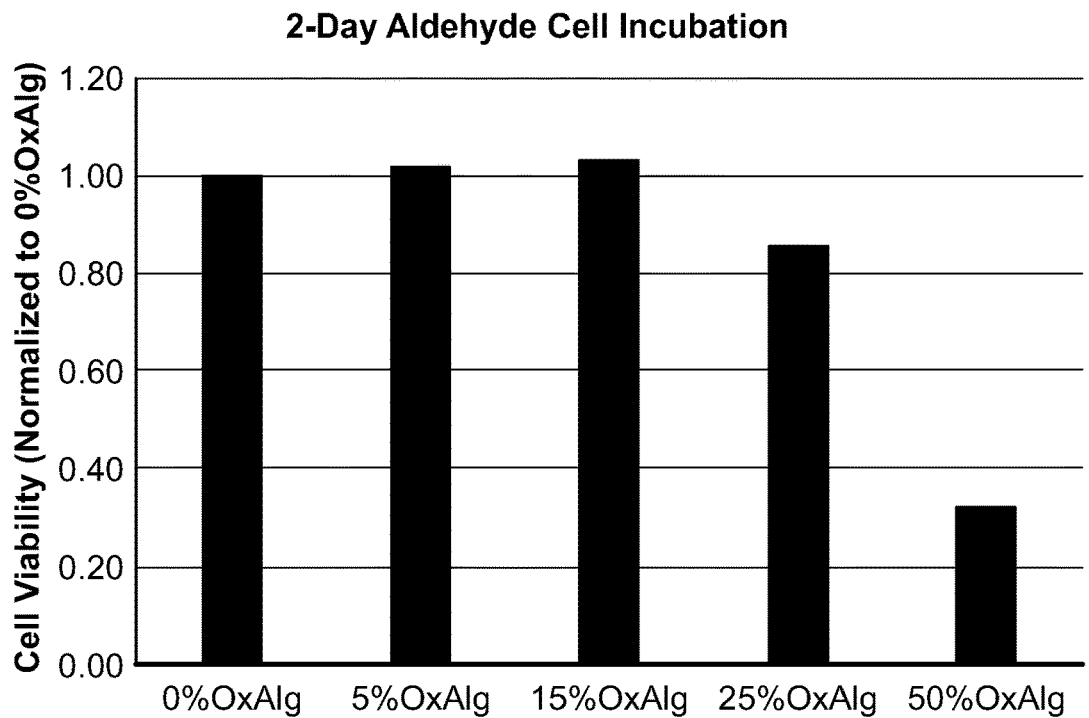
FIG. 9 is a bar graph showing relative cell viability in the presence of oxidized alginate containing 0-50% oxidation after 2-days of incubation.

The goal of this experiment was to determine the relative cell viability in the presence of aldehydes present in oxidized alginates. To this end, alginate was oxidized with sodium periodate to generate aldehyde containing alginate materials with 0-50% oxidation. Subsequently, 10 mg of this material was directly incubated for 2 days with $5 \times 10^5$ mouse leukemia cells (ATCC CCL-219, n=1) in DMEM with 10% horse serum. The viable cell number was quantified using MUSE Cell Count and Viability Assay Kit. The data, normalized to 0% oxidation, is shown in the table below and also graphically in FIG. 9.

| Sample (% oxidation) | 2-day viable cell count | Relative cell viability |
| --- | --- | --- |
| 0% ox | $7.91 \times 10^5$ | 1.00 |
| 5% ox | $8.06 \times 10^5$ | 1.02 |
| 15% ox | $8.16 \times 10^5$ | 1.03 |
| 25% ox | $6.78 \times 10^5$ | 0.86 |
| 50% ox | $2.58 \times 10^5$ | 0.33 |

The data indicates that cell viability is not affected by aldehydes up to 15% oxidation, and starts to decline rapidly at 25% and 50% oxidation.

Example 10. Solubility of Oxidized Alginates

Figure 10:
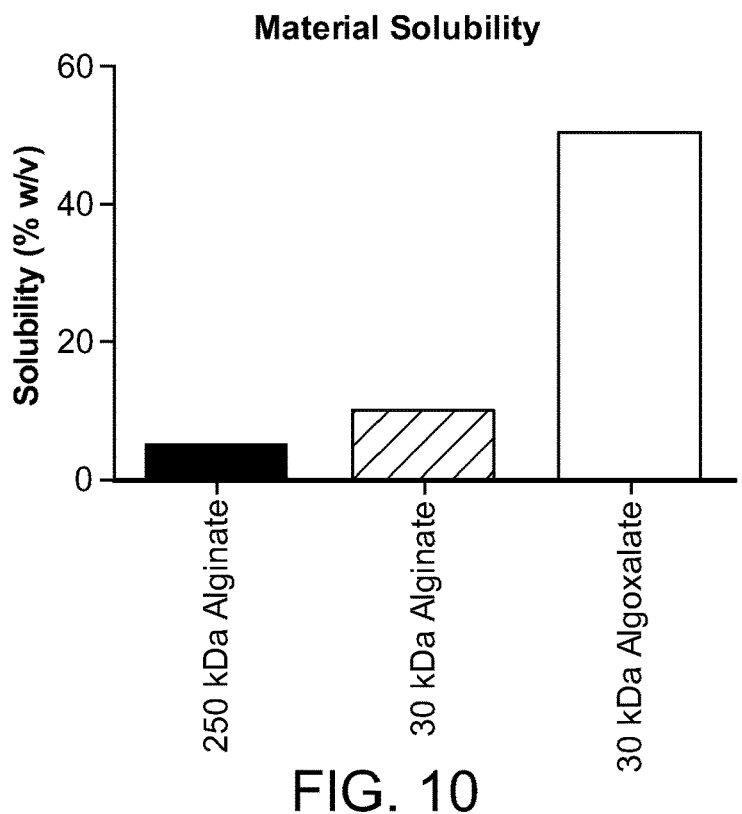
FIG. 10 is a bar graph showing the upper limits of solubility (% w/v) for unoxidized alginate with molecular weight of 250 kDa (MVG, left bar); unoxidized alginate with molecular weight of 30 kDa (VLVG, center bar); and for VLVG material that was oxidized to 20%, and then further oxidized by using sodium chlorite and conjugated with clicks (Tz or Nb, right bar).

The purpose of this experiment was to compare the solubility of oxidized alginate with click conjugation to the solubility of non-oxidized alginate. FIG. 10 is a bar graph showing solubility (% w/v) for unoxidized alginate with molecular weight of 250 kDa (MVG); unoxidized alginate with molecular weight of 30 kDa (VLVG); and alginate (MVG) with molecular weight of 30 kDa (VLVG) that was oxidized to 20%, and then further oxidized by using sodium clorite and conjugated with clicks (Tz or Nb) to produce a final product with a molecular weight of about 30 kDa. The VLVG material used in this experiment is shown in vial 5 of FIG. 7c. The click-conjugated and sodium processed alginate material used in this experiment is shown in vials 3 and 4 of FIG. 7c.

The data presented in FIG. 10 indicate that unoxidized MVG is only soluble to ~5% w/v, unoxidized VLVG is soluble to ~10% w/v; and click-conjugated sodium chlorite processed alginate is soluble to ~50%. The data demonstrate that alginate containing algoxalate, and, to a slightly lesser extent, alginate containing algoxalol, is characterized by a significantly increased solubility as compared to unoxidized alginate.

Example 11. Influence of Solubility of Alginate on the Crosslinking Potential The purpose of this experiment was to determine the upper limit of Tz conjugation for unoxidized alginate with molecular weights of 250 kDa (MVG) and 30 kDa (VLVG). MVG material is more viscous and less soluble than the VLVG material due to its higher molecular weight. This experiment was conducted using the experimental procedure as described in Example 8.

Figure 11A:
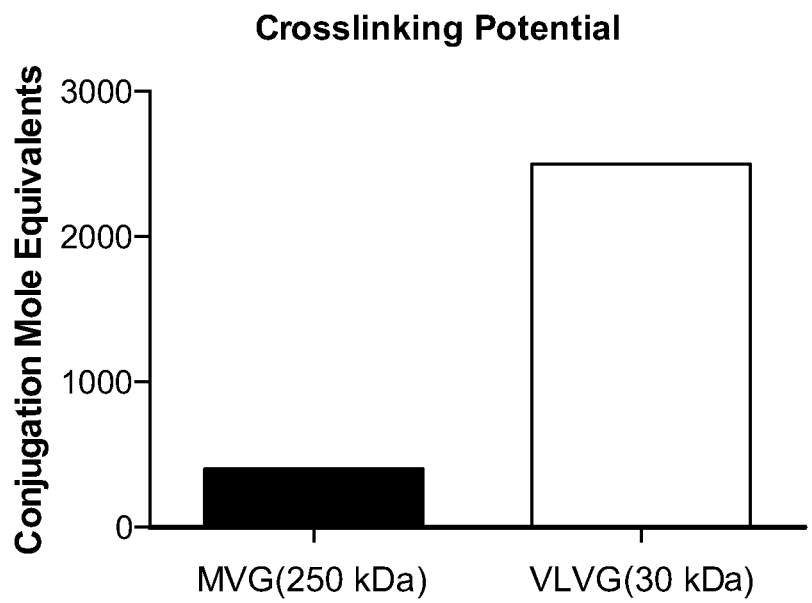
FIG. 11a is a bar graph showing the conjugation potential achieved for MVG and VLVG materials using Tz and Nb.

FIG. 11a is a bar graph showing the upper limit of Tz conjugation achieved for MVG and VLVG materials. The data in FIG. 11a demonstrates that less soluble MVG material may be conjugated to a maximum of ~500 molar equivalents of Tz, while the more soluble VLVG material may be conjugated to a maximum of ~2500 molar equivalents of Tz. Accordingly, increased solubility (due to lower molecular weight) of the VLVG material allows for greater degree of click substitution. This conjugation potential may be further extended through the use of alginate containing algoxanol and/or algoxalate due to its even lower viscosity.

Figure 11B:
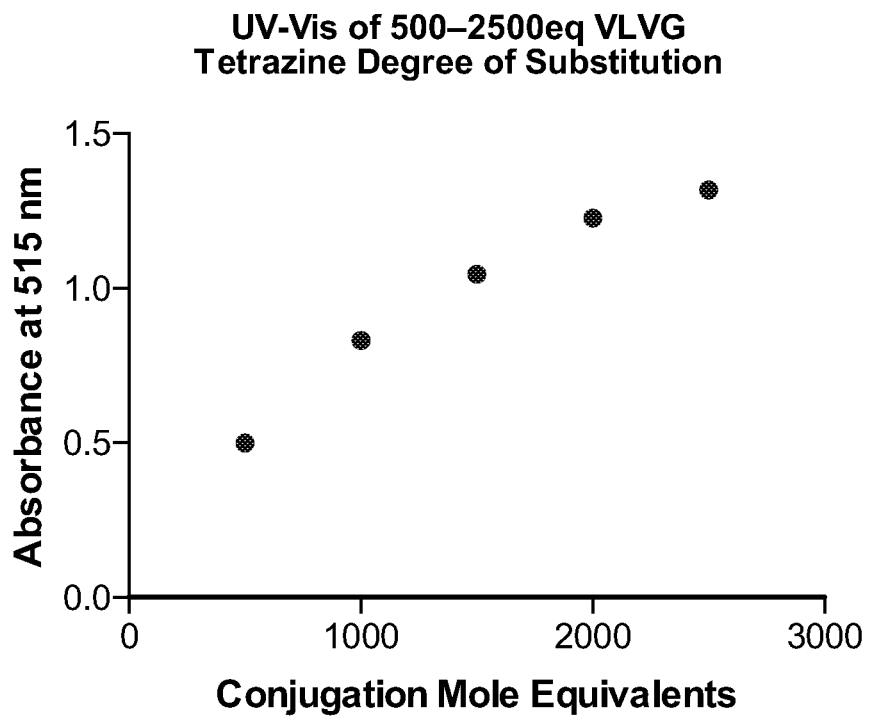
FIG. 11b is a graph showing the UV-Vis absorbance at 515 nm of the VLVG material as a function of molar equivalents of Tz.

FIG. 11b is a graph showing degree of substitution of the VLVG material as a function of molar equivalents of Tz. The material studied was VLVG reacted with 500, 1000, 1500, 2000 and 2500 molar equivalents of Tz. It demonstrates that the upper limit of Tz conjugation for VLVG material is achieved at ~2500 equivalents of Tz.

Example 12. Influence of Alginate Concentration and Degree of Click Substitution on the Kinetics of Gelation of Click-Conjugated Alginate Materials The purpose of this experiment was to study the kinetics of gelation of click conjugated alginate material as a function of alginate concentration, degree of oxidation and degree of click substitution using rheology measurements. This experiment utilized non-oxidized VLVG material conjugated with Nb and Tz using conjugation reactions that contained 500, 1500 and 2500 molar equivalents of Nb or Tz). This experiment also utilized MVG material that was oxidized to 10% or 20% oxidation using sodium periodate, reductively processed with ammonia borane and then conjugated with Nb and Tz using 250 molar equivalents of Nb and Tz in the conjugation reaction. Also used in this experiment was LF 20/40 alginate material which was oxidized to 20% oxidation using sodium periodate, reductively processed with ammonia borane and then conjugated to Nb or Tz using 1000 molar equivalents of Nb and Tz in the conjugation reaction.

Gelation of the click conjugated alginate material was determined by measuring the value of the elastic modulus G' using rheology measurements. To this end, Alg-N and Alg-T solutions at desired final concentrations (5%, 10%, 15% or 20% w/v in PBS) were mixed at a 1:1 ratio and directly pipetted onto the bottom plate of a TA Instruments ARG2 rheometer equipped with 20 mm flat upper plate geometry and a 400-micron geometry gap. A Peltier cooler was used to control the temperature for temperature dependent experiments, and a water reservoir cover was placed over the gel to prevent the hydrogel from drying during testing. Hydrogel samples were subjected to 1% strain at 1 Hz, and the storage and loss moduli (G' and G") were monitored for 1 hour.

Figure 12A:
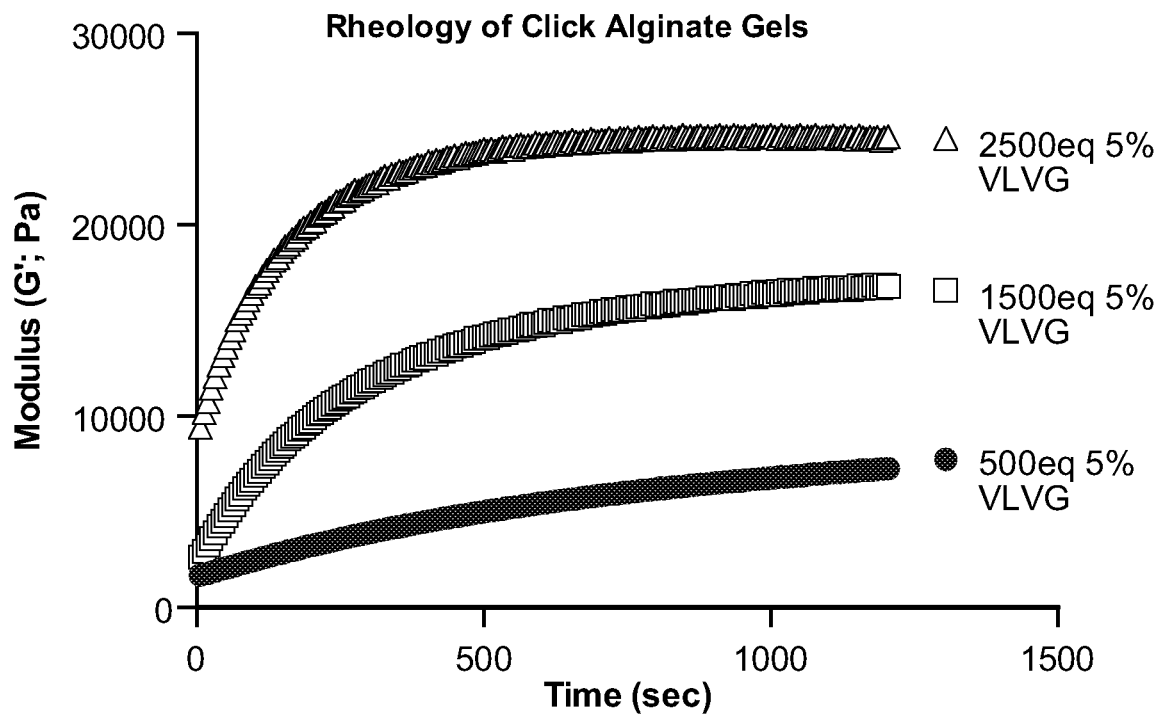
FIG. 12a is a graph showing the increase in the storage modulus (G') versus time for VLVG materials at different degrees of substitution and constant alginate concentration (% w/v).

FIG. 12a is a graph showing the increase in the elastic modulus G' versus time for different studied VLVG materials. This data effectively demonstrate how long it takes for different materials to gelate, with a plateau indicating that a gel-like state has been achieved. The data indicates that increasing degree of click substitution leads to more rapid gelation.

Figure 12B:
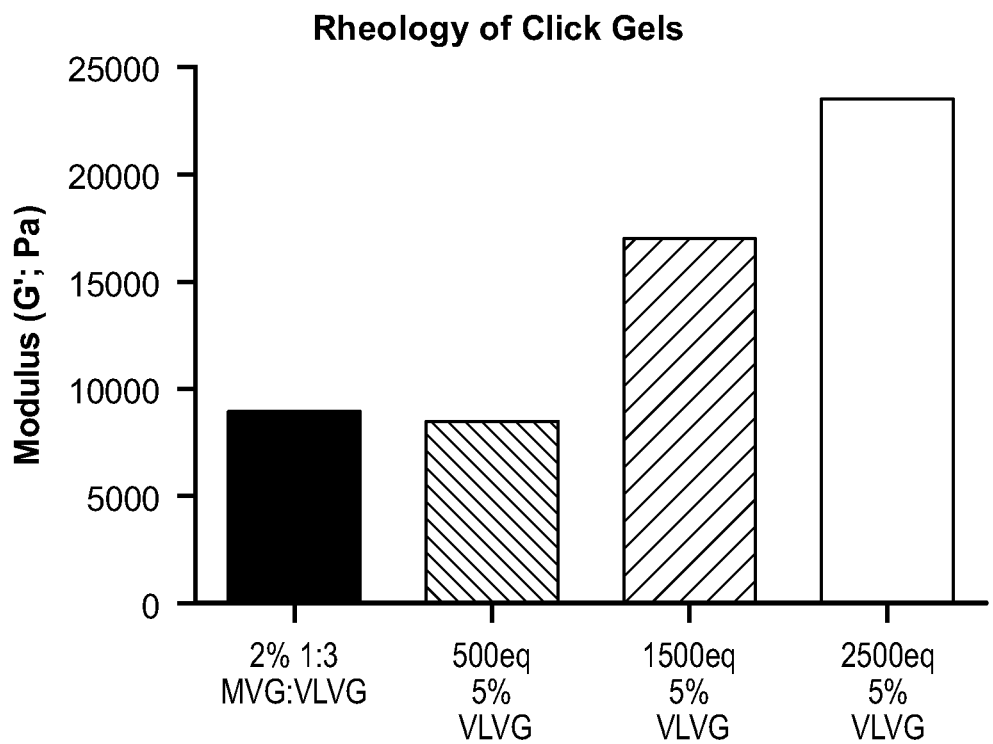
FIG. 12b is a bar graph showing the maximal value (from FIG. 13a) of the storage modulus (G') for VLVG materials at different degrees of substitution at the constant alginate concentration (% w/v).

FIG. 12b is a bar graph showing the value of the elastic modulus G' for different studied VLVG materials. The bar graph shown in black on the left and labeled "2% 1:3 MVG:VLVG" corresponds to control material, which is calcium crosslinked 2% w/v solution of 1:3 mixture of MVG:VLVG.

Figure 12C:
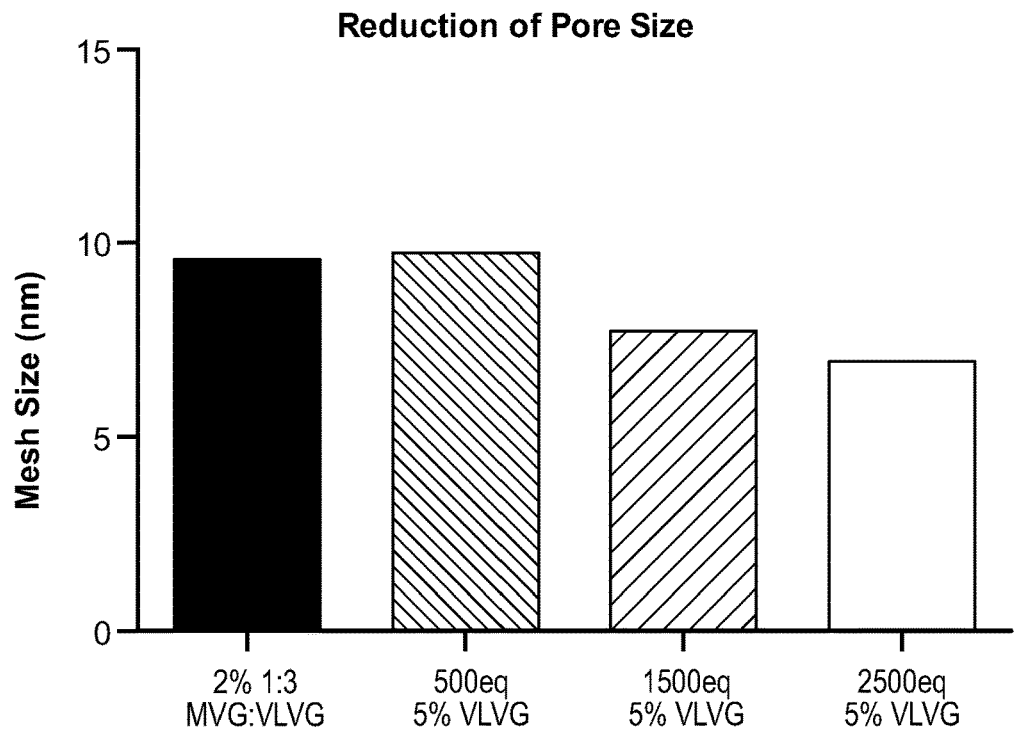
FIG. 12c is a bar graph showing the value of mesh size for VLVG materials at different degrees of substitution at the constant alginate concentration (% w/v), as derived from the maximal storage modulus (G') depicted in FIG. 13b.

FIG. 12c is a bar graph showing the value of mesh size for different studied VLVG materials. The bar graph shown in black on the left and labeled "2% 1:3 MVG:VLVG" corresponds to control material, which is a calcium crosslinked 2% w/v solution of 1:3 mixture of MVG:VLVG.

The data shown in FIGS. 12b and 12c indicate that increasing the degree of click substitution leads to different rheological properties of the material, as manifested in the increased elastic modulus G' and to a reduction in pore size.

Figure 12D:
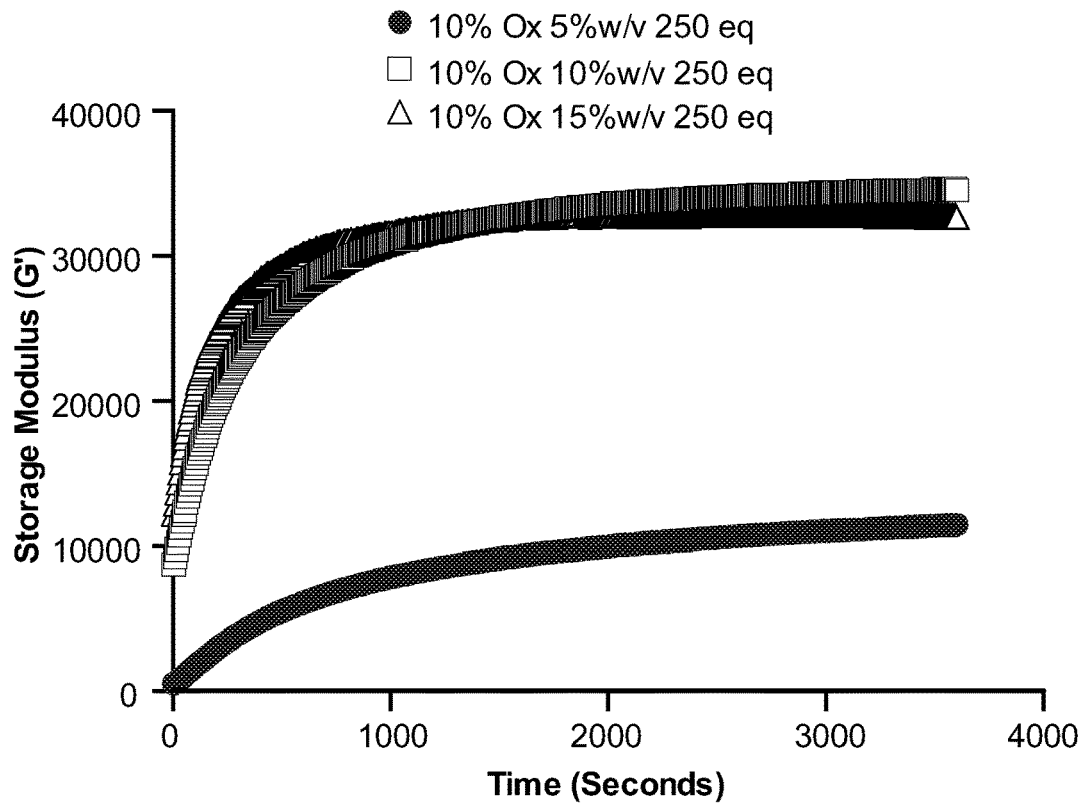
FIG. 12d is a graph showing the increase in the storage modulus (G') versus time for MVG material that was oxidized to 10% oxidation, reduced with ammonia borane and then conjugated with Nb or Tz using 250 molar equivalents of Nb and Tz at the concentration of reduced alginate of 5% w/v, 10% w/v or 15% w/v.
Figure 12E:
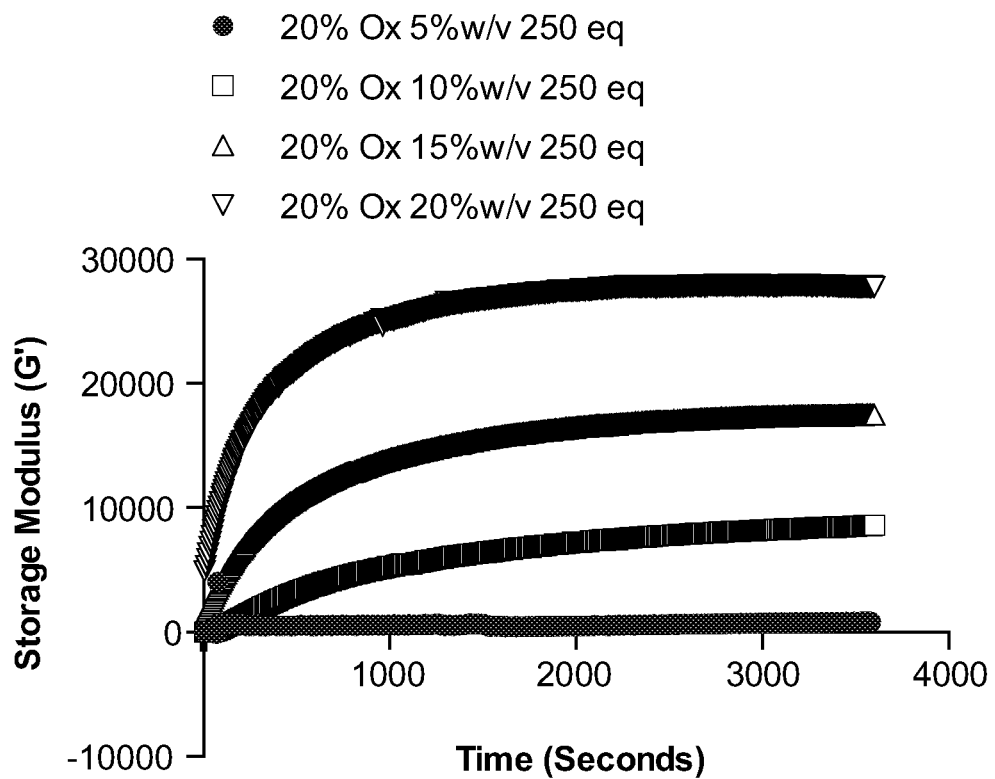
FIG. 12e is a graph showing the increase in the storage modulus (G') versus time for MVG material that was oxidized to 20% oxidation, reduced with ammonia borane and then conjugated with Nb or Tz using 250 molar equivalents of Nb and Tz at the concentration of reduced alginate of 5% w/v, 10% w/v, 15% w/v or 20% w/v.
Figure 12F:
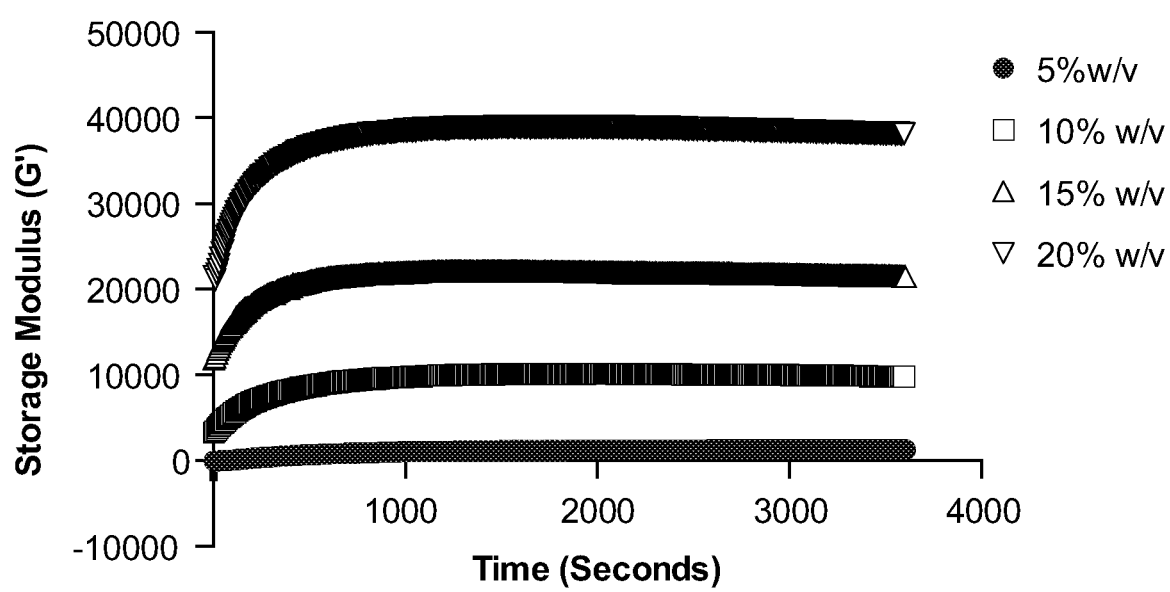
FIG. 12f is a graph showing the increase in the storage modulus (G') versus time for LF 20/40 material that was oxidized to 20% oxidation, reduced with ammonia borane and then conjugated with Nb or Tz using 1000 molar equivalents of Nb and Tz at the concentration of reduced alginate of 5% w/v, 10% w/v, 15% w/v or 20% w/v.

FIG. 12d is a graph showing the increase in the elastic modulus G' versus time for MVG material that was oxidized to 10% oxidation, reduced with ammonia borane and then conjugated with Nb or Tz using 250 molar equivalents of Nb and Tz. Hydrogels were produced at the concentration of click conjugated reduced alginate of 5% w/v, 10% w/v or 15% w/v. FIG. 12e is a graph showing the increase in the elastic modulus G' versus time for MVG material that was oxidized to 20% oxidation, reduced with ammonia borane and then conjugated with Nb or Tz using 250 molar equivalents of Nb and Tz. Hydrogels were produced at the concentration of click conjugated reduced alginate of 5% w/v, 10% w/v, 15% w/v or 20% w/v. FIG. 12f is a graph showing the increase in the elastic modulus G' versus time for LF 20/40 material that was oxidized to 20% oxidation, reduced with ammonia borane and then conjugated with Nb or Tz using 1000 molar equivalents of Nb and Tz. Hydrogels were produced at the concentration of click conjugated reduced alginate of 5% w/v, 10% w/v, 15% w/v or 20% w/v.

The data in FIG. 12d, FIG. 12e and FIG. 12f indicate that increasing the concentration of the reduced alginate reduces the time of gelation of the click conjugated alginates. The results demonstrate that it is possible to modulate the gelation process of click conjugated alginates by varying the degree of alginate oxidation, the relative amount of click reagents and the concentration of alginate in the click conjugation reaction.

Example 13. Influence of the Degree of Click Substitution on the Protein Release Rate The purpose of this experiment was to investigate the influence of the degree of click substitution on the release rates of various proteins encapsulated in click alginate hydrogels. This experiment utilized non-oxidized VLVG and MVG material conjugated with Nb or Tz produced as described in Example 11. Specifically, non-oxidized VLVG material was conjugated with Nb or Tz at 250, 500, 1000, 1500, 2000 and 2500 molar equivalents of Nb or Tz to produce Nb and Tz conjugated alginate (Alg-N and Alg-T). Non-oxidized MVG material was conjugated with Nb or Tz at 250 molar equivalents of Nb or Tz. This experiment also utilized proteins with different molecular weights, such as insulin (MW of ~3.5 kDa), bovine serum albumin (BSA, MW ~67 kDa) and IgG (MW ~150 kDa).

Protein release curves were evaluated by encapsulating insulin labeled with fluorescein (Sigma-Aldrich), bovine serum albumin (BSA; Sigma-Aldrich), and human Immunoglobulin G (IgG; Sigma-Aldrich) in click conjugated alginate. Samples were prepared by first separately dissolving freeze-dried Alg-N and Alg-T polymers of various degrees of substitution to final desired concentration (4% and 5% w/v) in PBS. The protein of interest was added and mixed with the Alg-N solution at the ratio of protein:alginate of 1:10 (Alg-N+Alg-T, v/v). This solution was then thoroughly mixed with the Alg-T solution, and the mixture was allowed to gel for at least 30 minutes. Samples were created by adding 1 mL of PBS to each gel and incubating at 37° C. Samples were collected at various timepoints with replacement of the supernatant at each timepoint. Protein content in the supernatant was quantified against a standard curve using a plate reader with fluorescence excitation at 492 nm and emission at 518 nm.

Figure 13A:
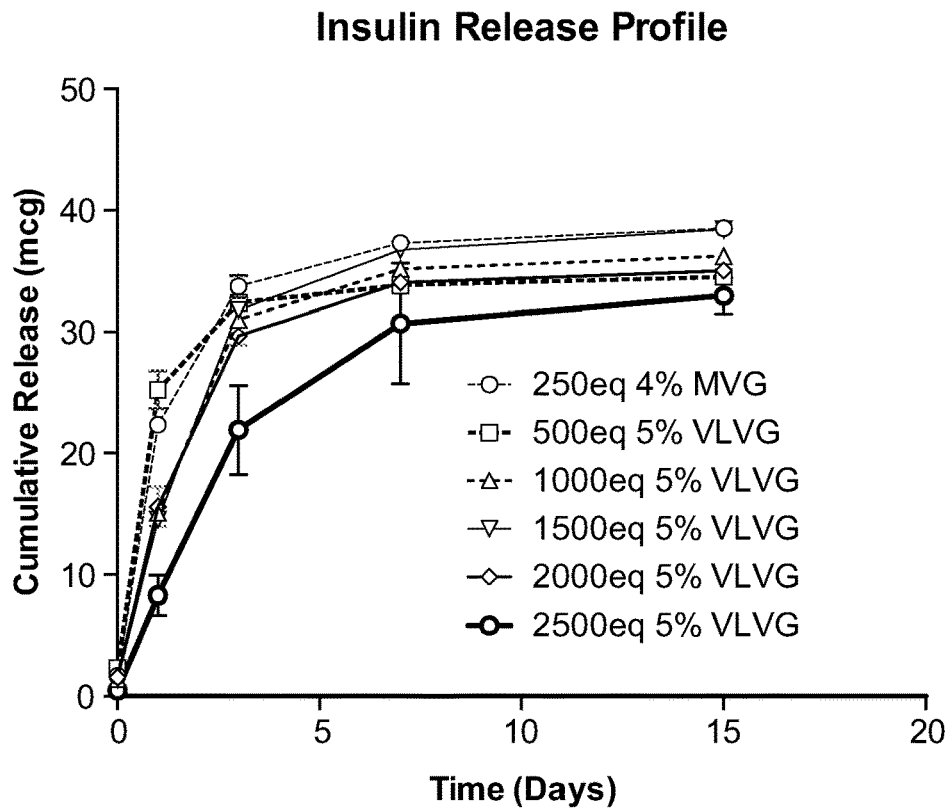
FIG. 13a is a graph showing cumulative release (in micrograms) of fluorescein conjugated insulin from hydrogels produced using click-conjugated VLVG materials with different degrees of click conjugation and constant alginate concentration (% w/v).
Figure 13B:
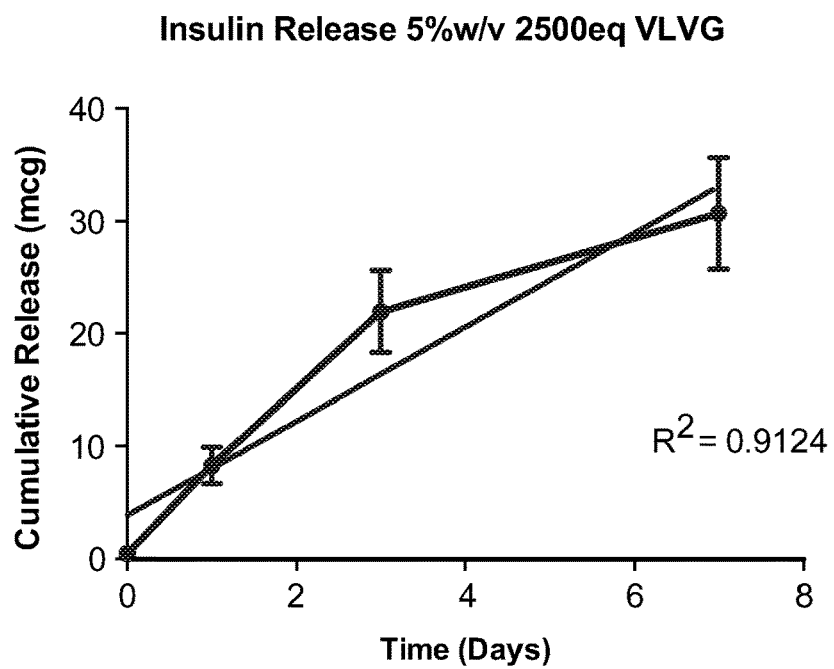
FIG. 13b is a graph showing the non-plateau region of the curve in FIG. 14a corresponding to 2500 molar equivalents of Nb or Tz and 5% concentration of the Alg-N and Alg-T during hydrogel formation (2500 eq 5% VLVG) and the linear fit.
Figure 13C:
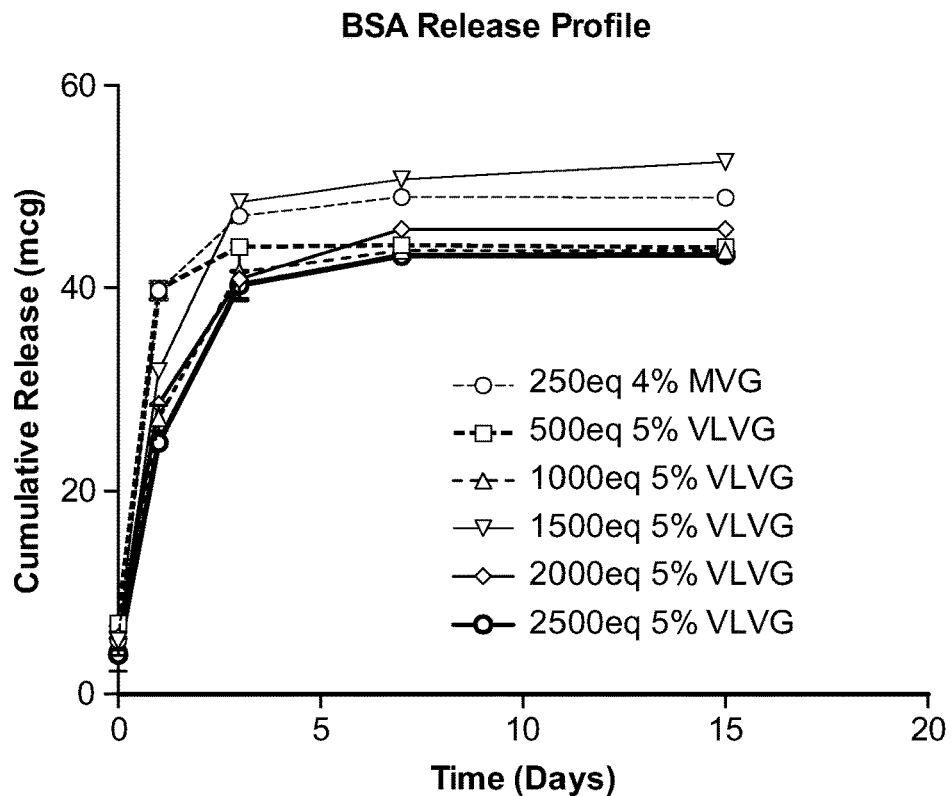
FIG. 13c is a graph showing cumulative release (in micrograms) of fluorescein conjugated BSA from hydrogels produced using click-conjugated VLVG materials with different degrees of click conjugation and constant alginate concentration (% w/v).
Figure 13D:
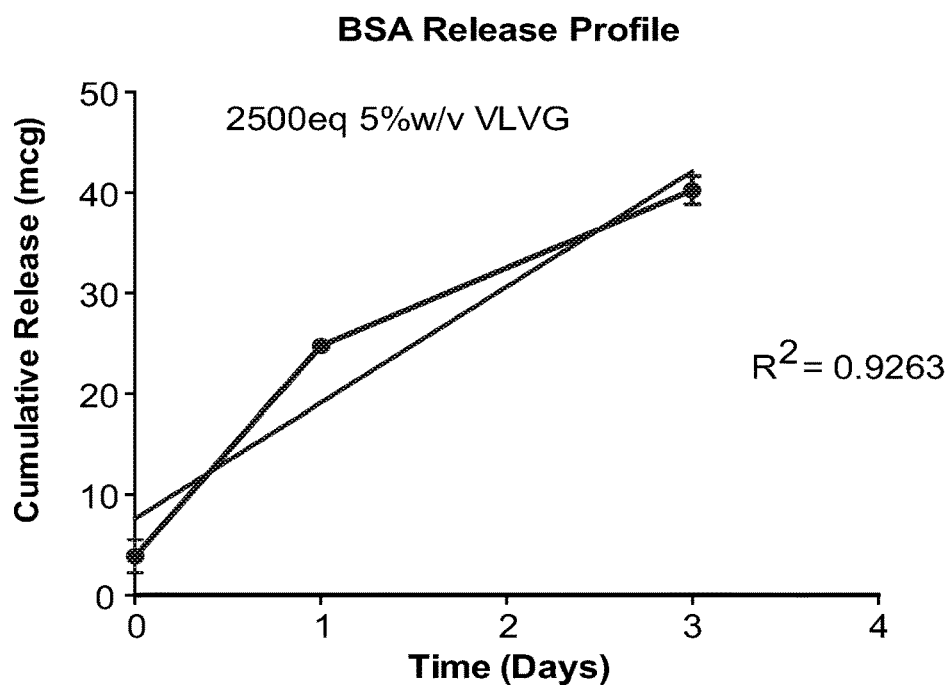
FIG. 13d is a graph showing the non-plateau region of the curve in FIG. 14c corresponding to 2500 molar equivalents of Nb or Tz and 5% concentration of the Alg-N and Alg-T during hydrogel formation (2500 eq 5% VLVG) and the linear fit.
Figure 13E:
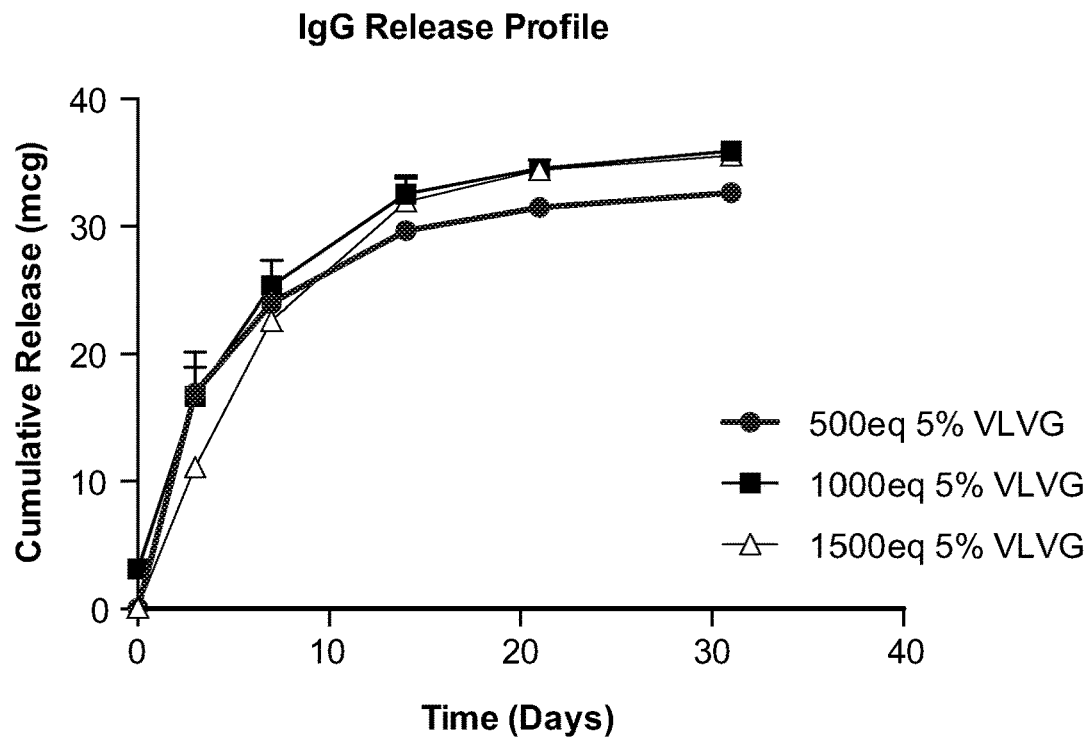
FIG. 13e is a graph showing cumulative release (in micrograms) of fluorescein conjugated IgG from hydrogels produced using click-conjugated VLVG materials with different degrees of click conjugation and constant alginate concentration (% w/v).
Figure 13F:
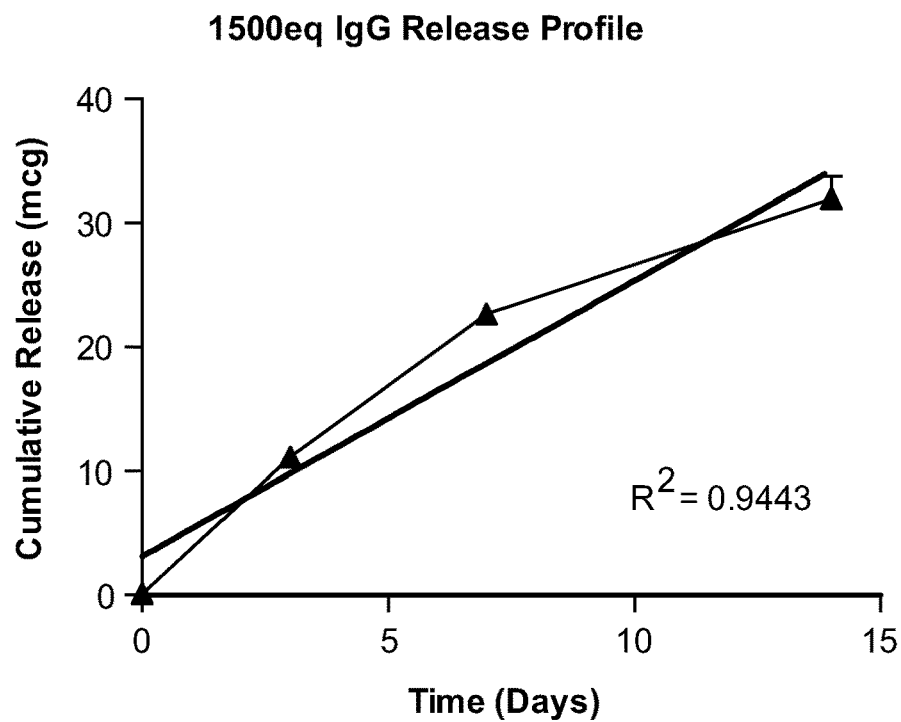
FIG. 13f is a graph showing the non-plateau region of the curve in FIG. 14e corresponding to 2500 molar equivalents of Nb or Tz and 5% concentration of the Alg-N and Alg-T during hydrogel formation (2500 eq 5% VLVG) and the linear fit.
Figure 13G:
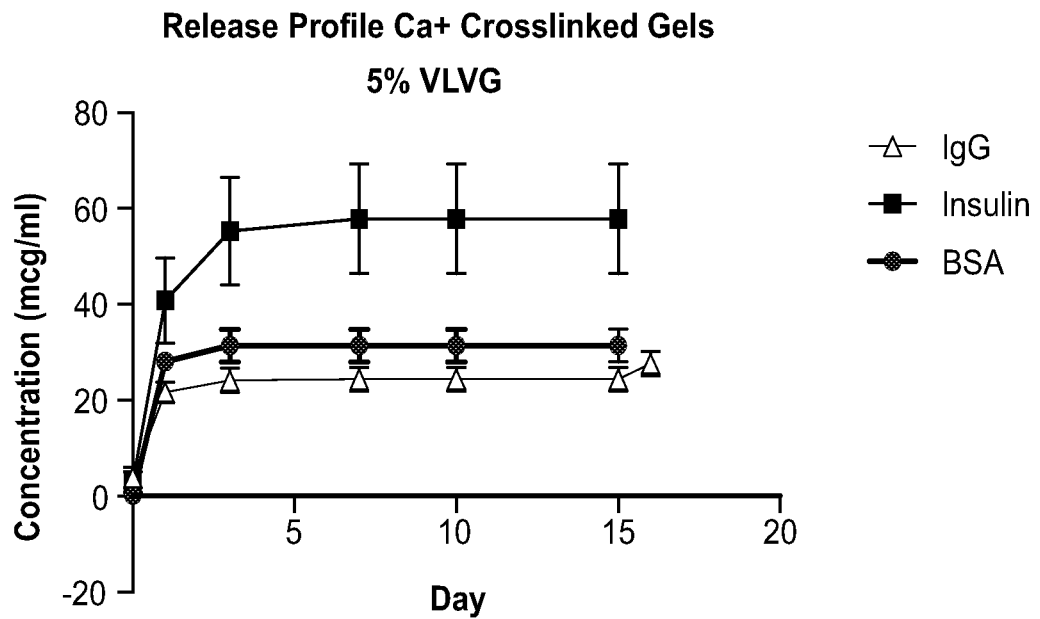
FIG. 13g is a graph showing cumulative release (in micrograms) of fluorescein conjugated insulin, BSA and IgG from hydrogels produced by $Ca^{2+}$ medicated crosslinking, showing significant, if not complete, burst release over the first 1-3 days.

FIG. 13a is a graph showing cumulative release (in micrograms) of fluorescein conjugated insulin from hydrogels produced using click-conjugated VLVG materials with different degrees of click conjugation. FIG. 13b is a graph showing the non-plateau region of the curve in FIG. 13a corresponding to 2500 molar equivalents of Nb or Tz and 5% concentration of the Alg-N and Alg-T during hydrogel formation (2500 eq 5% VLVG) and the linear fit. FIG. 13c is a graph showing cumulative release (in micrograms) of fluorescein conjugated BSA from hydrogels produced using click-conjugated VLVG materials with different degrees of click conjugation. FIG. 13d is a graph showing the non-plateau region of the curve in FIG. 13c corresponding to 2500 molar equivalents of Nb or Tz and 5% concentration of the Alg-N and Alg-T during hydrogel formation (2500 eq 5% VLVG) and the linear fit. FIG. 13e is a graph showing cumulative release (in micrograms) of fluorescein conjugated IgG from hydrogels produced using click-conjugated VLVG materials with different degrees of click conjugation. FIG. 13f is a graph showing the non-plateau region of the curve in FIG. 13e corresponding to 2500 molar equivalents of Nb or Tz and 5% concentration of the Alg-N and Alg-T during hydrogel formation (2500 eq 5% VLVG) and the linear fit. FIG. 13g is a graph showing cumulative release (in micrograms) of fluorescein conjugated insulin, BSA and IgG from hydrogels produced by $Ca^{2+}$ mediated crosslinking.

The data shown in FIGS. 13a-13g demonstrate that protein release profile from alginate hydrogels may be influenced by the degree of click substitution of the alginate. Specifically, the data shows that a higher degree of click substitution reduces the "initial burst" of proteins from the hydrogel. Using alginates with a higher degree of click substitution allows for the production of hydrogels with smaller "mesh size", which, in turn, allows achieving longer protein release times. For example, as evidenced by FIGS. 13b, 13d and 13f, alginates having the highest degree of click substitution (2500 equivalents), produce hydrogels that afford linear protein release rates over several days. In contrast, hydrogels produced from other materials afford non-linear, "burst" protein release over hours, not days. Examples of other materials are described, for example, in KS Anseth, et. al., *Biomed. Mater. Res. A,* 2009, 90: 720-729; P P Kundu, et. al., *Carbohydrate Polymers,* 2014, 112: 627-637; T. Bal, et. al., *J. Biomed. Mater. Res. Part A,* 2014. 102A: 487-495; C. E. Schmidt, et. al. *Biomaterials,* 2005, 26: 125-135; Y. M. Lee, et. al., *Macromol. Research,* 2006. 14: 87-93; C. P. Covas, et. al., *Mat. Sci. App.* 2011. 2: 509-520; W. F. Mieler, et. al., *Trans. Am. Ophtalmol. Soc.,* 2008. 106: 206-214; W. M. Tian, et. al., *Controlled Release,* 2005. 102: 13-22.

Example 14. Influence of the Degree of Alginate Oxidation and Alginate Concentration on the Protein Release Rate The purpose of this experiment was to investigate the influence of the degree of alginate oxidation and alginate concentration during the gelation process on the release rates of various proteins encapsulated in click alginate hydrogels. This experiment utilized LF 20/40 alginate material that was initially oxidized by sodium periodate to 5% or 10% oxidation as described in Example 1. Subsequently, the oxidized LF 20/40 alginate was either reductively processed with ammonia borane (AB) or further oxidized with sodium chlorite (SC) using the procedure described in Example 2. This material was then conjugated with Nb or Tz using 2000 molar equivalents of Nb or Tz and the procedure described in Example 4. Subsequently, this material was used to produce hydrogels and to encapsulate insulin or IgG at 5% or 10% w/v alginate concentration. Protein release profiles were monitored as described in Example 13.

Figure 14A:
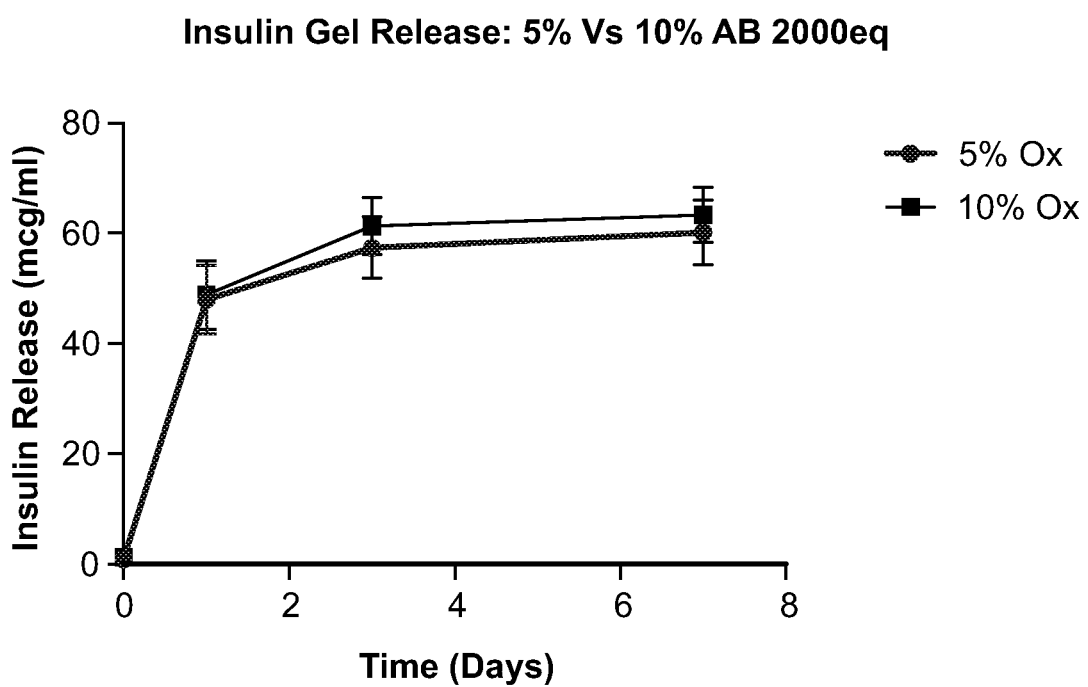
FIG. 14a is a graph showing cumulative release (in micrograms) of fluorescein conjugated insulin from hydrogels produced using click-conjugated LF 20/40 alginate at the concentration of 5% w/v that was oxidized to 5% or 10% and then reductively processed with AB.

FIG. 14a is a graph showing cumulative release (in micrograms) of fluorescein conjugated insulin from hydrogels produced using click-conjugated LF 20/40 alginate at the concentration of 5% w/v that was oxidized to 5% or 10% and then reductively processed with AB.

Figure 14B:
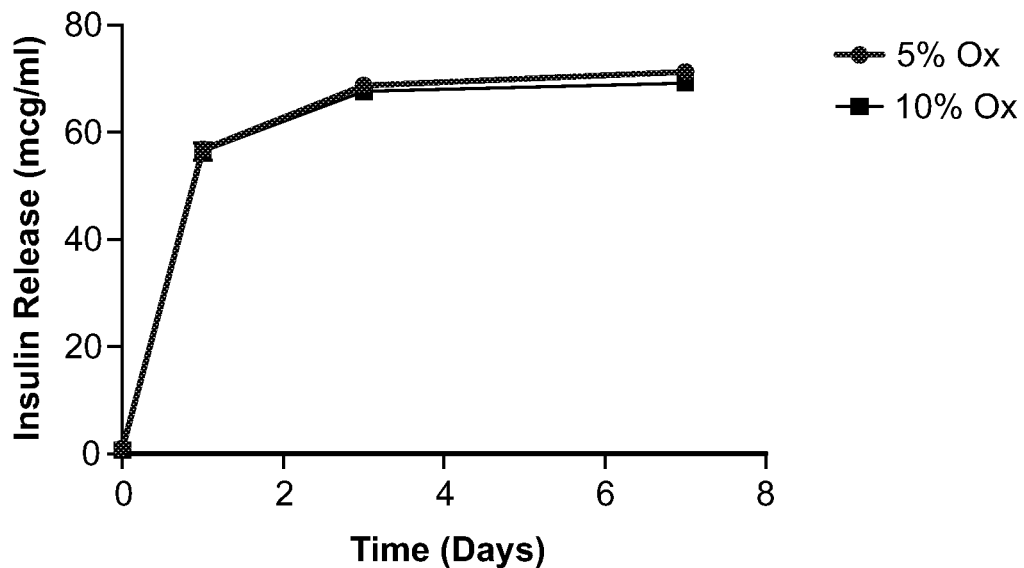
FIG. 14b is a graph showing cumulative release (in micrograms) of fluorescein conjugated insulin from hydrogels produced using click-conjugated LF 20/40 alginate at the concentration of 5% w/v that was oxidized to 5% or 10% and then oxidatively processed with SC.

FIG. 14b is a graph showing cumulative release (in micrograms) of fluorescein conjugated insulin from hydrogels produced using click-conjugated LF 20/40 alginate at the concentration of 5% w/v that was oxidized to 5% or 10% and then oxidatively processed with SC.

Figure 14C:
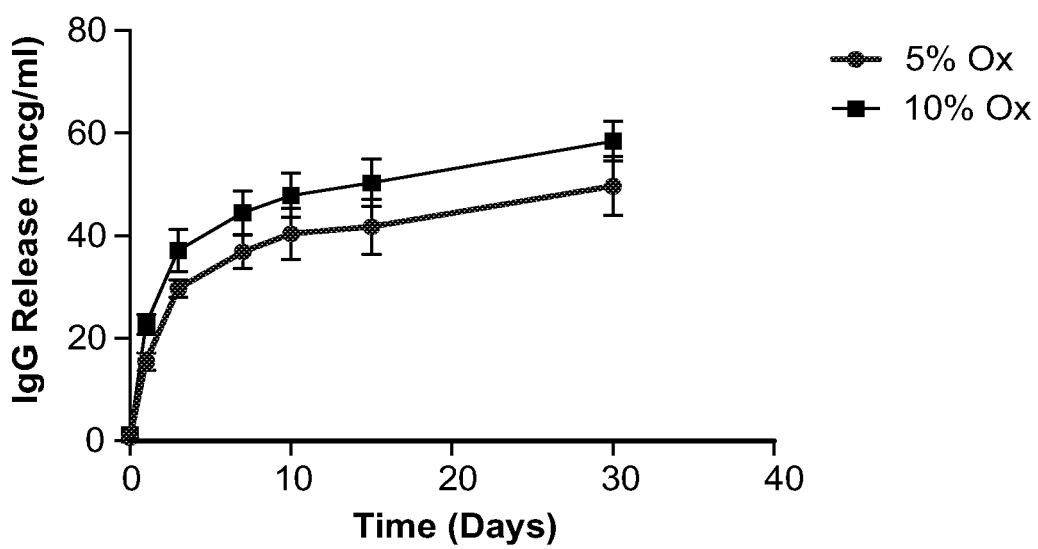
FIG. 14c is a graph showing cumulative release (in micrograms) of fluorescein conjugated IgG from hydrogels produced using click-conjugated LF 20/40 alginate at the concentration of 5% w/v that was oxidized to 5% or 10% and then reductively processed with AB.

FIG. 14c is a graph showing cumulative release (in micrograms) of fluorescein conjugated IgG from hydrogels produced using click-conjugated LF 20/40 alginate at the concentration of 5% w/v that was oxidized to 5% or 10% and then reductively processed with AB.

Figure 14D:
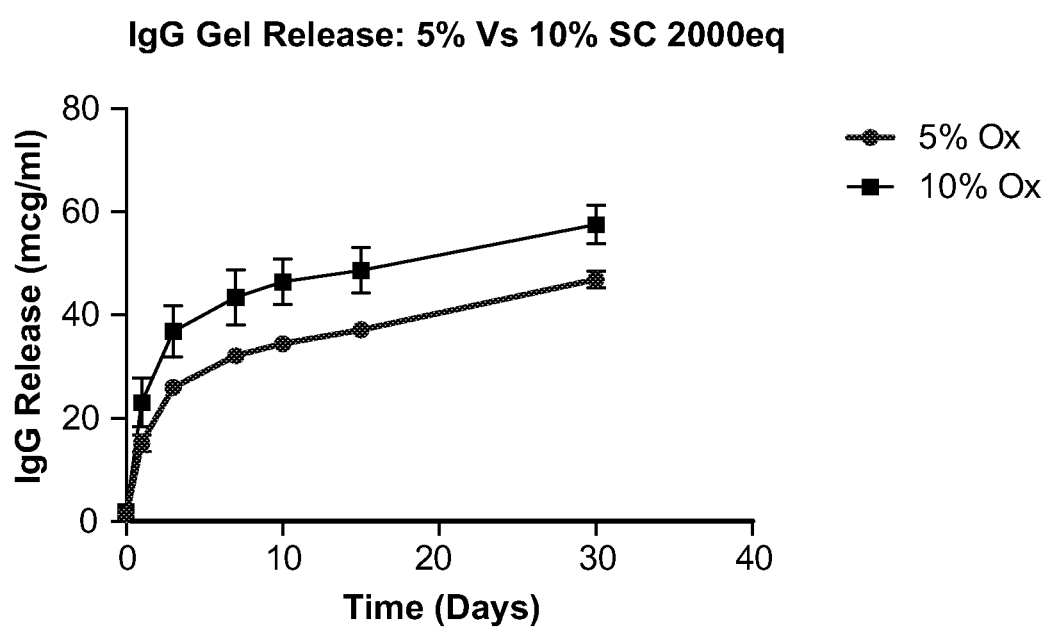
FIG. 14d is a graph showing cumulative release (in micrograms) of fluorescein conjugated IgG from hydrogels produced using click-conjugated LF 20/40 alginate at the concentration of 5% w/v that was oxidized to 5% or 10% and then oxidatively processed with SC.

FIG. 14d is a graph showing cumulative release (in micrograms) of fluorescein conjugated IgG from hydrogels produced using click-conjugated LF 20/40 alginate at the concentration of 5% w/v that was oxidized to 5% or 10% and then oxidatively processed with SC.

The data in FIGS. 14a-14d indicate that modulation of protein release profiles may be achieved by varying the degree of alginate oxidation for Ab and SC processed material and the concentration of alginate material during the gelation process.

Figure 15A:
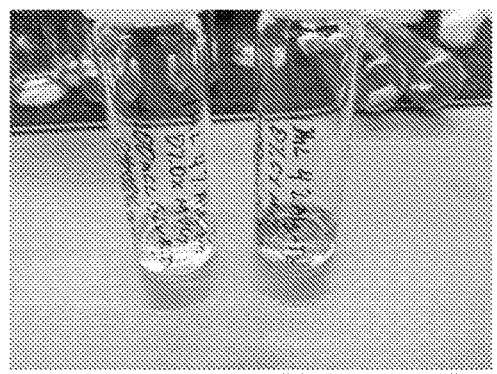
FIG. 15a is a series of pictures of glass vials containing 4% MVG material conjugated to Nb (left vial) and Tz (right vial) in the presence of 2.3% gluteraldehyde, taken after 0 minutes, 40 minutes, 21.5 hours and 67.5 hours, showing significant color change indicating modification of the click moieties.
Figure 15A:
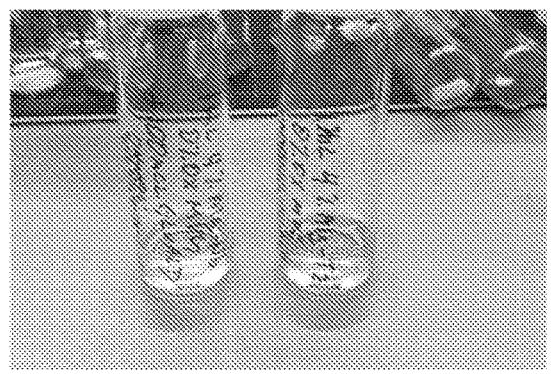
Figure 15A:
Figure 15A:
Figure 15B:
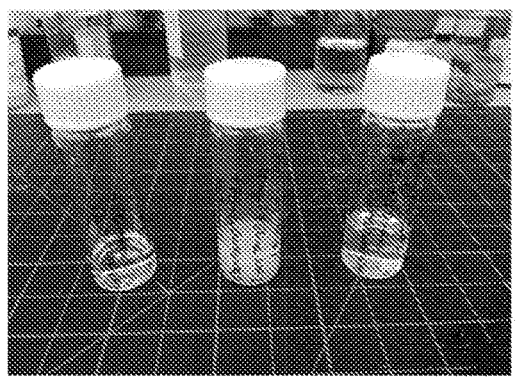
FIG. 15b is a series of pictures of glass vials containing water as control (left vial) or 2% MVG material conjugated to DBCO (middle vial) or azide (right vial), taken after 0 minutes, 40 minutes, 20 hours and 69 hours, showing significant color change indicating modification of the click moieties.
Figure 15B:
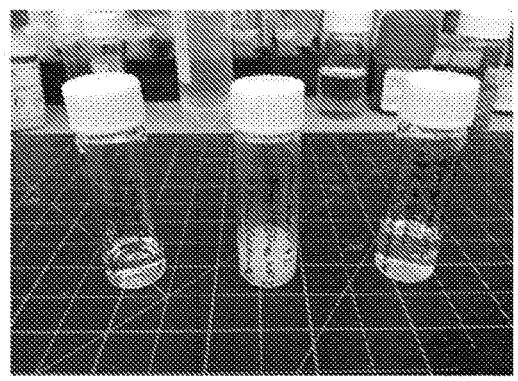
Figure 15B:
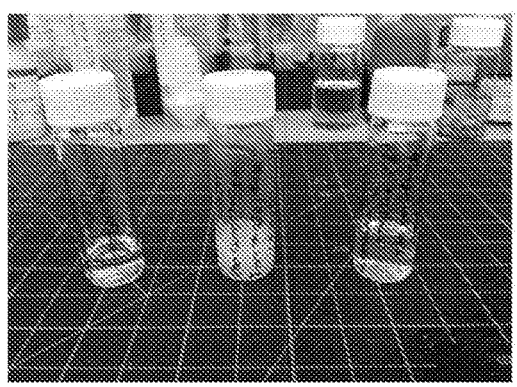
Figure 15B:
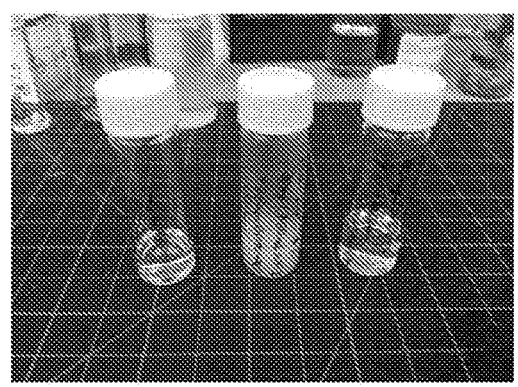

Example 15. Effect of Aldehydes Present in Oxidized Alginate on Click Moieties The goal of this experiment was to determine the stability of click moieties conjugated to alginate in the presence of aldehydes. To this end, non-oxidized MVG material was conjugated to Nb or Tz in a conjugation reaction that used 250 equivalents of the click material, and was subsequently exposed to 2.3% of gluteraldehyde. The vials were observed for up to 69 hours for color change. FIG. 15a is a series of pictures of glass vials containing 4% MVG material conjugated to Nb (left vial) and Tz (right vial) in the presence of 2.3% gluteraldehyde, taken after 0 minutes, 40 minutes, 21.5 hours and 67.5 hours. FIG. 15b is a series of pictures of glass vials containing water as control (left vial) or 2% MVG material conjugated to DBCO (middle vial) or azide (right vial), taken after 0 minutes, 40 minutes, 20 hours and 69 hours. The data in FIG. 15a indicate that degradation of Nb and Tz is observed after 40 minutes of exposure to aldehydes. Degradation of DBCO and azide takes longer, but may be observed after 20 hours, as evidenced by the data in FIG. 15b. Because aldehydes are generated upon oxidation of alginate, this experiment demonstrates that click moieties conjugated to alginate will be expected to degrade upon oxidation of alginate. Therefore, to maintain click moiety stability, the aldehydes must be either reductively eliminated, e.g., using reduction with ammonia borane, or oxidatively eliminated, e.g., using further oxidation with sodium chlorite.

Example 16. Encapsulation and Retention of Liposomes by Alginate Hydrogels

The purpose of this experiment was to investigate the ability of hydrogels produced from click conjugated alginates to encapsulate liposomes and to provide sustained and localized delivery of intact liposomes in vivo. This experiment utilized commercially available liposomes prepared from 1,2-dioleoyl-sn-glycero-3-phosphocholine (DOPC) and cholesterol (CHOL), at the ratio of DOPC/CHOL of 55:45 and total lipid concentration of 50 mM. The liposomes also contained the fluorescent dye 1,1'-Dioctadecyl-3,3,3',3'-Tetramethylindocarbocyanine Perchlorate (DiI) at the concentration of 0.5 mM (0.47 mg/mL) and had an average diameter of 133 nm. The liposomes were encapsulated in hydrogels prepared from non-oxidized MVG material by crosslinking in the presence of $CaSO_4$ and liposomes at the alginate concentration of 2% or 5% w/v. The liposomes were also encapsulated in hydrogels prepared from non-oxidized MVG material that was conjugated to Nb or Tz using 250 molar equivalents of Nb or Tz and allowed to gel in the presence of liposomes at the alginate concentration of 5% w/v. Finally, the liposomes were also encapsulated in hydrogels prepared from click conjugated gelatin prepared as described in, e.g., Koshy et al., *Advanced Healthcare Materials* 2016, Vol. 5, Issue 5, pages 541-547. Liposome release from the hydrogels was monitored in vitro by measuring the increase in DiI fluorescence in the supernatant. Supernatant protein content was quantified against a standard curve using a platereader with fluorescence excitation at 550 nm and emission at 580 nm.

Figure 16A:
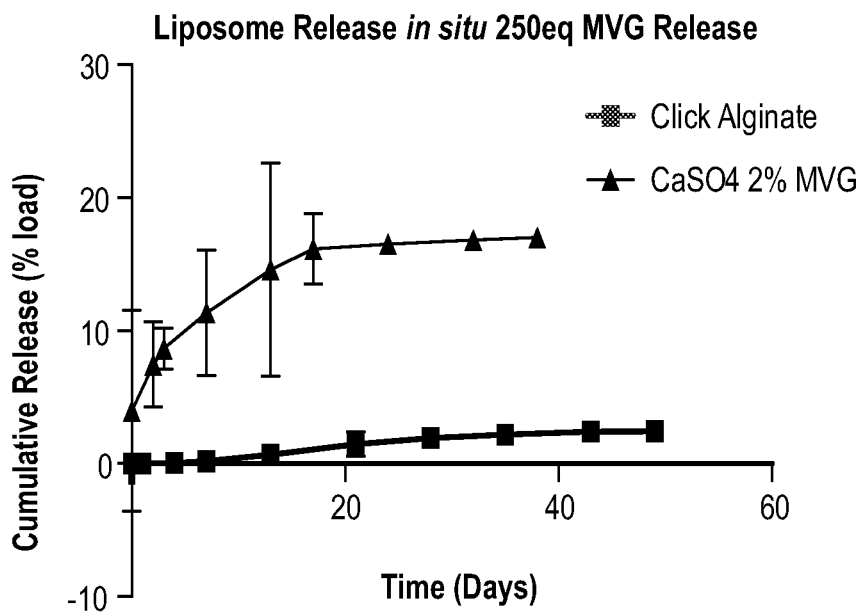
FIG. 16a is a graph showing cumulative release (% load) of neutral liposomes (DOPC:Cholesterol) from $Ca^{2+}$ cross-linked alginate and from non-oxidized click conjugated alginate over the period of 50 days in $PBS^{++}$ (a PBS buffer that contains $Ca^{2+}$ and $Mg^{2+}$ ions).
Figure 16B:
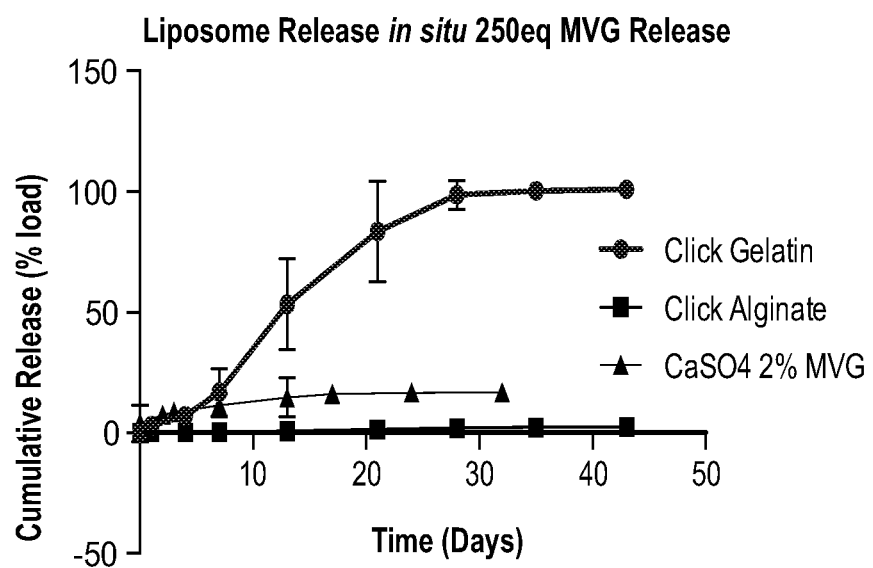
FIG. 16b is a graph showing cumulative release (% load) of neutral liposomes (DOPC:Cholesterol) from $Ca^{2+}$ cross-linked alginate hydrogel, non-oxidized click conjugated alginate hydrogel and click gelatin hydrogel in $PBS^{++}$ (a PBS buffer that contains $Ca^{2+}$ and $Mg^{2+}$ ions).

FIG. 16a is a graph showing cumulative release (% load) of liposomes from $Ca^{2+}$ cross-linked alginate and from non-oxidized click conjugated alginate over the period of 50 days. FIG. 16b is a graph showing cumulative release (% load) of liposomes from $Ca^{2+}$ cross-linked alginate hydrogel, non-oxidized click conjugated alginate hydrogel and click gelatin hydrogel. These results indicate that quantitative release of liposomes from click gelatin hydrogel is observed after 30 days. In contrast, alginate hydrogels were more effective in retaining liposomes. Specifically, non-oxidized click conjugated alginate hydrogel retained at least about 95% of the liposome load after 50 days, while $Ca^{2+}$ cross-linked alginate hydrogel retained about 85% of the liposome load after 40 days. This data demonstrates that, of the studied hydrogels, non-oxidized click conjugated alginate hydrogel is most effective at retaining liposomes over the period of 40 or more days.

Figure 16C:
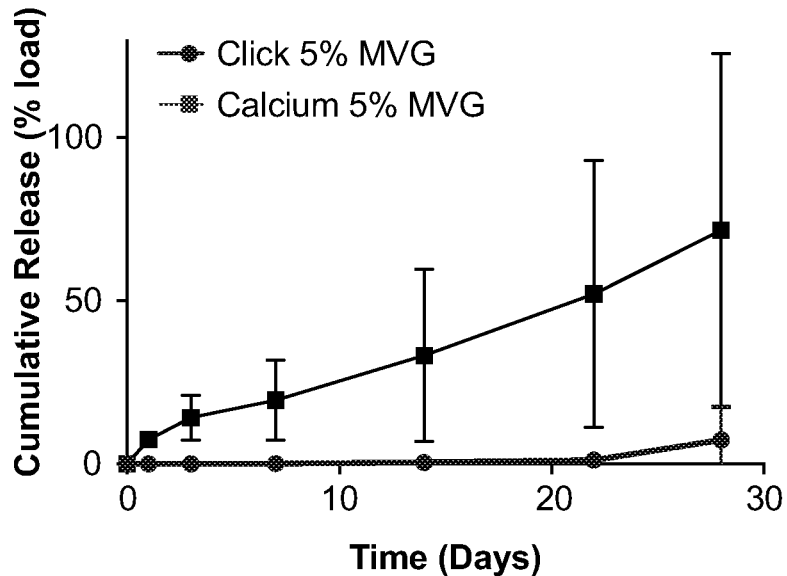
FIG. 16c is a graph showing cumulative release (% load) of neutral liposomes (DOPC:Cholesterol) over the period of 28 days from $Ca^{2+}$ cross-linked alginate and from non-oxidized click conjugated alginate hydrogels prepared at 5% w/v alginate concentration. The liposome release profiles were measured in vitro in $PBS^{--}$, which is a PBS buffer that does not contain $Ca^{2+}$ or $Mg^{2+}$ ions, and demonstrate that click-crosslinked gels are able to retain the encapsulated liposomes (diffusion limited), while liposomes are able to diffuse out of the calcium crosslinked gels.

FIG. 16c is a graph showing cumulative release (% load) of liposomes over the period of 28 days from $Ca^{2+}$ cross-linked alginate and from non-oxidized click conjugated alginate hydrogels prepared at 5% w/v alginate concentration. The liposome release profiles were measured in vitro in $PBS^{--}$, which is a PBS buffer that does not contain $Ca^{2+}$ or $Mg^{2+}$ ions.

The data in FIG. 16c indicates that about 60% of the liposome load is released from $Ca^{2+}$ cross-linked alginate hydrogels after 28 days. Calcium cross-linking of alginate in the presence of liposomes leads to significant heterogeneity and sheer stress on encapsulated liposomes, resulting in liposome release. In contrast, non-oxidized click conjugated alginate hydrogel is capable of retaining its liposome load for at least 20 days.

Figure 16D:
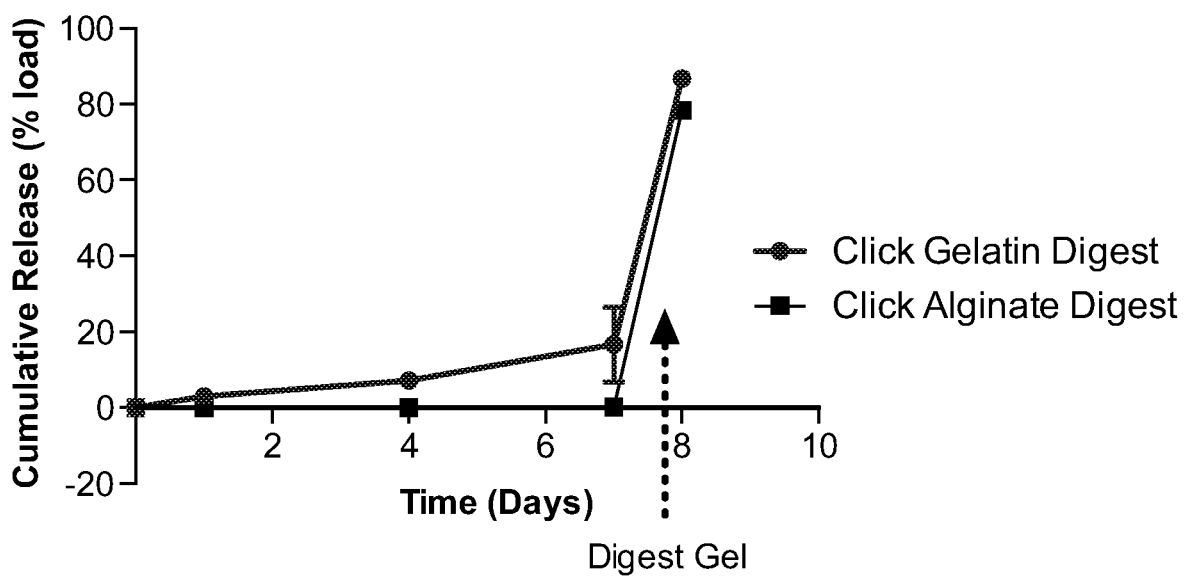
FIG. 16d is a graph showing cumulative release (% load) of neutral liposomes (DOPC:Cholesterol) from non-oxidized click conjugated alginate hydrogels and click conjugated gelatin hydrogels over the period of 8 days. Gels were digested with alginate lyase or collagenase, respectively, on the $8^{th}$ day in order to show recovery and mass balance.

FIG. 16d is a graph showing cumulative release (% load) of liposomes from non-oxidized click conjugated alginate hydrogels and click conjugated gelatin hydrogels over the period of 8 days. Addition of alginate lyase capable of digesting alginate results in quick release of liposomes from the non-oxidized click conjugated alginate hydrogels. Addition of collagenase capable of digesting gelatin results in quick release of liposomes from click conjugated gelatin hydrogels. Click conjugated gelatin hydrogels are expected to be degraded in vivo because collagenases are ubiquitous in vivo, e.g., in a human body. In contrast, alginate lyases are not ubiquitous in vivo, therefore, alginate hydrogels are expected to remain intact in vivo if un-oxidized. With oxidation, alginate degradation is pH dependent.

Example 17. Intactness of Liposomes after Encapsulation

The purpose of this experiment was to assess the ability of liposomes remain intact, e.g., maintain their diameter after encapsulation and be recovered from different hydrogels. The hydrogels studied in this experiment include calcium cross-linked alginate hydrogel, non-oxidized click conjugated alginate hydrogel and click conjugated gelatin hydrogel as described in Example 16. The size of the liposomes was measured by dynamic light scattering (DLS).

Figure 17A:
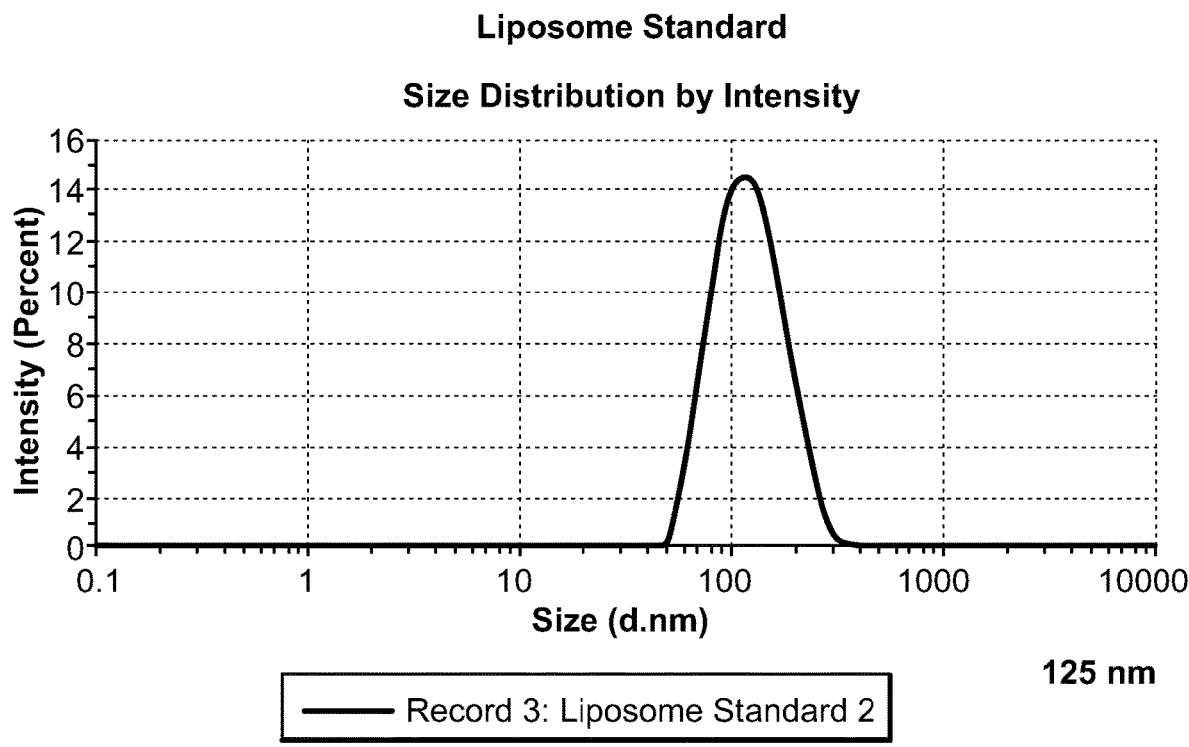
FIG. 17a is a dynamic light scattering (DLS) trace of the liposome stock material that was encapsulated in the gels depicted in FIG. 17d.

FIG. 17a is a dynamic light scattering (DLS) trace of a liposome standard.

Figure 17B:
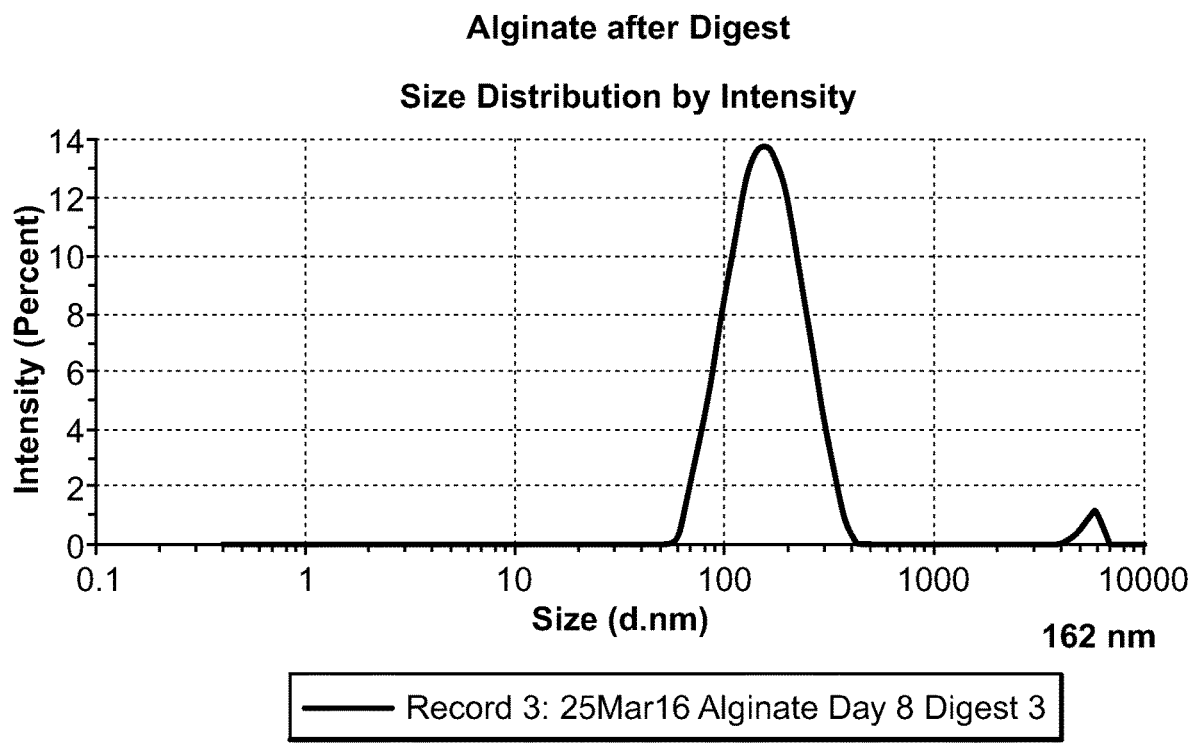
FIG. 17b is a DLS trace of a liposome which has been released from a non-oxidized click conjugated alginate hydrogel digested with alginate lyase after 8 days as depicted in FIG. 17d, showing minimal difference from the average diameter of the liposomes present in the stock solution.

FIG. 17b is a DLS trace of a liposome which has been released from a non-oxidized click conjugated alginate hydrogel digested with alginate lyase after 8 days.

Figure 17C:
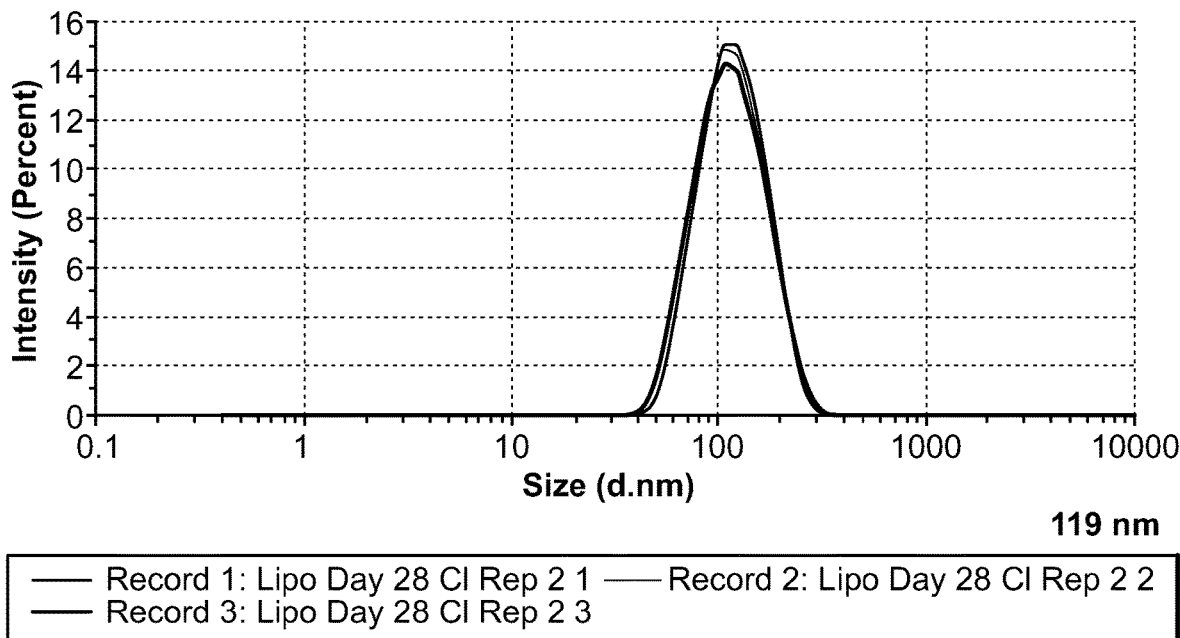
FIG. 17c is a DLS trace of a liposome which has been released after 28 days from a non-oxidized click conjugated alginate hydrogel prepared at the concentration of alginate of 5% w/v in $PBS^-$ buffer, showing minimal difference from the average diameter of the liposomes present in the stock solution.

FIG. 17c is a DLS trace of a liposome which has been released after 28 days from a non-oxidized click conjugated alginate hydrogel prepared at the concentration of alginate of 5% w/v in $PBS^{--}$ buffer.

Figure 17D:
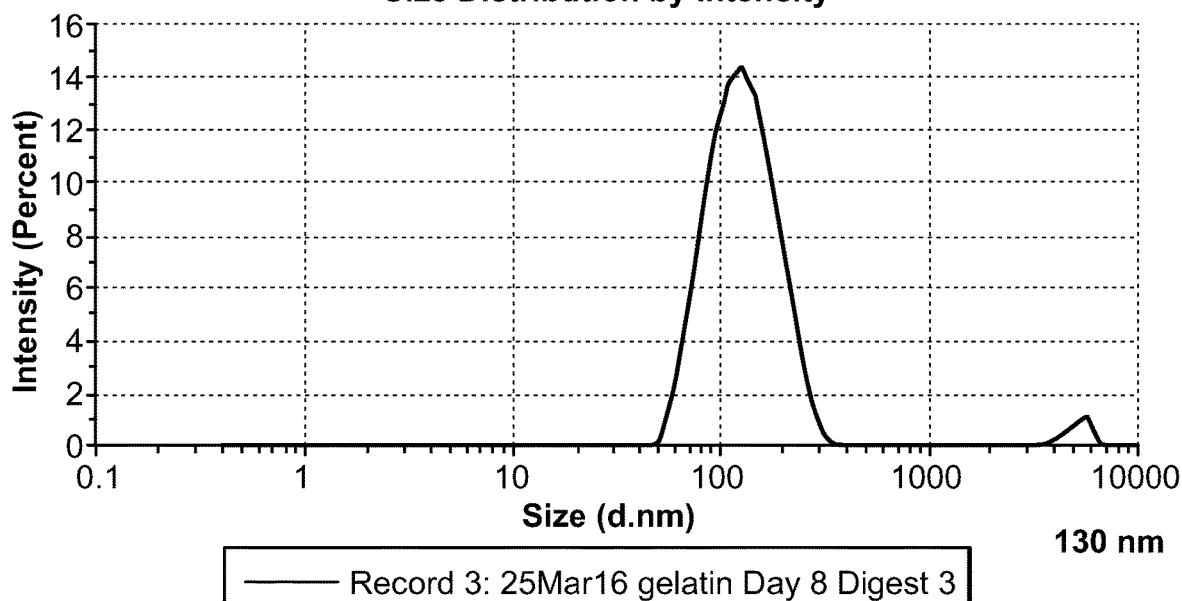
FIG. 17d is a DLS trace of a liposome which has been released from a click conjugated gelatin hydrogel digested with collagenase after 8 days.

FIG. 17d is a DLS trace of a liposome which has been released from a click conjugated gelatin hydrogel digested with collagenase after 8 days.

Figure 17E:
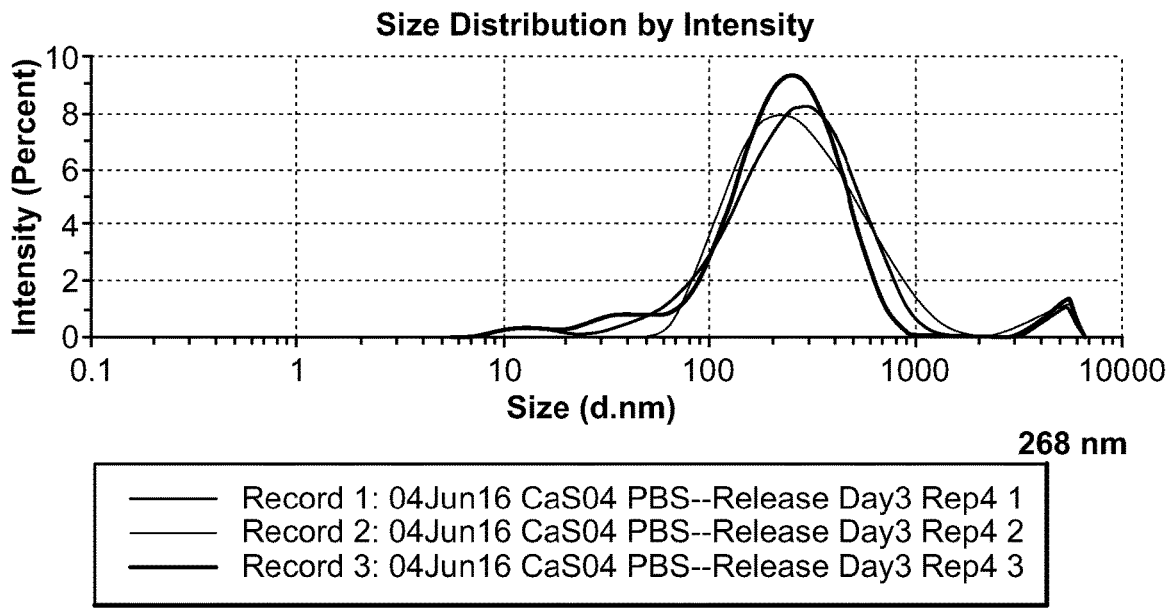
FIG. 17e is a DLS trace of a liposome which has been released after 3 days from a calcium cross-linked alginate prepared in PBS⁻ buffer, showing that released liposomes are more polydisperse and of greater diameter than the liposome standard.

FIG. 17e is a DLS trace of a liposome which has been released after 3 days from a calcium cross-linked alginate prepared in PBS⁻⁻ buffer.

Figure 17F:
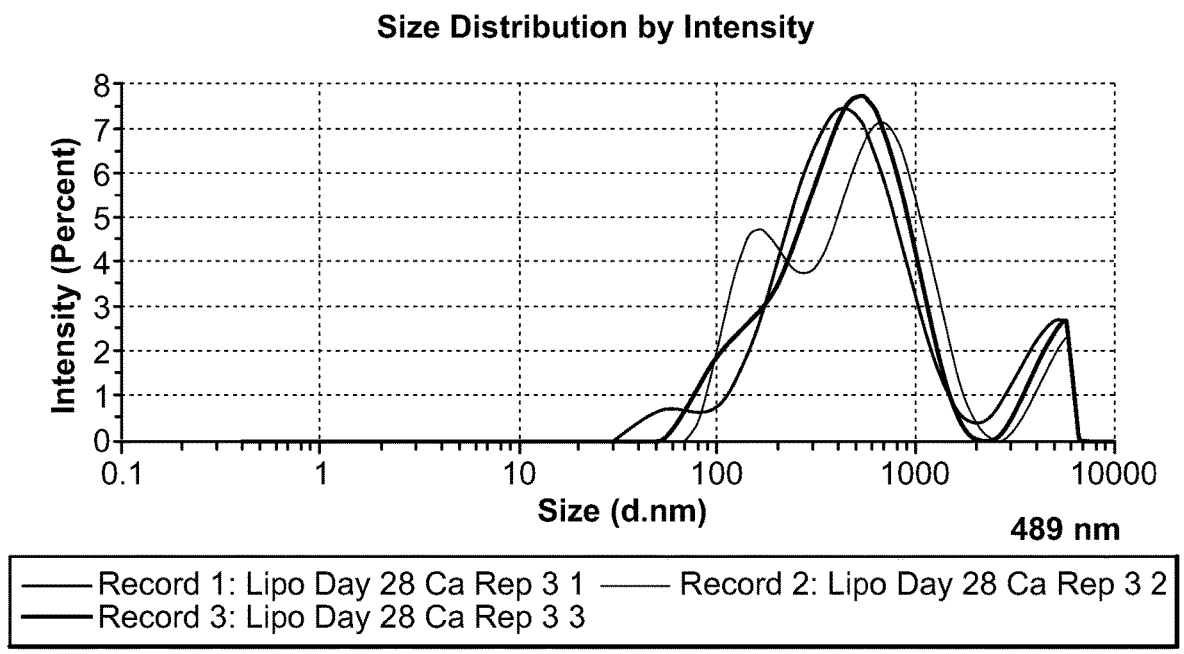
FIG. 17f is a DLS trace of a liposome which has been released after 28 days from a calcium cross-linked hydrogel prepared at the alginate concentration of 5% w/v in PBS⁻ buffer, showing that released liposomes are more polydisperse and of greater diameter than the liposome standard.

FIG. 17f is a DLS trace of a liposome which has been released after 28 days from a calcium cross-linked hydrogel prepared at the alginate concentration of 5% w/v in PBS⁻⁻ buffer.

The data in FIGS. 17a-17f demonstrate that liposomes released from click conjugated alginate or gelatin hydrogels are of similar size as the liposome standard, which indicates that they remain intact after 28 days. In contrast, the liposomes released from calcium cross-linked alginate hydrogels have a substantially greater range in sizes as compared to the liposome standard. This suggests that during the calcium cross-linking process the liposomes are torn apart due to sheer forces and subsequently undergo confluence in solution, resulting in liposomal particles of bigger size. Calcium cross-linking also introduces significant heterogeneity due to poor distribution of calcium.

Example 18. Influence of the Degree of Alginate Oxidation on the Ability of Alginate Hydrogels to Retain Liposomes The purpose of this experiment was to assess the influence of the degree of alginate oxidation in alginate hydrogels on their ability to retain encapsulated liposomes. This experiment utilized alginate hydrogels that were prepared from MVG alginate material that was cross-linked to Nb or Tz using 250 equivalents of Nb or Tz in the click conjugation reaction. Prior to click conjugation, the alginate was oxidized to 0%, 5% or 10% total oxidation and then reductively processed with AB using the procedures as described in Examples 1 and 2. Liposomes as described in Example 16 were encapsulated in the hydrogels, and their release was monitored in vitro by measuring the increase in DiI fluorescence in the supernatant over the period of 75 days.

Figure 18:
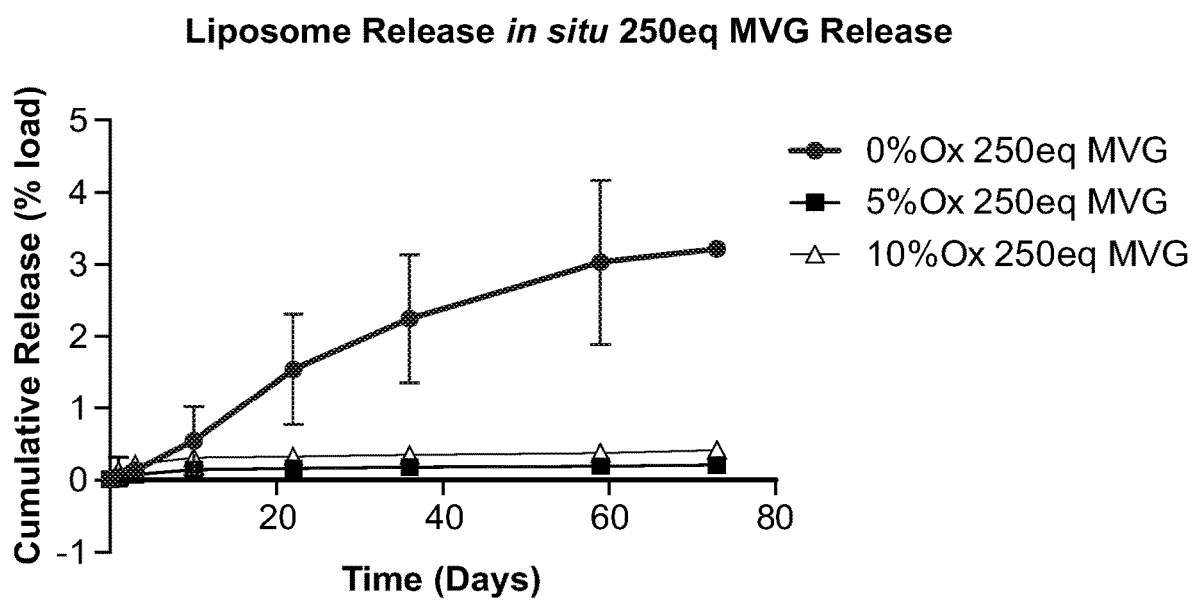
FIG. 18 is a graph showing cumulative release (% load) of liposomes over 75 days in PBS from click conjugated alginate hydrogels that were oxidized to 0%, 5% and 10% total oxidation and reductively processed with AB prior to click conjugation.

FIG. 18 is a graph showing cumulative release (% load) of liposomes over 75 days from click conjugated alginate hydrogels that were oxidized to 0%, 5% and 10% total oxidation and reductively processed with AB prior to click conjugation. The results in FIG. 18 demonstrate that oxidation of alginate to 5% or 10% and subsequent reduction of alginate prior to click conjugation allows retention of liposomes over the period of 75 days with detectable liposome release, while non-oxidized alginate releases about 3% of liposomes over 75 days. Therefore, oxidation of alginate improves the retention of liposomes by alginate hydrogels.

Example 19. Influence of pH on the Stability of Alginate Hydrogels

The purpose of this experiment was to investigate the release of liposomal cargo from alginate hydrogels as a function of pH. Because alginate biodegradation is acid or alkaline mediated, release of liposomal cargo from alginate hydrogels was monitored at pH 5 (in 0.1 M sodium citrate buffer) and pH 9 (in 0.1 M sodium borate buffer) over 14 days. Samples were prepared by firstly oxidizing MVG alginate to 20% oxidation, and subsequently reducing the material using ammonia borane. After 7 days, the pH 9 samples were mostly degraded, and after 14 days, the pH 5 samples were also found to be degraded.

Figure 19A:
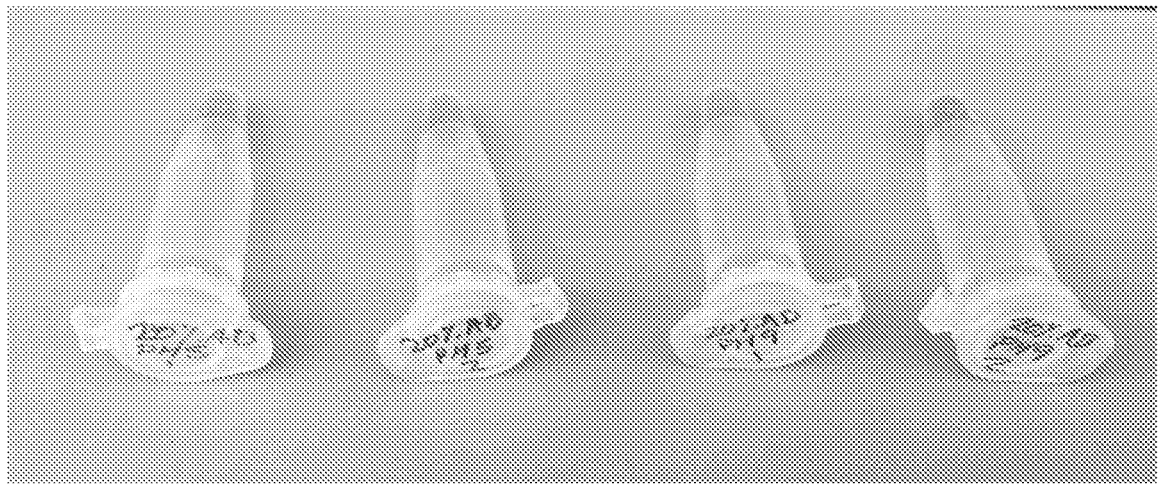
FIG. 19a is a picture of tubes containing alginate hydrogels encapsulating liposomes and supernatants at day 0. To prepare alginate hydrogels, alginate was oxidized to 20% and then subsequently reduced with ammonia borane. Gels were incubated at 37° C. in either sodium citrate buffer (pH 5; two vials on the left) or sodium borane (pH 9; two vials on the right).
Figure 19B:
FIG. 19b is a picture of tubes containing alginate hydrogels encapsulating liposomes and supernatants at day 1. To prepare alginate hydrogels, alginate was oxidized to 20% and then subsequently reduced with ammonia borane. Gels were incubated at 37° C. in either sodium citrate buffer (pH 5; two vials on the left) or sodium borane (pH 9; two vials on the right).
Figure 19C:
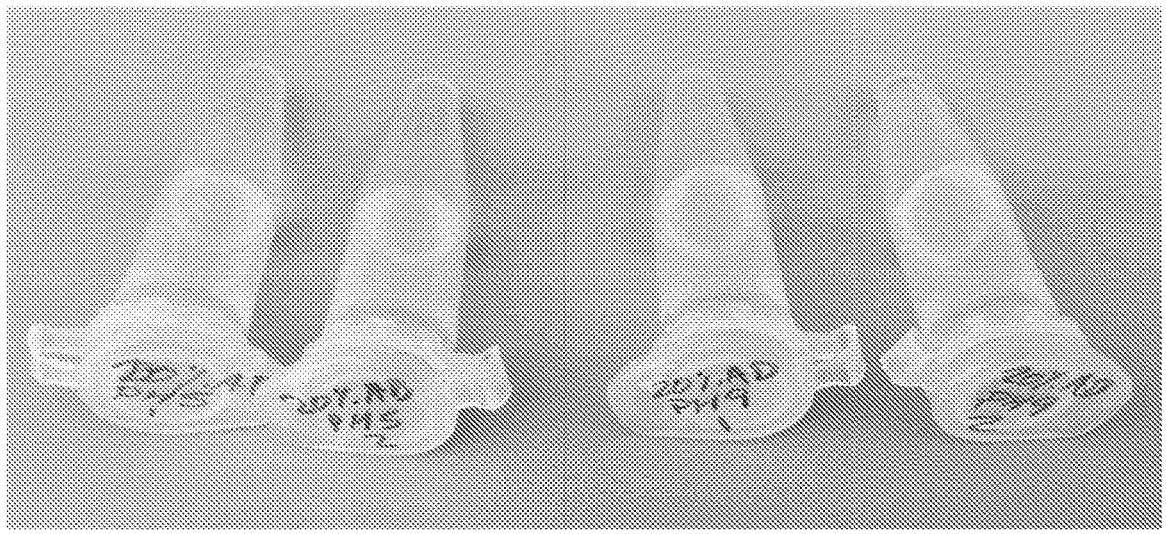
FIG. 19c is a picture of tubes containing alginate hydrogels encapsulating liposomes and supernatants at day 7. To prepare alginate hydrogels, alginate was oxidized to 20% and then subsequently reduced with ammonia borane. Gels were incubated at 37° C. in either sodium citrate buffer (pH 5; two vials on the left) or sodium borane (pH 9; two vials on the right). The pictures indicate that the pH 9 samples were degraded after 7 days, while the pH 5 samples were still somewhat intact.
Figure 19D:
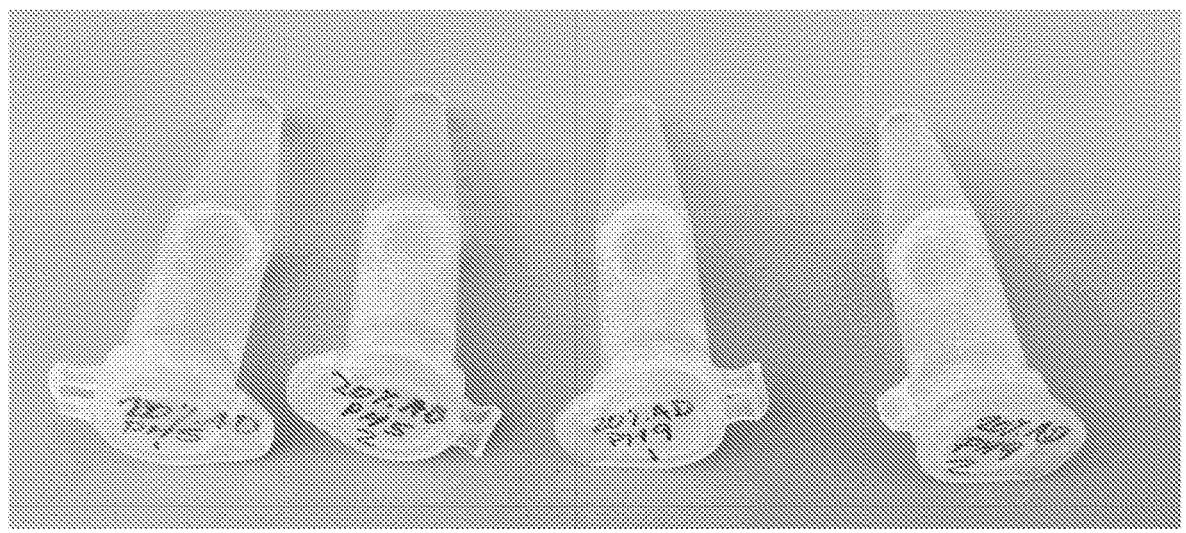
FIG. 19d is a picture of tubes alginate hydrogels encapsulating liposomes and supernatants at day 14. To prepare alginate hydrogels, alginate was oxidized to 20% and then subsequently reduced with ammonia borane. Gels were incubated at 37° C. in either sodium citrate buffer (pH 5; two vials on the left) or sodium borane (pH 9; two vials on the right). Images indicate that the samples were degraded after 14 days both at the pH 5 and pH 9.
Figure 19E:
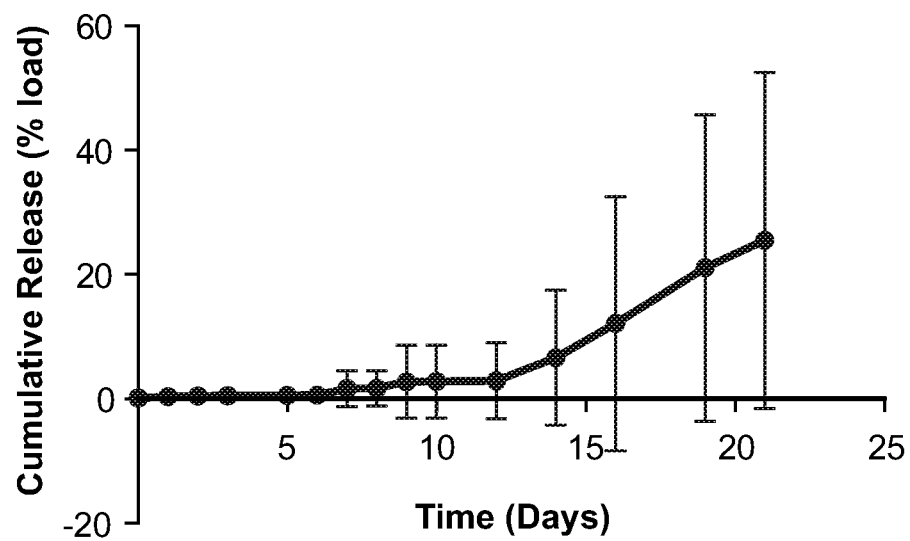
FIG. 19e is a graph showing the degradation based release of neutral liposomes (DOPC:Cholesterol) from alginate hydrogels that have been produced by oxidizing alginate to 20% and subsequently reducing it with ammonia borane. Samples were released in MES buffer pH 6.5 to mimic the paratumoral microenvironment.

FIG. 19a is a picture of tubes containing hydrogels with encapsulated liposomes comprising 20% oxidized MVG that has been reduced with ammonia borane, hydrogels and supernatants at day 0. FIG. 19b is a picture of tubes containing hydrogels with encapsulated liposomes, prepared using 20% oxidized MVG that has been reduced with ammonia borane and supernatants at day 1. FIG. 19c is a picture of tubes containing hydrogels with encapsulated liposomes, prepared using 20% oxidized MVG, that has been reduced with ammonia borane and supernatants at day 7. FIG. 19d is a picture of tubes containing hydrogels with encapsulated liposomes, prepared using 20% oxidized MVG, that has been reduced with ammonia borane and supernatants at day 14. FIG. 19e is a graph showing the degradation based release of neutral liposomes (DOPC: Cholesterol) from alginate hydrogels that have been produced by oxidizing alginate to 20% and subsequently reducing it with ammonia borane. Samples were released in MES buffer pH 6.5 to mimic the paratumoral microenvironment.

The results in FIGS. 19a-19d demonstrate that alginate is degraded and the liposomes diffuse into the supernatant at the acidic pH (pH 5) or basic pH (pH 9), but not at a neutral pH (7). Accordingly, liposomal release from click alginate hydrogels is pH sensitive and allows for degradation mediated release of liposomal cargo.

Example 20. Encapsulation and Retention of Cationic Liposomes by Alginate Hydrogels Previous experiments (e.g., the experiments described in Example 16) utilized DOPC/CHOL liposomes that were neutral. The purpose of this experiment was to investigate the ability of alginate hydrogels to encapsulate and retain charged liposomes e.g., cationic liposomes. This experiment utilized cationic liposomes containing N-[1-(2,3-Dioleoyloxy)propyl]-N,N,N-trimethylammonium methyl-sulfate (DOTAP) and hydrogenated soy phosphatidilcholine (Hydro Soy PC) having the average diameter of 133 nm. The liposomes also contained the fluorescent dye 1,1'-Dioctadecyl-3,3,3',3'-Tetramethylindocarbocyanine Perchlorate (DiI). These liposomes were encapsulated in calcium cross-linked alginate material and in non-oxidized click conjugated alginate that utilized 250 molar equivalents of click reagents in the conjugation reaction. Release of cationic liposomes from the hydrogels was monitored as described in Example 16.

Figure 20A:
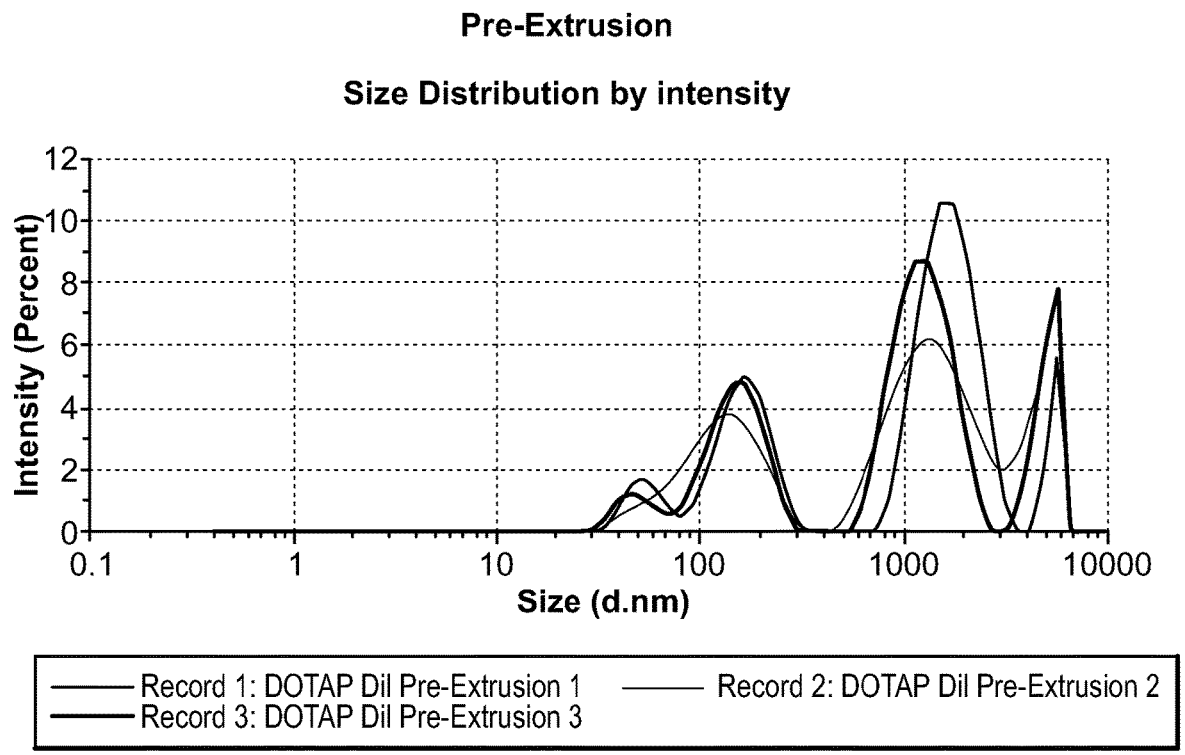
FIG. 20a is a DLS trace of a DOTAP:Hydro Soy PC liposome prior to extrusion.
Figure 20B:
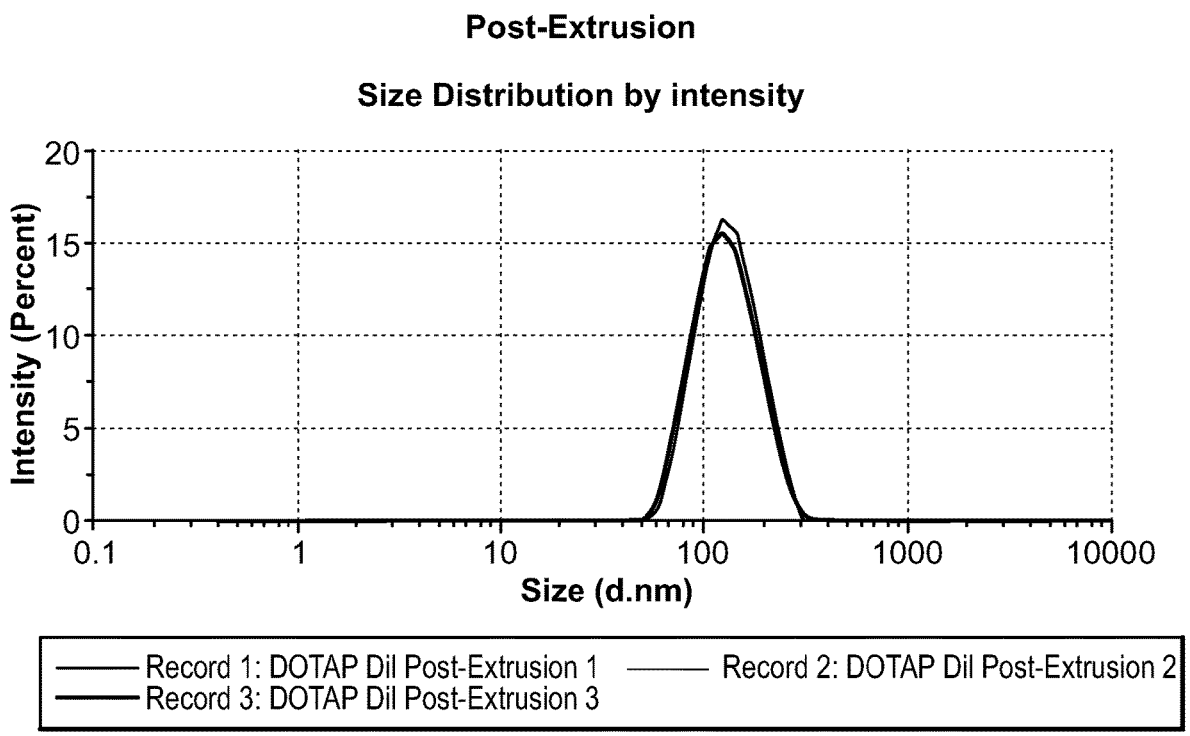
FIG. 20b is a DLS trace of DOTAP:Hydro Soy PC liposomes after extrusion.

FIG. 20a is a DLS trace of a DOTAP:Hydro Soy PC liposome prior to extrusion, while FIG. 20b is a DLS trace of the same liposome after extrusion. FIGS. 20a and 20b demonstrate that it is possible to prepare cationic liposomes of a uniform size using extrusion.

Figure 20C:
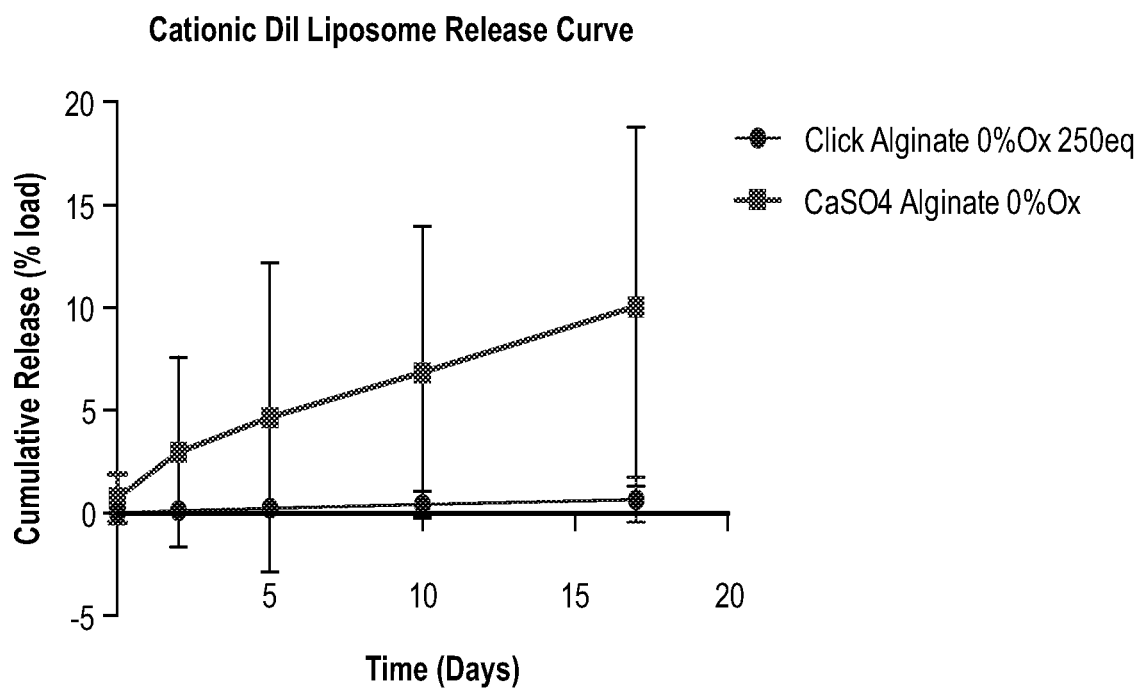
FIG. 20c is a graph showing cumulative release (% load) of cationic liposomes (FIG. 20a) over the period of 17 days from $Ca^{2+}$ cross-linked alginate and from non-oxidized click conjugated alginate hydrogels.

FIG. 20c is a graph showing cumulative release (% load) of cationic liposomes over the period of 17 days from $Ca^{2+}$ cross-linked alginate and from non-oxidized click conjugated alginate hydrogels. The results in FIG. 20c demonstrate that click conjugated alginate hydrogel can encapsulate and effectively retain cationic liposomes over the period of 17 days. In contrast, release of cationic liposomes from the calcium cross-linked alginate hydrogel is evident after only 2 days.

Example 21. Protein Release Profiles from Algoxinol and Algoxalate Composite Click Hydrogels The goal of this experiment was to evaluate different protein release profiles from the hydrogels prepared using different oxidized and reduced alginate materials that have been click conjugated. The compositions used to prepare the alginate hydrogels included: a) equal parts MVG at 10% w/v that has been oxidized to 50% and subsequently oxidized with sodium chlorite and conjugated with Tz at 2000 equivalents and MVG at 10% w/v that has been oxidized to 10% and subsequently reduced with ammonia borane and conjugated with Nb at 2000 equivalents; b) equal parts MVG at 10% w/v that has been oxidized to 50% and subsequently reduced with ammonia borane and conjugated with Tz at 250 equivalents and MVG at 10% w/v that has been oxidized to 10% and subsequently reduced with ammonia borane and conjugated with Nb at 250 equivalents; c) 7 parts MVG at 10% w/v that has been oxidized to 10% and subsequently reduced with ammonia borane and conjugated with Nb at 2000 equivalents and 3 parts MVG at 10% w/v that has been oxidized to 50% and subsequently reduced with ammonia borane and conjugated with Tz at 2000 equivalents; and d) 3 parts MVG and 1 part MVG that has been crosslinked with calcium sulfate.

Protein release curves were evaluated by encapsulating Human IGF and human VEGF (R&D Systems) in various click hydrogels. Samples were prepared by first separately dissolving freeze-dried Alg-N and Alg-T polymers of various degrees of substitution to final desired concentration (w/v) in PBS. The proteins were added and mixed with the Alg-N solution to reach a 2 µg/gel (100 µL) final concentration. The Protein-Alg-N solution was thoroughly mixed with the Alg-T solution and was allowed to gel for at least 30 minutes. Samples were created by adding 1 mL of PBS with 1% BSA to each gel and incubated at 37° C. Samples were collected at various timepoints with replacement of the supernatant at each timepoint. Supernatant protein content with VEGF and IGF was quantified with Human VEGF and IGF Quantikine ELISA kits (R&D Systems) using a standard curve of comparable sample matrix (PBS w/1% BSA and PBS w/5% Tween 20, respectively).

Figure 21A:
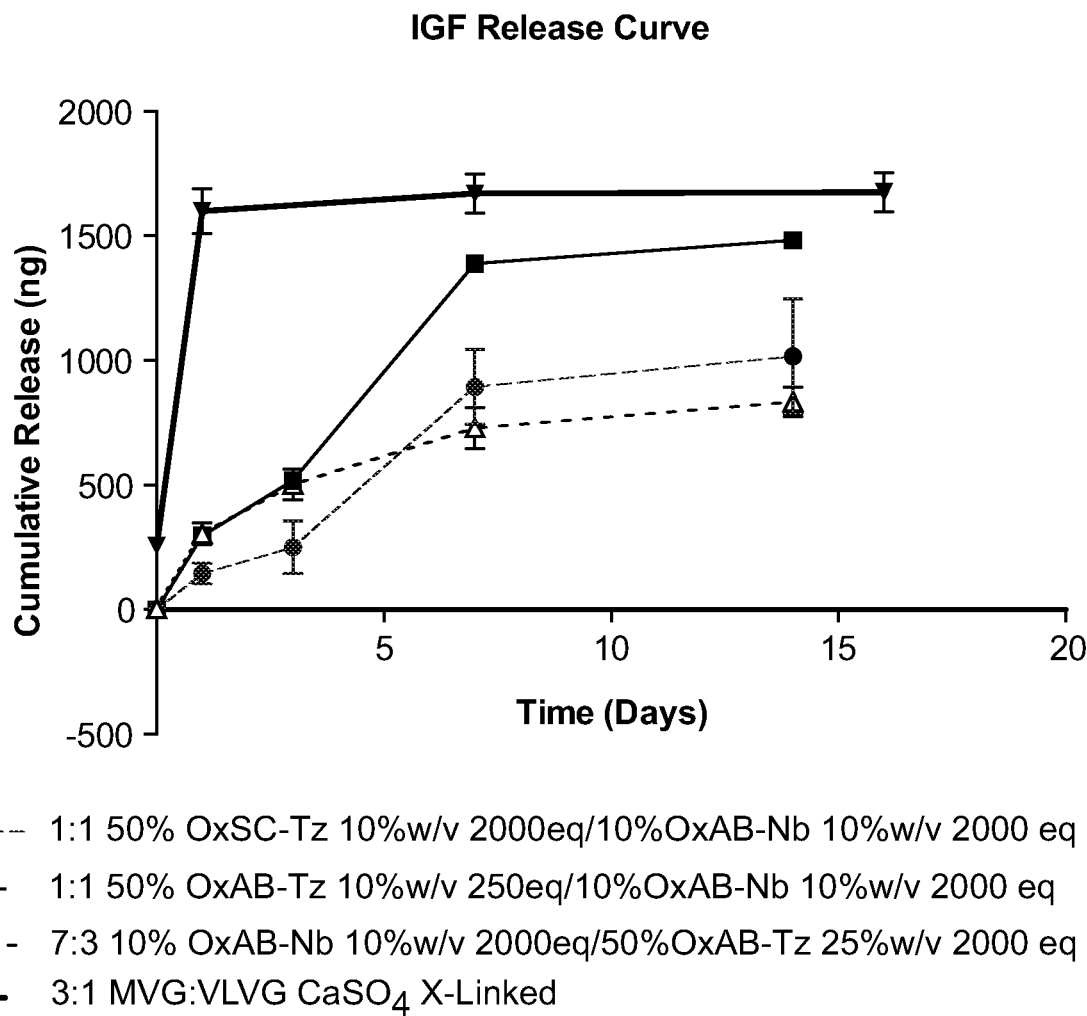
FIG. 21a is a graph showing the release of IGF-1 from click conjugated alginate hydrogels prepared using various alginate compositions.
Figure 21B:
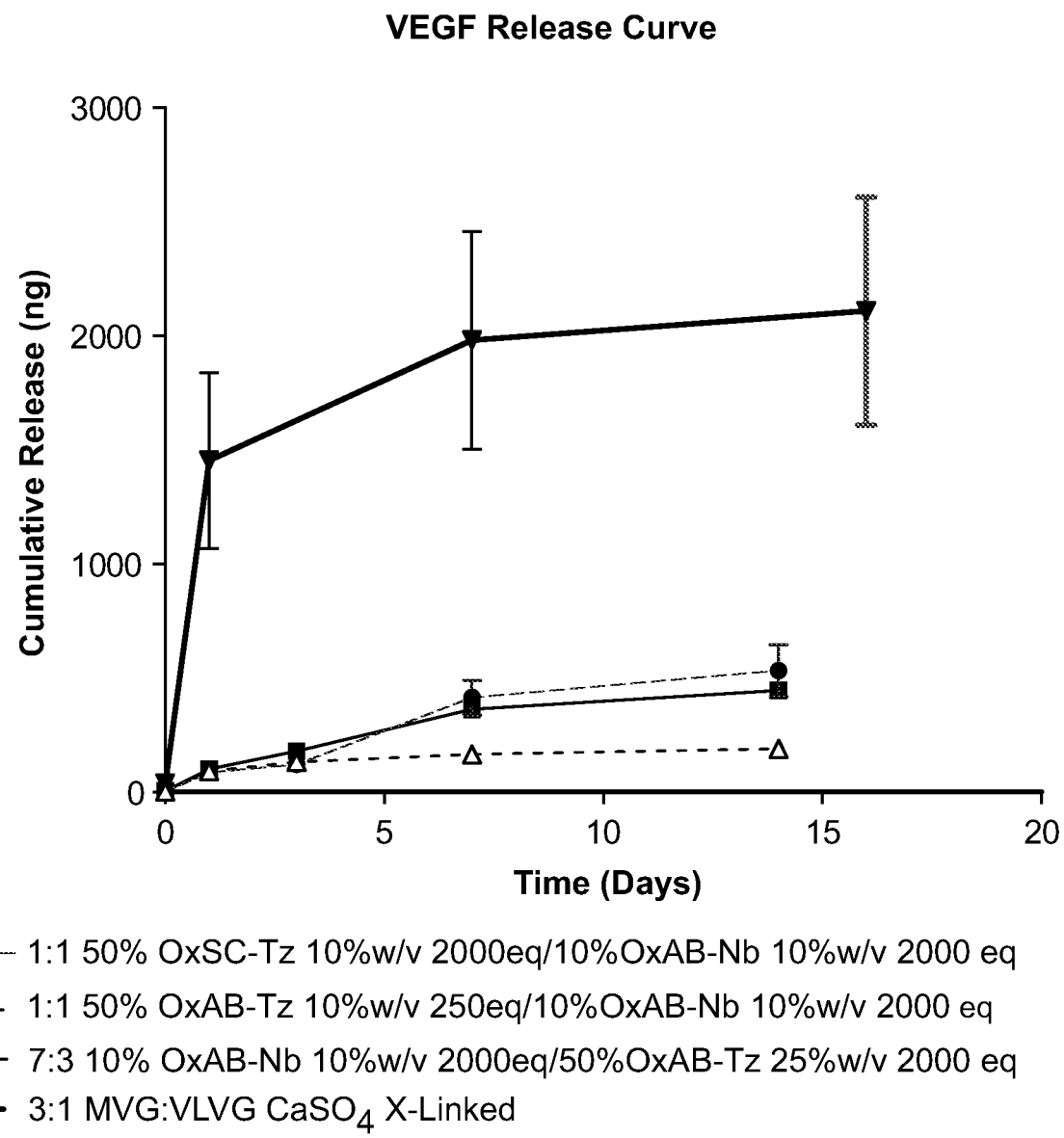
FIG. 21b shows that click-crosslinked gels are able to retain the encapsulated liposomes (diffusion limited), while liposomes are able to diffuse out of the calcium crosslinked gels.

FIG. 21a is a graph showing the release of IGF-1 from click conjugated alginate hydrogels prepared using various alginate compositions. FIG. 21b is a graph showing the release of VEGF$_{165}$ from click alginate hydrogels prepared using various alginate compositions.

The data in FIGS. 21a and 21b show the ability to modulate the burst release of IGF-1 and VEGF$_{165}$ using the click gels prepared using different alginate compositions. In contrast, calcium crosslinked alginate hydrogels are unable to modulate diffusion. This example demonstrates that it is possible to modulate protein release via various combinations of the algoxinol and algoxalate containing alginate, alginate degree of substitution, alginate concentration, and ratio of Nb to Tz.

Example 22. Viscosity of Alginate Solutions

The goal of this experiment was to investigate the viscosity of click conjugated alginate solutions as a function of alginate oxidation and/or reduction. To this end, click alginate solutions were evaluated for relative viscosity by first separately dissolving freeze-dried Alg-N and Alg-T polymers to final desired concentration (w/v) in ddH$_2$O. Solutions were directly pipetted onto the bottom plate of a TA Instruments ARG2 rheometer equipped with 20 mm flat upper plate geometry and a 400-micron geometry gap. A Peltier cooler was used to control the temperature (20° C.). Alginate samples were subjected to strains between 0.1 and 1 Hz.

Figure 22:
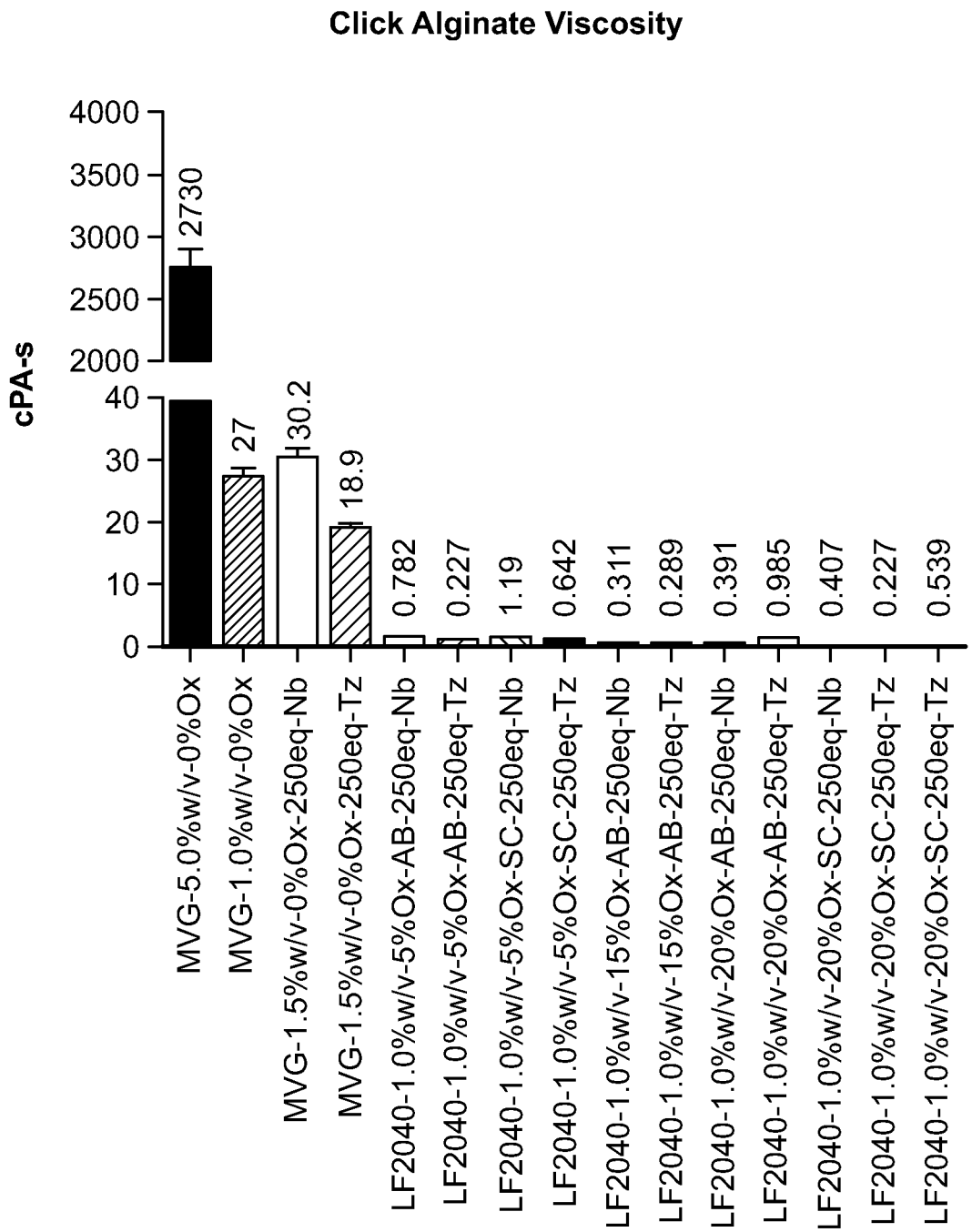
FIG. 22 is a bar graph showing the relative viscosities of various alginate solutions at different alginate concentrations (% w/v), degrees of oxidation, and processing with either sodium chlorite or ammonia borane. Data shows that click conjugation to MVG without oxidation does not result in substantial difference in viscosity, whereas the viscosity is substantially reduced with click conjugation to alginate containing either algoxinol or algoxalate, and is comparable to that of water (0.890 cPa at 25° C.).

FIG. 22 is a bar graph showing the relative viscosities of various alginate solutions at different alginate concentrations (% w/v), degrees of oxidation, and processing with either sodium chlorite or ammonia borane. The data demonstrate that click conjugation to MVG without oxidation does not result in substantial differences in viscosity, whereas the viscosity is substantially reduced with click conjugation to alginate containing either algoxinol or algoxalate, and is comparable to that of water (0.890 cPa at 25° C.).

What is claimed is:

1. A composition comprising a reduced polysaccharide, wherein
said reduced polysaccharide comprises less than 2% of residual aldehydes;
said reduced polysaccharide comprises ring opened monomeric subunits comprising alcohol moieties; and
wherein said reduced polysaccharide is selected from the group consisting of reduced alginate, agarose, pullulan, scleroglucan, chitosan, elsinan, xanthan gum, mannose, gellan, levan, cellulose, hyaluronic acid, chondroitin sulfate A, chondroitin sulfate C, chondroitin sulfate E and β-d-glucans.

2. The composition of claim 1, wherein said reduced polysaccharide is reduced alginate.

3. The composition of claim 2, wherein said reduced alginate comprises algoxinol having the following structure:

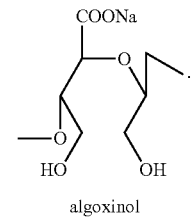

algoxinol

4. The composition of claim 1, wherein said composition further comprises a cross-linking agent attached to the reduced polysaccharide.

5. The composition of claim 4, wherein said cross-linking agent is a click reagent.

6. A hydrogel comprising a plurality of reduced polysaccharides cross-linked to each other, wherein said hydrogel comprises a mesh size of 10 nm or less, wherein
said reduced polysaccharides comprise less than 2% of residual aldehydes;
said reduced polysaccharides comprise ring opened monomeric subunits comprising alcohol moieties; and
wherein said reduced polysaccharides are selected from the group consisting of reduced alginate, agarose, pullulan, scleroglucan, chitosan, elsinan, xanthan gum, mannose, gellan, levan, cellulose, hyaluronic acid, chondroitin sulfate A, chondroitin sulfate C, chondroitin sulfate E and β-d-glucans.

7. The hydrogel of claim 6, wherein said reduced polysaccharides comprising less than 2% of residual aldehydes are reduced alginate polymers produced by a method comprising the steps of:
reacting an alginate with a diol specific oxidizing agent to produce an aldehyde containing oxidized alginate; and
reacting said aldehyde containing oxidized alginate with a water soluble aldehyde specific reducing agent, thereby producing said reduced alginate polymers.

8. The hydrogel of claim 7, wherein said diol specific oxidizing agent is sodium periodate and wherein said water soluble aldehyde specific reducing agent is ammonia borane.

9. The hydrogel of claim 6, further comprising a therapeutic or diagnostic agent selected from the group consisting of a cell, a small molecule and a biologic.

10. The hydrogel of claim 6, wherein said reduced polysaccharides comprise a cross-linking agent attached to the reduced polysaccharides.

11. An implantable or injectable device comprising the hydrogel of claim 6.

12. A drug delivery composition comprising
a lipid based nanoparticle encapsulating a therapeutic or diagnostic agent; and
the hydrogel of claim 6 encapsulating said lipid based nanoparticle.

13. A method for treating a subject in need thereof, the method comprising administering to said subject an effective amount of a hydrogel of claim 6, thereby treating said subject.

14. A method of treating chronic ischemia or enhancing engraftment of a transplanted tissue in a subject in need thereof, the method comprising administering to said subject an effective amount of a hydrogel of claim 6, thereby treating said chronic ischemia or enhancing engraftment of said transplanted tissue in said subject.

15. The composition of claim 1, wherein said reduced polysaccharide is produced by reacting a polysaccharide with a diol specific oxidizing agent, thereby producing a diol containing oxidized polysaccharide comprising 0.1% or more oxidation on a molar basis; followed by reacting said oxidized polysaccharide with a water soluble aldehyde specific reducing agent to produce said reduced polysaccharide.

16. The composition of claim 15, wherein said aldehyde specific water soluble reducing agent is selected from the group consisting of sodium cyanoborohydride ($NaCNBH_3$); hydrogen gas ($H_2$) in the presence of a catalyst; ammonia borane ($H_3NBH_3$); and a borane complex.

17. The composition of claim 16, wherein said aldehyde specific water soluble reducing agent is ammonia borane.

18. The composition of claim 15, wherein said diol specific oxidizing agent is sodium periodate.

19. The composition of claim 4, wherein said cross-linking agent is attached to said reduced polysaccharide via a carboxylic moiety.

20. The composition of claim 5, wherein said click reagent is selected from the group consisting of azide, dibenzocyclooctyne (DBCO), transcyclooctene, tetrazine and norbornene and variants thereof.

21. The hydrogel of claim 10, wherein said cross-linking agent is a click reagent.

22. The hydrogel of claim 21, wherein said click reagent is selected from the group consisting of azide, dibenzocyclooctyne, transcyclooctene, tetrazine and norbornene and variants thereof.

23. The hydrogel of claim 10, wherein said cross-linking agent is attached to the reduced polysaccharides via a carboxylic moiety.

* * * * *